United States Patent
Lane et al.

(10) Patent No.: US 10,583,002 B2
(45) Date of Patent: Mar. 10, 2020

(54) PROSTHETIC VALVE WITH ANTI-PIVOTING MECHANISM

(71) Applicant: Neovasc Tiara Inc., Richmond (CA)

(72) Inventors: Randy Matthew Lane, Langley (CA); Colin A. Nyuli, Vancouver (CA); Alexei J. Marko, Vancouver (CA); Krista L. Neale, Vancouver (CA)

(73) Assignee: Neovasc Tiara Inc., Richmond, British Columbia ( * ) Notice: Subject to any disclaimer, the term of this patent is extended or adjusted under 35 U.S.C. 154(b) by 0 days.

(21) Appl. No.: 14/195,576

(22) Filed: Mar. 3, 2014

(65) Prior Publication Data

US 2014/0257467 A1    Sep. 11, 2014

Related U.S. Application Data

(60) Provisional application No. 61/776,566, filed on Mar. 11, 2013.

(51) Int. Cl.
*A61F 2/24* (2006.01)

(52) U.S. Cl.
CPC .......... *A61F 2/2412* (2013.01); *A61F 2/2418* (2013.01); *A61F 2/2436* (2013.01);
(Continued)

(58) Field of Classification Search
CPC ........ A61F 2/24; A61F 2/2403; A61F 2/2406; A61F 2/2409; A61F 2/2412;
(Continued)

(56) References Cited

U.S. PATENT DOCUMENTS

| | | |
|---|---|---|
| 3,657,744 A | 4/1972 | Ersek |
| 3,671,979 A | 6/1972 | Moulopoulos |

(Continued)

FOREIGN PATENT DOCUMENTS

| | | |
|---|---|---|
| AU | 2014231689 A1 | 8/2015 |
| CA | 2304325 A1 | 10/2000 |

(Continued)

OTHER PUBLICATIONS

US 8,062,357 B2, 11/2011, Salahieh et al. (withdrawn)
(Continued)

*Primary Examiner* — Katherine H Schwiker
(74) *Attorney, Agent, or Firm* — Schwegman Lundberg & Woessner, P.A.

(57) ABSTRACT

A prosthetic valve for implanting in a patient's native valve has a self-expanding frame that comprises a first end, a second end opposite the first end, an anterior portion, and a posterior portion. The self-expanding frame has an expanded configuration adapted to engage tissue at a treatment site, and a collapsed configuration adapted to be delivered to the treatment site. The expandable frame also comprises a self-expanding atrial skirt near the second end, a self-expanding ventricular skirt near the first end, a self-expanding annular region disposed between first and second ends, a first self-expanding anterior tab disposed on the anterior portion, and a self-expanding foot coupled to the posterior portion and extending radially outward. The foot has an outer surface for engaging the tissue thereby facilitating anchoring of the prosthetic valve and minimizing or preventing rotation of the prosthetic valve.

36 Claims, 51 Drawing Sheets

(52) U.S. Cl.
CPC ............... *A61F 2220/0016* (2013.01); *A61F 2220/0075* (2013.01); *A61F 2230/0034* (2013.01); *A61F 2230/0065* (2013.01)

(58) Field of Classification Search
CPC ...... A61F 2/2418; A61F 2/2427; A61F 2/243; A61F 2/2436; A61F 2/2439; A61F 2/2469; A61F 2/2442; A61F 2/2445; A61F 2/2448; A61F 2/2454; A61F 2/2457; A61F 2230/0034; A61F 2230/0065; A61F 2250/0067; A61F 2220/0008; A61F 2220/0016; A61F 2220/0075; A61F 2230/0054; A61F 2230/005; Y10S 623/904; Y10S 623/90; A61D 2/2415; A61D 2/2433
USPC ........................................................ 623/2.11
See application file for complete search history.

(56) References Cited

U.S. PATENT DOCUMENTS

| | | |
|---|---|---|
| 3,739,402 A | 6/1973 | Kahn et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,655,771 A | 4/1987 | Wallsten et al. |
| 4,733,665 A | 3/1988 | Palmaz et al. |
| 4,776,337 A | 10/1988 | Palmaz et al. |
| 4,777,951 A | 10/1988 | Cribier et al. |
| 4,865,600 A | 9/1989 | Carpentier et al. |
| 4,950,227 A | 8/1990 | Savin et al. |
| 4,994,077 A | 2/1991 | Dobben |
| 5,067,957 A | 11/1991 | Jervis |
| 5,197,978 A | 3/1993 | Hess et al. |
| 5,326,371 A | 7/1994 | Love et al. |
| 5,332,402 A | 7/1994 | Teitelbaum |
| 5,344,427 A | 9/1994 | Cottenceau et al. |
| 5,370,685 A | 12/1994 | Stevens |
| 5,397,355 A | 3/1995 | Marin et al. |
| 5,411,552 A | 5/1995 | Andersen et al. |
| 5,415,667 A | 5/1995 | Frater |
| 5,439,446 A | 8/1995 | Barry |
| 5,474,563 A | 12/1995 | Myler et al. |
| 5,509,930 A | 4/1996 | Love |
| 5,545,214 A | 8/1996 | Stevens |
| 5,554,185 A | 9/1996 | Block et al. |
| 5,575,818 A | 11/1996 | Pinchuk |
| 5,607,444 A | 3/1997 | Lam |
| 5,607,469 A | 3/1997 | Frey |
| 5,669,919 A | 9/1997 | Sanders et al. |
| 5,697,382 A | 12/1997 | Love et al. |
| D390,957 S | 2/1998 | Fontaine |
| 5,713,952 A | 2/1998 | Vanney et al. |
| 5,725,519 A | 3/1998 | Penner et al. |
| 5,769,812 A | 6/1998 | Stevens et al. |
| 5,807,398 A | 9/1998 | Shaknovich |
| 5,810,873 A | 9/1998 | Morales |
| 5,824,069 A | 10/1998 | Lemole et al. |
| 5,840,081 A | 11/1998 | Andersen et al. |
| 5,855,601 A | 1/1999 | Bessler et al. |
| 5,868,777 A | 2/1999 | Lam |
| 5,868,782 A | 2/1999 | Frantzen |
| 5,876,437 A | 3/1999 | Vanney et al. |
| 5,879,381 A | 3/1999 | Moriuchi et al. |
| 5,902,334 A | 5/1999 | Dwyer et al. |
| 5,928,281 A | 7/1999 | Huynh et al. |
| 5,935,108 A | 8/1999 | Katoh et al. |
| 5,954,764 A | 9/1999 | Parodi |
| 5,957,949 A | 9/1999 | Leonhardt et al. |
| 5,992,000 A | 11/1999 | Humphrey et al. |
| 6,004,328 A | 12/1999 | Solar |
| 6,015,431 A | 1/2000 | Thornton et al. |
| 6,042,606 A | 3/2000 | Frantzen |
| 6,053,940 A | 4/2000 | Wijay |
| 6,074,417 A | 6/2000 | Peredo |
| 6,086,612 A | 7/2000 | Jansen |
| 6,113,612 A | 9/2000 | Swanson et al. |
| 6,113,631 A | 9/2000 | Jansen |
| 6,132,458 A | 10/2000 | Staehle et al. |
| 6,152,937 A | 11/2000 | Peterson et al. |
| 6,159,237 A | 12/2000 | Alt et al. |
| 6,168,614 B1 | 1/2001 | Andersen et al. |
| 6,168,616 B1 | 1/2001 | Brown, III |
| 6,251,093 B1 | 6/2001 | Valley et al. |
| 6,280,466 B1 | 8/2001 | Kugler et al. |
| 6,306,141 B1 | 10/2001 | Jervis |
| 6,312,465 B1 | 11/2001 | Griffin et al. |
| 6,336,938 B1 | 1/2002 | Kavteladze et al. |
| 6,352,543 B1 | 3/2002 | Cole |
| 6,358,277 B1 | 3/2002 | Duran |
| 6,425,916 B1 | 7/2002 | Garrison et al. |
| 6,440,164 B1 | 8/2002 | Dimatteo et al. |
| 6,458,153 B1 | 10/2002 | Bailey et al. |
| 6,475,237 B2 | 11/2002 | Drasler et al. |
| 6,482,228 B1 | 11/2002 | Norred |
| 6,511,491 B2 | 1/2003 | Grudem et al. |
| 6,517,573 B1 | 2/2003 | Pollock et al. |
| 6,527,800 B1 | 3/2003 | McGuckin, Jr. et al. |
| 6,551,303 B1 | 4/2003 | Van Tassel et al. |
| 6,582,462 B1 | 6/2003 | Andersen et al. |
| 6,602,281 B1 | 8/2003 | Klein |
| 6,610,088 B1 | 8/2003 | Gabbay |
| 6,629,534 B1 | 10/2003 | Goar St et al. |
| 6,641,606 B2 | 11/2003 | Ouriel et al. |
| 6,652,578 B2 | 11/2003 | Bailey et al. |
| D484,979 S | 1/2004 | Fontaine |
| 6,676,698 B2 | 1/2004 | McGuckin et al. |
| 6,682,537 B2 | 1/2004 | Ouriel et al. |
| 6,695,878 B2 | 2/2004 | McGuckin et al. |
| 6,712,836 B1 | 3/2004 | Berg et al. |
| 6,723,123 B1 | 4/2004 | Kazatchkov et al. |
| 6,730,118 B2 | 5/2004 | Spenser et al. |
| 6,733,523 B2 | 5/2004 | Shaolian et al. |
| 6,764,505 B1 | 7/2004 | Hossainy et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,814,746 B2 | 11/2004 | Thompson et al. |
| 6,858,034 B1 | 2/2005 | Hijlkema et al. |
| 6,875,231 B2 | 4/2005 | Anduiza et al. |
| 6,893,460 B2 | 5/2005 | Spenser et al. |
| 6,908,477 B2 | 6/2005 | McGuckin et al. |
| 6,908,481 B2 | 6/2005 | Cribier |
| 6,926,732 B2 | 8/2005 | Derus et al. |
| 6,929,660 B1 | 8/2005 | Ainsworth et al. |
| 6,936,058 B2 | 8/2005 | Forde et al. |
| 6,979,350 B2 | 12/2005 | Moll et al. |
| 7,014,653 B2 | 3/2006 | Ouriel et al. |
| 7,018,401 B1 | 3/2006 | Hyodoh et al. |
| 7,018,406 B2 | 3/2006 | Seguin et al. |
| 7,025,780 B2 | 4/2006 | Gabbay |
| 7,044,962 B2 | 5/2006 | Elliot et al. |
| 7,044,966 B2 | 5/2006 | Svanidze et al. |
| 7,087,088 B2 | 8/2006 | Berg et al. |
| 7,147,660 B2 | 12/2006 | Chobotov et al. |
| 7,147,661 B2 | 12/2006 | Chobotov et al. |
| 7,147,663 B1 | 12/2006 | Berg et al. |
| 7,153,322 B2 | 12/2006 | Alt |
| 7,186,265 B2 | 3/2007 | Sharkawy et al. |
| 7,198,646 B2 | 4/2007 | Figulla et al. |
| 7,201,772 B2 | 4/2007 | Schwammenthal et al. |
| 7,252,682 B2 | 8/2007 | Seguin |
| D553,747 S | 10/2007 | Fliedner |
| 7,276,078 B2 | 10/2007 | Spenser et al. |

(56) References Cited

U.S. PATENT DOCUMENTS

| | | | |
|---|---|---|---|
| 7,276,084 B2 | 10/2007 | Yang et al. |
| 7,329,278 B2 | 2/2008 | Seguin et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Haug et al. |
| 7,455,689 B2 | 11/2008 | Johnson |
| 7,462,191 B2 | 12/2008 | Spenser et al. |
| 7,510,575 B2 | 3/2009 | Spenser et al. |
| 7,524,330 B2 | 4/2009 | Berreklouw |
| 7,527,646 B2 | 5/2009 | Rahdert et al. |
| 7,585,321 B2 | 9/2009 | Cribier |
| 7,608,114 B2 | 10/2009 | Levine et al. |
| 7,615,072 B2 | 11/2009 | Rust et al. |
| 7,618,446 B2 | 11/2009 | Andersen et al. |
| 7,618,447 B2 | 11/2009 | Case et al. |
| 7,628,805 B2 | 12/2009 | Spenser et al. |
| 7,632,298 B2 | 12/2009 | Hijlkema et al. |
| 7,637,945 B2 | 12/2009 | Solem et al. |
| 7,637,946 B2 | 12/2009 | Solem et al. |
| 7,682,390 B2 | 3/2010 | Seguin |
| 7,708,775 B2 | 5/2010 | Rowe et al. |
| 7,712,606 B2 | 5/2010 | Salahieh et al. |
| 7,748,389 B2 | 7/2010 | Salahieh et al. |
| 7,753,949 B2 | 7/2010 | Lamphere et al. |
| D622,387 S | 8/2010 | Igaki |
| D622,388 S | 8/2010 | Igaki |
| 7,771,463 B2 | 8/2010 | Ton et al. |
| 7,771,472 B2 | 8/2010 | Hendricksen et al. |
| 7,780,725 B2 | 8/2010 | Haug et al. |
| 7,785,360 B2 | 8/2010 | Freitag |
| 7,803,185 B2 | 9/2010 | Gabbay |
| 7,806,917 B2 | 10/2010 | Xiao |
| 7,806,919 B2 | 10/2010 | Bloom et al. |
| 7,815,589 B2 | 10/2010 | Meade et al. |
| 7,815,673 B2 | 10/2010 | Bloom et al. |
| 7,824,443 B2 | 11/2010 | Salahieh et al. |
| 7,837,727 B2 | 11/2010 | Goetz et al. |
| 7,846,203 B2 | 12/2010 | Cribier |
| 7,871,435 B2 | 1/2011 | Carpentier et al. |
| 7,892,281 B2 | 2/2011 | Seguin et al. |
| D635,261 S | 3/2011 | Rossi |
| D635,262 S | 3/2011 | Rossi |
| 7,896,915 B2 | 3/2011 | Guyenot et al. |
| 7,914,569 B2 | 3/2011 | Nguyen et al. |
| 7,919,112 B2 | 4/2011 | Pathak et al. |
| 7,947,075 B2 | 5/2011 | Goetz et al. |
| 7,959,672 B2 | 6/2011 | Salahieh et al. |
| 7,967,853 B2 | 6/2011 | Eidenschink et al. |
| 7,972,377 B2 | 7/2011 | Lane |
| 7,972,378 B2 | 7/2011 | Tabor et al. |
| 7,981,151 B2 | 7/2011 | Rowe |
| 7,993,392 B2 | 8/2011 | Righini et al. |
| 7,993,394 B2 | 8/2011 | Hariton et al. |
| 7,993,395 B2 | 8/2011 | Vanermen et al. |
| 7,998,196 B2 | 8/2011 | Mathison |
| 8,009,887 B2 | 8/2011 | Ionasec et al. |
| 8,016,870 B2 | 9/2011 | Chew et al. |
| 8,016,877 B2 | 9/2011 | Seguin et al. |
| 8,029,564 B2 | 10/2011 | Johnson et al. |
| 8,048,153 B2 | 11/2011 | Salahieh et al. |
| 8,052,747 B2 | 11/2011 | Melnikov et al. |
| 8,052,750 B2 | 11/2011 | Tuval et al. |
| 8,057,538 B2 | 11/2011 | Bergin et al. |
| 8,057,539 B2 | 11/2011 | Ghione et al. |
| 8,057,540 B2 | 11/2011 | Letac et al. |
| 8,062,350 B2 | 11/2011 | Gale et al. |
| 8,062,359 B2 | 11/2011 | Marquez et al. |
| 8,066,763 B2 | 11/2011 | Alt |
| 8,070,799 B2 | 12/2011 | Righini et al. |
| 8,070,800 B2 | 12/2011 | Lock et al. |
| 8,070,801 B2 | 12/2011 | Cohn |
| 8,070,802 B2 | 12/2011 | Lamphere et al. |
| 8,075,611 B2 | 12/2011 | Millwee et al. |
| 8,075,615 B2 | 12/2011 | Eberhardt et al. |
| 8,078,279 B2 | 12/2011 | Dennis et al. |
| 8,080,054 B2 | 12/2011 | Rowe |
| 8,083,793 B2 | 12/2011 | Lane et al. |
| 8,088,158 B2 | 1/2012 | Brodeur |
| 8,088,404 B2 | 1/2012 | Udipi et al. |
| 8,092,520 B2 | 1/2012 | Quadri |
| 8,100,964 B2 | 1/2012 | Spence |
| 8,105,375 B2 | 1/2012 | Navia et al. |
| 8,105,377 B2 | 1/2012 | Liddicoat |
| 8,109,995 B2 | 2/2012 | Paniagua et al. |
| 8,109,996 B2 | 2/2012 | Stacchino et al. |
| 8,114,154 B2 | 2/2012 | Righini et al. |
| 8,118,866 B2 | 2/2012 | Herrmann et al. |
| 8,119,704 B2 | 2/2012 | Wang et al. |
| 8,123,801 B2 | 2/2012 | Milo |
| 8,128,681 B2 | 3/2012 | Shoemaker et al. |
| 8,128,688 B2 | 3/2012 | Ding et al. |
| 8,136,218 B2 | 3/2012 | Millwee et al. |
| 8,137,398 B2 | 3/2012 | Tuval et al. |
| 8,137,687 B2 | 3/2012 | Chen et al. |
| 8,142,492 B2 | 3/2012 | Forster et al. |
| 8,142,494 B2 | 3/2012 | Rahdert et al. |
| 8,147,504 B2 | 4/2012 | Ino et al. |
| 8,155,754 B2 | 4/2012 | Nygren et al. |
| 8,157,852 B2 | 4/2012 | Bloom et al. |
| 8,157,853 B2 | 4/2012 | Laske et al. |
| 8,158,187 B2 | 4/2012 | Chen et al. |
| 8,163,014 B2 | 4/2012 | Lane et al. |
| 8,167,926 B2 | 5/2012 | Hartley et al. |
| 8,167,932 B2 | 5/2012 | Bourang et al. |
| 8,167,934 B2 | 5/2012 | Styrc et al. |
| 8,168,275 B2 | 5/2012 | Lee et al. |
| 8,170,645 B2 | 5/2012 | Solar et al. |
| 8,177,799 B2 | 5/2012 | Orban, III |
| 8,177,836 B2 | 5/2012 | Lee et al. |
| 8,180,428 B2 | 5/2012 | Kaiser et al. |
| 8,182,528 B2 | 5/2012 | Salahieh et al. |
| 8,182,530 B2 | 5/2012 | Huber et al. |
| 8,182,829 B2 | 5/2012 | Kleiner et al. |
| 8,187,851 B2 | 5/2012 | Shah et al. |
| 8,195,293 B2 | 6/2012 | Limousin et al. |
| 8,202,529 B2 | 6/2012 | Hossainy et al. |
| 8,211,169 B2 | 7/2012 | Lane et al. |
| 8,216,261 B2 | 7/2012 | Solem et al. |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,482 B2 | 7/2012 | Cottone et al. |
| 8,221,493 B2 | 7/2012 | Bailey et al. |
| 8,226,710 B2 | 7/2012 | Nguyen et al. |
| 8,231,930 B2 | 7/2012 | Castro et al. |
| D665,079 S | 8/2012 | Zago |
| D665,080 S | 8/2012 | Zago |
| 8,236,045 B2 | 8/2012 | Benichou et al. |
| 8,236,241 B2 | 8/2012 | Carpentier et al. |
| 8,241,274 B2 | 8/2012 | Keogh et al. |
| 8,246,675 B2 | 8/2012 | Zegdi |
| 8,246,677 B2 | 8/2012 | Ryan |
| 8,246,678 B2 | 8/2012 | Haug et al. |
| 8,252,051 B2 | 8/2012 | Chau et al. |
| 8,252,052 B2 | 8/2012 | Salahieh et al. |
| 8,257,724 B2 | 9/2012 | Cromack et al. |
| 8,257,725 B2 | 9/2012 | Cromack et al. |
| 8,262,724 B2 | 9/2012 | Seguin et al. |
| 8,273,118 B2 | 9/2012 | Bergin |
| 8,273,120 B2 | 9/2012 | Dolan |
| 8,276,533 B2 | 10/2012 | Chambers et al. |
| 8,287,584 B2 | 10/2012 | Salahieh et al. |
| 8,287,591 B2 | 10/2012 | Keidar et al. |
| 8,303,653 B2 | 11/2012 | Bonhoeffer et al. |
| 8,308,798 B2 | 11/2012 | Pintor et al. |
| 8,313,520 B2 | 11/2012 | Barbut et al. |
| 8,313,525 B2 | 11/2012 | Tuval et al. |
| 8,317,854 B1 | 11/2012 | Ryan et al. |
| 8,323,335 B2 | 12/2012 | Rowe et al. |
| 8,323,336 B2 | 12/2012 | Hill et al. |
| 8,337,541 B2 | 12/2012 | Quadri et al. |
| 8,348,995 B2 | 1/2013 | Tuval et al. |

(56) References Cited

U.S. PATENT DOCUMENTS

| | | |
|---|---|---|
| 8,349,001 B2 | 1/2013 | Mensah et al. |
| 8,349,003 B2 | 1/2013 | Shu et al. |
| 8,353,921 B2 | 1/2013 | Schaller et al. |
| 8,353,948 B2 | 1/2013 | Besselink et al. |
| 8,353,953 B2 | 1/2013 | Giannetti et al. |
| 8,357,387 B2 | 1/2013 | Dove et al. |
| 8,361,137 B2 | 1/2013 | Perouse |
| 8,361,537 B2 | 1/2013 | Shanley |
| 8,366,769 B2 | 2/2013 | Huynh et al. |
| 8,377,116 B2 | 2/2013 | Hsu et al. |
| 8,377,499 B2 | 2/2013 | Kleiner et al. |
| 8,382,816 B2 | 2/2013 | Pollock et al. |
| RE44,075 E | 3/2013 | Williamson et al. |
| 8,398,707 B2 | 3/2013 | Bergin |
| 8,398,708 B2 | 3/2013 | Meiri et al. |
| 8,403,983 B2 | 3/2013 | Quadri et al. |
| 8,408,214 B2 | 4/2013 | Spenser |
| 8,409,274 B2 | 4/2013 | Li et al. |
| 8,414,635 B2 | 4/2013 | Hyodoh et al. |
| 8,414,643 B2 | 4/2013 | Tuval et al. |
| 8,414,644 B2 | 4/2013 | Quadri et al. |
| 8,414,645 B2 | 4/2013 | Dwork et al. |
| 8,430,902 B2 | 4/2013 | Bergheim |
| 8,430,927 B2 | 4/2013 | Bonhoeffer |
| 8,444,689 B2 | 5/2013 | Zhang |
| 8,449,466 B2 | 5/2013 | Duhay et al. |
| 8,449,599 B2 | 5/2013 | Chau et al. |
| 8,449,625 B2 | 5/2013 | Campbell et al. |
| 8,454,684 B2 | 6/2013 | Bergin et al. |
| 8,454,685 B2 | 6/2013 | Hariton et al. |
| 8,460,335 B2 | 6/2013 | Carpenter |
| 8,460,365 B2 | 6/2013 | Haverkost et al. |
| 8,460,366 B2 | 6/2013 | Rowe et al. |
| 8,460,370 B2 | 6/2013 | Zakay et al. |
| 8,460,373 B2 | 6/2013 | Fogarty et al. |
| 8,470,023 B2 | 6/2013 | Eidenschink et al. |
| 8,470,024 B2 | 6/2013 | Ghione et al. |
| 8,475,521 B2 | 7/2013 | Suri et al. |
| 8,475,522 B2 | 7/2013 | Jimenez et al. |
| 8,475,523 B2 | 7/2013 | Duffy |
| 8,479,380 B2 | 7/2013 | Malewicz et al. |
| 8,480,730 B2 | 7/2013 | Maurer et al. |
| 8,480,731 B2 | 7/2013 | Elizondo et al. |
| 8,486,137 B2 | 7/2013 | Suri et al. |
| 8,491,650 B2 | 7/2013 | Wiemeyer et al. |
| 8,500,688 B2 | 8/2013 | Engel et al. |
| 8,500,755 B2 | 8/2013 | Ino et al. |
| 8,500,798 B2 | 8/2013 | Rowe et al. |
| 8,500,801 B2 | 8/2013 | Eberhardt et al. |
| 8,500,802 B2 | 8/2013 | Lane et al. |
| 8,506,620 B2 | 8/2013 | Ryan |
| 8,506,625 B2 | 8/2013 | Johnson |
| 8,511,244 B2 | 8/2013 | Holecek et al. |
| 8,512,397 B2 | 8/2013 | Rolando et al. |
| 8,512,398 B2 | 8/2013 | Alkhatib |
| 8,512,399 B2 | 8/2013 | Lafontaine |
| 8,512,401 B2 | 8/2013 | Murray, III et al. |
| 8,518,106 B2 | 8/2013 | Duffy et al. |
| 8,518,108 B2 | 8/2013 | Huynh et al. |
| 8,529,621 B2 | 9/2013 | Alfieri et al. |
| 8,535,368 B2 | 9/2013 | Headley et al. |
| 8,539,662 B2 | 9/2013 | Stacchino et al. |
| 8,545,742 B2 | 10/2013 | Gada et al. |
| 8,551,162 B2 | 10/2013 | Fogarty et al. |
| 8,562,663 B2 | 10/2013 | Mearns et al. |
| 8,562,672 B2 | 10/2013 | Bonhoeffer et al. |
| 8,562,673 B2 | 10/2013 | Yeung et al. |
| 8,565,872 B2 | 10/2013 | Pederson |
| 8,568,472 B2 | 10/2013 | Marchand et al. |
| 8,579,964 B2 | 11/2013 | Lane et al. |
| 8,579,965 B2 | 11/2013 | Bonhoeffer et al. |
| 8,584,849 B2 | 11/2013 | McCaffrey |
| 8,585,749 B2 | 11/2013 | Shelso |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,591,574 B2 | 11/2013 | Lambrecht et al. |
| 8,597,348 B2 | 12/2013 | Rowe et al. |
| 8,603,154 B2 | 12/2013 | Strauss et al. |
| 8,603,160 B2 | 12/2013 | Salahieh et al. |
| 8,603,161 B2 | 12/2013 | Drews et al. |
| 8,608,648 B2 | 12/2013 | Banik et al. |
| 8,617,236 B2 | 12/2013 | Paul et al. |
| 8,623,074 B2 | 1/2014 | Ryan |
| 8,623,080 B2 | 1/2014 | Fogarty et al. |
| 8,628,566 B2 | 1/2014 | Eberhardt et al. |
| 8,632,586 B2 | 1/2014 | Spenser et al. |
| 8,632,608 B2 | 1/2014 | Carpentier et al. |
| 8,640,521 B2 | 2/2014 | Righini et al. |
| 8,641,639 B2 | 2/2014 | Manstrom et al. |
| 8,647,381 B2 | 2/2014 | Essinger et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,653,632 B2 | 2/2014 | Pederson et al. |
| 8,663,318 B2 | 3/2014 | Ho |
| 8,663,319 B2 | 3/2014 | Ho |
| 8,668,730 B2 | 3/2014 | McGuckin, Jr. et al. |
| 8,668,733 B2 | 3/2014 | Salahieh et al. |
| 8,672,992 B2 | 3/2014 | Orr |
| 8,672,997 B2 | 3/2014 | Drasler et al. |
| 8,672,998 B2 | 3/2014 | Lichtenstein et al. |
| 8,672,999 B2 | 3/2014 | Cali et al. |
| 8,673,000 B2 | 3/2014 | Tabor et al. |
| 8,679,174 B2 | 3/2014 | Ottma et al. |
| 8,679,404 B2 | 3/2014 | Liburd et al. |
| 8,685,083 B2 | 4/2014 | Perier et al. |
| 8,685,086 B2 | 4/2014 | Navia et al. |
| 8,690,787 B2 | 4/2014 | Blomqvist et al. |
| 8,690,936 B2 | 4/2014 | Nguyen et al. |
| 8,696,742 B2 | 4/2014 | Pintor et al. |
| 8,707,957 B2 | 4/2014 | Callister et al. |
| 8,715,207 B2 | 5/2014 | Righini et al. |
| 8,715,337 B2 | 5/2014 | Chuter et al. |
| 8,715,343 B2 | 5/2014 | Navia et al. |
| 8,721,707 B2 | 5/2014 | Boucher et al. |
| 8,721,708 B2 | 5/2014 | Sequin et al. |
| 8,721,713 B2 | 5/2014 | Tower et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,731,658 B2 | 5/2014 | Hampton et al. |
| 8,734,484 B2 | 5/2014 | Ahlberg et al. |
| 8,740,930 B2 | 6/2014 | Goodwin |
| 8,740,974 B2 | 6/2014 | Lambrecht et al. |
| 8,740,975 B2 | 6/2014 | Yang et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,753,384 B2 | 6/2014 | Leanna |
| 8,758,432 B2 | 6/2014 | Solem et al. |
| 8,764,814 B2 | 7/2014 | Solem |
| 8,764,820 B2 | 7/2014 | Dehdashtian et al. |
| 8,771,302 B2 | 7/2014 | Woolfson et al. |
| 8,771,344 B2 | 7/2014 | Tran et al. |
| 8,771,345 B2 | 7/2014 | Tuval et al. |
| 8,771,346 B2 | 7/2014 | Tuval et al. |
| 8,777,975 B2 | 7/2014 | Kashkarov et al. |
| 8,778,018 B2 | 7/2014 | Iobbi |
| 8,784,478 B2 | 7/2014 | Tuval et al. |
| 8,784,480 B2 | 7/2014 | Taylor et al. |
| 8,784,481 B2 | 7/2014 | Alkhatib et al. |
| 8,790,387 B2 | 7/2014 | Nguyen et al. |
| 8,790,395 B2 | 7/2014 | Straubinger et al. |
| 8,790,396 B2 | 7/2014 | Bergheim et al. |
| 8,791,171 B2 | 7/2014 | Pacetti et al. |
| 8,795,356 B2 | 8/2014 | Quadri et al. |
| 8,801,776 B2 | 8/2014 | House et al. |
| 8,808,366 B2 | 8/2014 | Braido et al. |
| 8,808,370 B2 | 8/2014 | Nitzan et al. |
| 8,821,569 B2 | 9/2014 | Gurskis et al. |
| 8,821,570 B2 | 9/2014 | Dumontelle et al. |
| 8,828,078 B2 | 9/2014 | Salahieh et al. |

(56) References Cited

U.S. PATENT DOCUMENTS

| | | |
|---|---|---|
| 8,828,079 B2 | 9/2014 | Thielen et al. |
| 8,834,561 B2 | 9/2014 | Figulla et al. |
| 8,834,564 B2 | 9/2014 | Tuval et al. |
| 8,840,661 B2 | 9/2014 | Manasse |
| 8,845,718 B2 | 9/2014 | Tuval et al. |
| 8,845,720 B2 | 9/2014 | Conklin |
| 8,852,267 B2 | 10/2014 | Cattaneo |
| 8,858,620 B2 | 10/2014 | Salahieh et al. |
| 8,858,621 B2 | 10/2014 | Oba et al. |
| 8,870,936 B2 | 10/2014 | Rowe |
| 8,870,947 B2 | 10/2014 | Shaw |
| 8,870,948 B1 | 10/2014 | Erzberger et al. |
| 8,876,712 B2 | 11/2014 | Yee et al. |
| 8,876,883 B2 | 11/2014 | Rust |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,882,831 B2 | 11/2014 | Alkhatib |
| 8,894,702 B2 | 11/2014 | Quadri et al. |
| 8,894,703 B2 | 11/2014 | Salahieh et al. |
| 8,906,081 B2 | 12/2014 | Cully et al. |
| 8,911,455 B2 | 12/2014 | Quadri et al. |
| 8,911,844 B2 | 12/2014 | Ford |
| 8,926,688 B2 | 1/2015 | Burkart et al. |
| 8,926,693 B2 | 1/2015 | Duffy et al. |
| 8,932,349 B2 | 1/2015 | Jenson et al. |
| 8,940,887 B2 | 1/2015 | Chatterton et al. |
| 8,945,208 B2 | 2/2015 | Jimenez et al. |
| 8,945,209 B2 | 2/2015 | Bonyuet et al. |
| 8,945,210 B2 | 2/2015 | Cartledge et al. |
| 8,951,280 B2 | 2/2015 | Cohn et al. |
| 8,951,299 B2 | 2/2015 | Paul et al. |
| 8,961,583 B2 | 2/2015 | Hojeibane et al. |
| 8,961,589 B2 | 2/2015 | Kleiner et al. |
| 8,961,593 B2 | 2/2015 | Bonhoeffer et al. |
| 8,961,595 B2 | 2/2015 | Alkhatib |
| 8,968,393 B2 | 3/2015 | Rothstein |
| 8,968,395 B2 | 3/2015 | Hauser et al. |
| 8,974,524 B2 | 3/2015 | Yeung et al. |
| 8,979,922 B2 | 3/2015 | Thambar et al. |
| 8,986,372 B2 | 3/2015 | Murry, III et al. |
| 8,986,713 B2 | 3/2015 | Cleek et al. |
| 8,992,608 B2 | 3/2015 | Salahieh et al. |
| 8,998,978 B2 | 4/2015 | Wang |
| 8,998,979 B2 | 4/2015 | Seguin et al. |
| 8,998,980 B2 | 4/2015 | Shipley et al. |
| 8,998,981 B2 | 4/2015 | Tuval et al. |
| 8,999,369 B2 | 4/2015 | Gale et al. |
| 9,005,273 B2 | 4/2015 | Salahieh et al. |
| 9,005,277 B2 | 4/2015 | Pintor et al. |
| 9,011,521 B2 | 4/2015 | Haug et al. |
| 9,011,523 B2 | 4/2015 | Seguin |
| 9,011,524 B2 | 4/2015 | Eberhardt |
| 9,011,528 B2 | 4/2015 | Ryan et al. |
| 9,023,100 B2 | 5/2015 | Quadri et al. |
| 9,028,545 B2 | 5/2015 | Taylor |
| 9,029,418 B2 | 5/2015 | Dove et al. |
| 9,034,033 B2 | 5/2015 | McLean et al. |
| 9,055,937 B2 | 6/2015 | Rowe et al. |
| 9,078,749 B2 | 7/2015 | Lutter et al. |
| 9,078,751 B2 | 7/2015 | Naor |
| 9,084,676 B2 | 7/2015 | Chau et al. |
| 9,125,738 B2 | 9/2015 | Figulla et al. |
| 9,138,312 B2 | 9/2015 | Tuval et al. |
| 9,161,834 B2 | 10/2015 | Taylor et al. |
| D755,384 S | 5/2016 | Pesce et al. |
| 9,333,074 B2 | 5/2016 | Quadri et al. |
| 2001/0007956 A1 | 7/2001 | Letac et al. |
| 2001/0021872 A1 | 9/2001 | Bailey et al. |
| 2001/0047180 A1 | 11/2001 | Grudem et al. |
| 2001/0047200 A1 | 11/2001 | White et al. |
| 2002/0016623 A1 | 2/2002 | Kula et al. |
| 2002/0022853 A1 | 2/2002 | Swanson et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0055772 A1 | 5/2002 | McGuckin et al. |
| 2002/0111619 A1 | 8/2002 | Keast et al. |
| 2002/0183827 A1 | 12/2002 | Derus et al. |
| 2003/0040792 A1 | 2/2003 | Gabbay |
| 2003/0105517 A1 | 6/2003 | White et al. |
| 2003/0114913 A1 | 6/2003 | Spenser et al. |
| 2003/0120263 A1 | 6/2003 | Ouriel et al. |
| 2003/0120330 A1 | 6/2003 | Ouriel et al. |
| 2003/0120333 A1 | 6/2003 | Ouriel et al. |
| 2003/0125797 A1 | 7/2003 | Chobotov et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0039436 A1 | 2/2004 | Spenser et al. |
| 2004/0087900 A1 | 5/2004 | Thompson et al. |
| 2004/0093058 A1 | 5/2004 | Cottone et al. |
| 2004/0093060 A1 | 5/2004 | Seguin et al. |
| 2004/0102842 A1 | 5/2004 | Jansen |
| 2004/0117009 A1 | 6/2004 | Cali et al. |
| 2004/0133273 A1 | 7/2004 | Cox |
| 2004/0181238 A1 | 9/2004 | Zarbatany et al. |
| 2004/0186561 A1 | 9/2004 | McGuckin et al. |
| 2004/0193261 A1 | 9/2004 | Berreklouw |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2004/0243230 A1 | 12/2004 | Navia et al. |
| 2004/0249433 A1 | 12/2004 | Freitag |
| 2004/0260390 A1 | 12/2004 | Sarac et al. |
| 2005/0033398 A1 | 2/2005 | Seguin |
| 2005/0038470 A1 | 2/2005 | Van Der Burg et al. |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0125020 A1 | 6/2005 | Meade et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137690 A1 | 6/2005 | Salahieh et al. |
| 2005/0137691 A1 | 6/2005 | Salahieh et al. |
| 2005/0137693 A1 | 6/2005 | Haug et al. |
| 2005/0137695 A1 | 6/2005 | Salahieh et al. |
| 2005/0137701 A1 | 6/2005 | Salahieh et al. |
| 2005/0154444 A1 | 7/2005 | Quadri |
| 2005/0159811 A1 | 7/2005 | Lane |
| 2005/0182483 A1 | 8/2005 | Osborne et al. |
| 2005/0182486 A1 | 8/2005 | Gabbay |
| 2005/0203616 A1 | 9/2005 | Cribier |
| 2005/0216079 A1 | 9/2005 | MaCoviak |
| 2005/0234546 A1 | 10/2005 | Nugent et al. |
| 2005/0283231 A1 | 12/2005 | Haug et al. |
| 2006/0020247 A1 | 1/2006 | Kagan et al. |
| 2006/0020327 A1 | 1/2006 | Lashinski et al. |
| 2006/0020334 A1 | 1/2006 | Lashinski et al. |
| 2006/0052802 A1 | 3/2006 | Sterman et al. |
| 2006/0052867 A1 | 3/2006 | Revuelta et al. |
| 2006/0058872 A1 | 3/2006 | Salahieh et al. |
| 2006/0064120 A1 | 3/2006 | Levine et al. |
| 2006/0095115 A1 | 5/2006 | Bladillah et al. |
| 2006/0106454 A1 | 5/2006 | Osborne et al. |
| 2006/0116625 A1 | 6/2006 | Renati et al. |
| 2006/0129235 A1 | 6/2006 | Seguin et al. |
| 2006/0149360 A1 | 7/2006 | Schwammenthal et al. |
| 2006/0161265 A1 | 7/2006 | Levine et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0224232 A1 | 10/2006 | Chobotov |
| 2006/0241745 A1 | 10/2006 | Solem |
| 2006/0253191 A1 | 11/2006 | Salahieh et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0287717 A1 | 12/2006 | Rowe et al. |

(56) References Cited

U.S. PATENT DOCUMENTS

| | | |
|---|---|---|
| 2006/0287719 A1 | 12/2006 | Rowe et al. |
| 2006/0293698 A1 | 12/2006 | Douk |
| 2006/0293745 A1 | 12/2006 | Carpentier et al. |
| 2007/0010876 A1 | 1/2007 | Salahieh et al. |
| 2007/0016286 A1 | 1/2007 | Herrmann et al. |
| 2007/0043435 A1 | 2/2007 | Seguin et al. |
| 2007/0050020 A1 | 3/2007 | Spence |
| 2007/0050021 A1 | 3/2007 | Johnson |
| 2007/0067016 A1 | 3/2007 | Jung |
| 2007/0100432 A1 | 5/2007 | Case et al. |
| 2007/0118206 A1 | 5/2007 | Colgan et al. |
| 2007/0118207 A1 | 5/2007 | Amplatz et al. |
| 2007/0129794 A1 | 6/2007 | Realyvasquez |
| 2007/0142906 A1 | 6/2007 | Figulla et al. |
| 2007/0162107 A1 | 7/2007 | Haug et al. |
| 2007/0185559 A1 | 8/2007 | Shelso |
| 2007/0213813 A1 | 9/2007 | Von Segesser et al. |
| 2007/0219620 A1 | 9/2007 | Eells et al. |
| 2007/0233228 A1 | 10/2007 | Eberhardt et al. |
| 2007/0250151 A1 | 10/2007 | Pereira |
| 2007/0255391 A1 | 11/2007 | Hojeibane et al. |
| 2007/0255394 A1 | 11/2007 | Ryan |
| 2007/0265656 A1 | 11/2007 | Amplatz et al. |
| 2007/0270932 A1 | 11/2007 | Headley et al. |
| 2007/0270937 A1 | 11/2007 | Leanna |
| 2007/0293940 A1 | 12/2007 | Schaeffer et al. |
| 2008/0009934 A1 | 1/2008 | Schneider et al. |
| 2008/0021546 A1 | 1/2008 | Patz et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0087581 A1 | 4/2008 | Eisenhut et al. |
| 2008/0097571 A1 | 4/2008 | Denison et al. |
| 2008/0114441 A1 | 5/2008 | Rust et al. |
| 2008/0125853 A1 | 5/2008 | Bailey et al. |
| 2008/0125859 A1 | 5/2008 | Salahieh et al. |
| 2008/0133003 A1 | 6/2008 | Seguin et al. |
| 2008/0140189 A1 | 6/2008 | Nguyen et al. |
| 2008/0147179 A1 | 6/2008 | Cai et al. |
| 2008/0147183 A1 | 6/2008 | Styrc |
| 2008/0154358 A1 | 6/2008 | Tansley et al. |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208307 A1 | 8/2008 | Ben-Muvhar et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0228201 A1 | 9/2008 | Zarbatany et al. |
| 2008/0228254 A1 | 9/2008 | Ryan |
| 2008/0243233 A1 | 10/2008 | Ben-Muvhar et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0262596 A1 | 10/2008 | Xiao |
| 2008/0262603 A1 | 10/2008 | Giaquinta et al. |
| 2008/0269878 A1 | 10/2008 | Iobbi |
| 2008/0275549 A1 | 11/2008 | Rowe |
| 2008/0288062 A1 | 11/2008 | Andrieu et al. |
| 2008/0319526 A1 | 12/2008 | Hill et al. |
| 2009/0005863 A1 | 1/2009 | Goetz et al. |
| 2009/0012602 A1 | 1/2009 | Quadri |
| 2009/0054976 A1 | 2/2009 | Tuval et al. |
| 2009/0062908 A1 | 3/2009 | Bonhoeffer et al. |
| 2009/0076531 A1 | 3/2009 | Richardson et al. |
| 2009/0076585 A1 | 3/2009 | Hendriksen et al. |
| 2009/0076598 A1 | 3/2009 | Salahieh et al. |
| 2009/0082844 A1 | 3/2009 | Zacharias et al. |
| 2009/0082847 A1 | 3/2009 | Zacharias et al. |
| 2009/0088832 A1 | 4/2009 | Chew et al. |
| 2009/0112309 A1 | 4/2009 | Jaramillo et al. |
| 2009/0118744 A1 | 5/2009 | Wells et al. |
| 2009/0118824 A1 | 5/2009 | Samkov |
| 2009/0118826 A1 | 5/2009 | Khaghani |
| 2009/0125096 A1 | 5/2009 | Chu et al. |
| 2009/0132035 A1 | 5/2009 | Roth et al. |
| 2009/0138079 A1 | 5/2009 | Tuval et al. |
| 2009/0149946 A1 | 6/2009 | Dixon |
| 2009/0157175 A1 | 6/2009 | Benichou |
| 2009/0163934 A1 | 6/2009 | Raschdorf, Jr. et al. |
| 2009/0171438 A1 | 7/2009 | Chuter et al. |
| 2009/0171456 A1 | 7/2009 | Kveen et al. |
| 2009/0177262 A1 | 7/2009 | Oberti et al. |
| 2009/0182407 A1 | 7/2009 | Leanna et al. |
| 2009/0182413 A1 | 7/2009 | Burkart et al. |
| 2009/0188964 A1 | 7/2009 | Orlov |
| 2009/0192601 A1 | 7/2009 | Rafiee et al. |
| 2009/0216314 A1 | 8/2009 | Quadri |
| 2009/0216317 A1 | 8/2009 | Cromack et al. |
| 2009/0222076 A1 | 9/2009 | Figulla et al. |
| 2009/0227992 A1 | 9/2009 | Nir et al. |
| 2009/0234443 A1 | 9/2009 | Ottma et al. |
| 2009/0248132 A1 | 10/2009 | Bloom et al. |
| 2009/0248133 A1 | 10/2009 | Bloom et al. |
| 2009/0258958 A1 | 10/2009 | Ford |
| 2009/0264989 A1 | 10/2009 | Bonhoeffer et al. |
| 2009/0264997 A1 | 10/2009 | Salahieh et al. |
| 2009/0270972 A1 | 10/2009 | Lane |
| 2009/0276040 A1 | 11/2009 | Rowe et al. |
| 2009/0281618 A1 | 11/2009 | Hill et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2009/0318871 A1 | 12/2009 | Zarbatany et al. |
| 2010/0004740 A1 | 1/2010 | Seguin et al. |
| 2010/0036479 A1 | 2/2010 | Hill et al. |
| 2010/0049306 A1 | 2/2010 | House et al. |
| 2010/0082089 A1 | 4/2010 | Quadri et al. |
| 2010/0082094 A1 | 4/2010 | Quadri et al. |
| 2010/0094411 A1 | 4/2010 | Tuval et al. |
| 2010/0114299 A1 | 5/2010 | Ben et al. |
| 2010/0114305 A1 | 5/2010 | Kang et al. |
| 2010/0121461 A1 | 5/2010 | Sobrino-Serrano et al. |
| 2010/0161027 A1 | 6/2010 | Orr |
| 2010/0179633 A1 | 7/2010 | Solem et al. |
| 2010/0179647 A1 | 7/2010 | Carpenter et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249908 A1 | 9/2010 | Chau et al. |
| 2010/0256723 A1 | 10/2010 | Murray |
| 2010/0262157 A1 | 10/2010 | Silver et al. |
| 2010/0274345 A1 | 10/2010 | Rust |
| 2010/0280606 A1 | 11/2010 | Naor |
| 2010/0298931 A1 | 11/2010 | Quadri et al. |
| 2010/0305685 A1 | 12/2010 | Millwee et al. |
| 2010/0312333 A1 | 12/2010 | Navia et al. |
| 2011/0004296 A1 | 1/2011 | Lutter et al. |
| 2011/0015731 A1 | 1/2011 | Carpentier et al. |
| 2011/0022157 A1 | 1/2011 | Essinger et al. |
| 2011/0022165 A1 | 1/2011 | Oba et al. |
| 2011/0029067 A1 | 2/2011 | McGuckin, Jr. et al. |
| 2011/0137397 A1 | 6/2011 | Chau et al. |
| 2011/0166644 A1 | 7/2011 | Keeble et al. |
| 2011/0178597 A9 | 7/2011 | Navia et al. |
| 2011/0208290 A1* | 8/2011 | Straubinger .......... A61F 2/2418 623/1.15 |
| 2011/0208297 A1 | 8/2011 | Tuval et al. |
| 2011/0218619 A1 | 9/2011 | Benichou et al. |
| 2011/0224785 A1 | 9/2011 | Hacohen |
| 2011/0264196 A1 | 10/2011 | Savage et al. |
| 2011/0282438 A1 | 11/2011 | Drews et al. |
| 2011/0301704 A1 | 12/2011 | Alfieri et al. |
| 2011/0313515 A1 | 12/2011 | Quadri et al. |
| 2011/0319981 A1 | 12/2011 | Hill et al. |
| 2011/0319989 A1* | 12/2011 | Lane ................... A61F 2/2418 623/2.11 |
| 2012/0012487 A1 | 1/2012 | Tian et al. |

(56) References Cited

U.S. PATENT DOCUMENTS

| | | |
|---|---|---|
| 2012/0016342 A1 | 1/2012 | Brecker |
| 2012/0016411 A1 | 1/2012 | Tuval |
| 2012/0022605 A1 | 1/2012 | Jahns et al. |
| 2012/0022633 A1* | 1/2012 | Olson .................. A61F 2/2418 623/1.11 |
| 2012/0022639 A1 | 1/2012 | Hacohen et al. |
| 2012/0022640 A1* | 1/2012 | Gross .................. A61B 17/068 623/2.11 |
| 2012/0022642 A1 | 1/2012 | Haug et al. |
| 2012/0029627 A1 | 2/2012 | Salahieh et al. |
| 2012/0035703 A1 | 2/2012 | Lutter et al. |
| 2012/0035713 A1 | 2/2012 | Lutter et al. |
| 2012/0041550 A1 | 2/2012 | Salahieh et al. |
| 2012/0041551 A1 | 2/2012 | Spenser et al. |
| 2012/0059452 A1 | 3/2012 | Boucher et al. |
| 2012/0059454 A1 | 3/2012 | Millwee et al. |
| 2012/0078353 A1 | 3/2012 | Quadri et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0179051 A1 | 7/2012 | Pfeiffer et al. |
| 2012/0179239 A1 | 7/2012 | Quadri |
| 2012/0179243 A1 | 7/2012 | Yang et al. |
| 2012/0185033 A1 | 7/2012 | Ryan |
| 2012/0215303 A1 | 8/2012 | Quadri et al. |
| 2012/0259405 A1 | 10/2012 | Weber et al. |
| 2012/0259409 A1 | 10/2012 | Nguyen et al. |
| 2012/0271398 A1 | 10/2012 | Essinger et al. |
| 2012/0283820 A1 | 11/2012 | Tseng et al. |
| 2012/0283824 A1 | 11/2012 | Lutter et al. |
| 2012/0290062 A1 | 11/2012 | McNamara et al. |
| 2012/0296418 A1 | 11/2012 | Bonyuet et al. |
| 2012/0303116 A1 | 11/2012 | Gorman, III et al. |
| 2012/0310328 A1 | 12/2012 | Olson et al. |
| 2012/0323316 A1 | 12/2012 | Chau et al. |
| 2012/0330409 A1 | 12/2012 | Haug et al. |
| 2013/0006294 A1 | 1/2013 | Kashkarov et al. |
| 2013/0018458 A1 | 1/2013 | Yohanan et al. |
| 2013/0030418 A1 | 1/2013 | Taft et al. |
| 2013/0030523 A1 | 1/2013 | Padala et al. |
| 2013/0046378 A1 | 2/2013 | Millwee et al. |
| 2013/0053949 A1 | 2/2013 | Pintor et al. |
| 2013/0053950 A1 | 2/2013 | Rowe et al. |
| 2013/0095264 A1 | 4/2013 | Sowinski et al. |
| 2013/0096671 A1 | 4/2013 | Iobbi |
| 2013/0110226 A1 | 5/2013 | Gurskis |
| 2013/0110227 A1 | 5/2013 | Quadri et al. |
| 2013/0110230 A1 | 5/2013 | Solem |
| 2013/0116777 A1 | 5/2013 | Pintor et al. |
| 2013/0131788 A1 | 5/2013 | Quadri et al. |
| 2013/0131793 A1 | 5/2013 | Quadri et al. |
| 2013/0138203 A1 | 5/2013 | Quadri et al. |
| 2013/0138207 A1 | 5/2013 | Quadri et al. |
| 2013/0144375 A1 | 6/2013 | Giasolli et al. |
| 2013/0144378 A1 | 6/2013 | Quadri et al. |
| 2013/0144380 A1 | 6/2013 | Quadri et al. |
| 2013/0144381 A1 | 6/2013 | Quadri et al. |
| 2013/0150956 A1 | 6/2013 | Yohanan et al. |
| 2013/0166024 A1 | 6/2013 | Drews et al. |
| 2013/0172983 A1 | 7/2013 | Clerc et al. |
| 2013/0184813 A1 | 7/2013 | Quadri et al. |
| 2013/0184814 A1 | 7/2013 | Huynh et al. |
| 2013/0211508 A1 | 8/2013 | Lane et al. |
| 2013/0236889 A1 | 9/2013 | Kishimoto et al. |
| 2013/0238087 A1 | 9/2013 | Taylor |
| 2013/0245615 A1 | 9/2013 | Koltz |
| 2013/0245736 A1 | 9/2013 | Alexander et al. |
| 2013/0253635 A1 | 9/2013 | Straubinger et al. |
| 2013/0253637 A1 | 9/2013 | Wang et al. |
| 2013/0253639 A1 | 9/2013 | Alkhatib |
| 2013/0253641 A1 | 9/2013 | Lattouf |
| 2013/0253642 A1 | 9/2013 | Brecker |
| 2013/0261737 A1 | 10/2013 | Costello |
| 2013/0261738 A1 | 10/2013 | Clague et al. |
| 2013/0268069 A1 | 10/2013 | Zakai et al. |
| 2013/0289695 A1 | 10/2013 | Tian et al. |
| 2013/0304200 A1 | 11/2013 | McLean et al. |
| 2013/0310928 A1 | 11/2013 | Morriss et al. |
| 2013/0325098 A1 | 12/2013 | Desai et al. |
| 2013/0325121 A1 | 12/2013 | Whatley et al. |
| 2013/0331714 A1 | 12/2013 | Manstrom et al. |
| 2013/0338764 A1 | 12/2013 | Thornton et al. |
| 2013/0338765 A1 | 12/2013 | Braido et al. |
| 2013/0345786 A1 | 12/2013 | Behan |
| 2013/0345803 A1 | 12/2013 | Bergheim, III |
| 2014/0018912 A1 | 1/2014 | Delaloye et al. |
| 2014/0031930 A1 | 1/2014 | Keidar et al. |
| 2014/0039611 A1 | 2/2014 | Lane et al. |
| 2014/0039612 A1 | 2/2014 | Dolan |
| 2014/0039614 A1 | 2/2014 | Delaloye et al. |
| 2014/0044689 A1 | 2/2014 | Liu et al. |
| 2014/0046219 A1 | 2/2014 | Sauter et al. |
| 2014/0046427 A1 | 2/2014 | Michalak |
| 2014/0052237 A1 | 2/2014 | Lane et al. |
| 2014/0052242 A1 | 2/2014 | Revuelta et al. |
| 2014/0081393 A1 | 3/2014 | Hasenkam et al. |
| 2014/0086934 A1 | 3/2014 | Shams |
| 2014/0088685 A1 | 3/2014 | Yevzlin et al. |
| 2014/0088694 A1 | 3/2014 | Rowe et al. |
| 2014/0100420 A1 | 4/2014 | Mortier et al. |
| 2014/0100651 A1 | 4/2014 | Kheradvar et al. |
| 2014/0100653 A1 | 4/2014 | Savage et al. |
| 2014/0107761 A1 | 4/2014 | Gale et al. |
| 2014/0142694 A1 | 5/2014 | Tabor et al. |
| 2014/0155997 A1* | 6/2014 | Braido .................. A61F 2/2418 623/2.37 |
| 2014/0163668 A1 | 6/2014 | Rafiee |
| 2014/0172085 A1 | 6/2014 | Quadri et al. |
| 2014/0172086 A1 | 6/2014 | Quadri et al. |
| 2014/0186417 A1 | 7/2014 | Trollsas et al. |
| 2014/0194978 A1 | 7/2014 | Seguin et al. |
| 2014/0194981 A1 | 7/2014 | Menk et al. |
| 2014/0194982 A1 | 7/2014 | Kovalsky et al. |
| 2014/0194983 A1 | 7/2014 | Kovalsky et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0215791 A1 | 8/2014 | Soundararajan et al. |
| 2014/0221823 A1 | 8/2014 | Keogh et al. |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0230515 A1 | 8/2014 | Tuval et al. |
| 2014/0236288 A1 | 8/2014 | Lambrecht et al. |
| 2014/0243966 A1 | 8/2014 | Garde et al. |
| 2014/0249622 A1 | 9/2014 | Carmi et al. |
| 2014/0256035 A1 | 9/2014 | Strasly et al. |
| 2014/0257475 A1 | 9/2014 | Gross et al. |
| 2014/0257476 A1 | 9/2014 | Montorfano et al. |
| 2014/0277390 A1 | 9/2014 | Ratz et al. |
| 2014/0277402 A1 | 9/2014 | Essinger et al. |
| 2014/0277422 A1 | 9/2014 | Ratz et al. |
| 2014/0277423 A1 | 9/2014 | Alkhatib et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309731 A1 | 10/2014 | Quadri et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0336754 A1 | 11/2014 | Gurskis et al. |
| 2014/0350565 A1 | 11/2014 | Yacoby et al. |
| 2014/0350666 A1 | 11/2014 | Righini |
| 2014/0356519 A1 | 12/2014 | Hossainy et al. |
| 2014/0358223 A1 | 12/2014 | Rafiee et al. |
| 2014/0364404 A1 | 12/2014 | Cleek et al. |
| 2014/0364944 A1 | 12/2014 | Lutter et al. |
| 2014/0370071 A1 | 12/2014 | Chen et al. |
| 2014/0371845 A1 | 12/2014 | Tuval et al. |
| 2014/0371847 A1 | 12/2014 | Madrid et al. |

(56) References Cited

U.S. PATENT DOCUMENTS

| | | |
|---|---|---|
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0032153 A1 | 1/2015 | Quadri et al. |
| 2015/0045881 A1 | 2/2015 | Lim |
| 2015/0066140 A1 | 3/2015 | Quadri et al. |
| 2015/0081009 A1 | 3/2015 | Quadri et al. |
| 2015/0086603 A1 | 3/2015 | Hossainy et al. |
| 2015/0088252 A1 | 3/2015 | Jenson et al. |
| 2015/0105856 A1 | 4/2015 | Rowe et al. |
| 2015/0142103 A1* | 5/2015 | Vidlund ............... A61F 2/2418 623/2.17 |
| 2015/0148731 A1 | 5/2015 | McNamara et al. |
| 2015/0157458 A1 | 6/2015 | Thambar et al. |
| 2015/0209137 A1 | 7/2015 | Quadri et al. |
| 2015/0209141 A1 | 7/2015 | Braido et al. |
| 2015/0216653 A1 | 8/2015 | Freudenthal |
| 2015/0238315 A1 | 8/2015 | Rabito et al. |
| 2015/0305864 A1 | 10/2015 | Quadri et al. |
| 2015/0328000 A1 | 11/2015 | Ratz et al. |
| 2015/0342736 A1 | 12/2015 | Rabito et al. |
| 2016/0038281 A1 | 2/2016 | Delaloye et al. |

FOREIGN PATENT DOCUMENTS

| | | |
|---|---|---|
| CA | 2900571 A1 | 9/2014 |
| CN | 104203158 A | 12/2014 |
| CN | 109259895 A | 1/2019 |
| DE | 3128704 A1 | 2/1983 |
| DE | 102006052564 B3 | 12/2007 |
| EP | 0657147 A2 | 6/1995 |
| EP | 1255510 B1 | 4/2007 |
| EP | 1472996 B1 | 9/2009 |
| EP | 2967860 A1 | 1/2016 |
| GB | 1264471 A | 2/1972 |
| GB | 1315844 A | 5/1973 |
| GB | 2245495 A | 1/1992 |
| GB | 2398245 A | 8/2004 |
| JP | 2002540889 A | 12/2002 |
| JP | 2008541865 A | 11/2008 |
| WO | WO-9749355 A1 | 12/1997 |
| WO | WO-0053104 A1 | 9/2000 |
| WO | WO-0061034 A1 | 10/2000 |
| WO | WO-0135861 A1 | 5/2001 |
| WO | WO-0135870 A1 | 5/2001 |
| WO | WO-0172239 A2 | 10/2001 |
| WO | WO-0236048 A1 | 5/2002 |
| WO | WO-03028522 A2 | 4/2003 |
| WO | WO-03092554 A1 | 11/2003 |
| WO | WO-2004014257 A1 | 2/2004 |
| WO | WO-2004014474 A1 | 2/2004 |
| WO | WO-2004058097 A2 | 7/2004 |
| WO | WO-2005011534 A1 | 2/2005 |
| WO | WO-2005041810 A2 | 5/2005 |
| WO | WO-2005087140 A1 | 9/2005 |
| WO | WO-2006070372 A2 | 7/2006 |
| WO | WO-2006085304 A2 | 8/2006 |
| WO | WO-2006089236 A1 | 8/2006 |
| WO | WO 2006/097931 A2 | 9/2006 |
| WO | WO-2006127765 A1 | 11/2006 |
| WO | WO-2007025028 A1 | 3/2007 |
| WO | WO-2007034488 A2 | 3/2007 |
| WO | WO-2007058857 A2 | 5/2007 |
| WO | WO 2007/122459 A2 | 11/2007 |
| WO | WO-2007123658 A1 | 11/2007 |
| WO | WO-2007134290 A2 | 11/2007 |
| WO | WO 2008/013915 A2 | 1/2008 |
| WO | WO-2008005535 A2 | 1/2008 |
| WO | WO-2008070797 A2 | 6/2008 |
| WO | WO-2008091515 A2 | 7/2008 |
| WO | WO 2008/103722 A2 | 8/2008 |
| WO | WO-2008150529 A1 | 12/2008 |
| WO | WO-2009026563 A2 | 2/2009 |
| WO | WO 2009/033469 A1 | 3/2009 |
| WO | WO-2009033469 A1 | 3/2009 |
| WO | WO-2009045331 A1 | 4/2009 |
| WO | WO-2009045338 A1 | 4/2009 |
| WO | WO-2009052188 A1 | 4/2009 |
| WO | WO-2009053497 A1 | 4/2009 |
| WO | WO-2009091509 A1 | 7/2009 |
| WO | WO-2009094500 A1 | 7/2009 |
| WO | WO 2009/134701 A2 | 11/2009 |
| WO | WO-2009137359 A1 | 11/2009 |
| WO | WO-2009149462 A2 | 12/2009 |
| WO | WO-2009155561 A2 | 12/2009 |
| WO | WO 2010/004546 A1 | 1/2010 |
| WO | WO-2010008549 A1 | 1/2010 |
| WO | WO 2010/037141 A1 | 4/2010 |
| WO | WO-2010040009 A1 | 4/2010 |
| WO | WO-2010057262 A1 | 5/2010 |
| WO | WO-2010098857 A1 | 9/2010 |
| WO | WO-2010138853 A2 | 12/2010 |
| WO | WO-2011025945 A1 | 3/2011 |
| WO | WO-2011109813 A2 | 9/2011 |
| WO | WO 2011/137531 A1 | 11/2011 |
| WO | WO-2011137531 A1 | 11/2011 |
| WO | WO-2012035279 A1 | 3/2012 |
| WO | WO-2012162228 A1 | 11/2012 |
| WO | WO 2012/177942 A2 | 12/2012 |
| WO | WO-2013021374 A2 * | 2/2013 | ............ A61F 2/2418 |
| WO | WO-2013120181 A1 | 8/2013 |
| WO | WO-2013120181 A1 | 8/2013 |

OTHER PUBLICATIONS

US 8,221,315 B2, 07/2012, Lambrecht et al. (withdrawn)
Bavaria. CardiAQ Valve Technologies (CVT) discloses successful results of acute in vivo study of its novel transcatheter mitral valve implantation (TMVI) system. Enhanced Online News. Sep. 28, 2009. Accessed: Mar. 8, 2012. http://eon.businesswire.com/news/eon/20090928005120/en/CardiAQ-Valve-Technologies/Heart/heart-failure.
Bavaria. CardiAQ Valve Technologies. TCT Company Overview. Transcatheter Cardiovascular Therapeutics Conference. San Francisco, CA. Sep. 21-25, 2009.
CardiAQ Valve Technologies. Percutaneous mitral valve replacement. Start-Up. Jun. 2009; 14(6):48-49.
Carpentier-Edwards. Why compromise in the mitral position? Edwards Lifesciences. 2004.
Fitzgerald. Tomorrow's technology: percutaneous mitral valve replacement, chordal shortening and beyond. Transcatheter Valve Therapies (TVT) Conference. Seattle, WA. Jun. 7, 2010.
International search report and written opinion dated Jun. 25, 2014 for PCT/CA2014/000188.
Mack. Advantages and limitations of surgical mitral valve replacement; lessons for the transcatheter approach. Jun. 7, 2010. Texas Cardiovascular Innovative Ventures (TCIV) Conference. Dallas, TX. Dec. 8, 2010.
Medical Devices Today. CardiAQ Valve Technologies. Start-Up—Jul. 17, 2009. Accessed: Mar. 8, 2012. http:/www.medicaldevicestoday.com/2009/07/medical-device-start-up-cardiaq-valve-technologies-percutaneous-mitral-valve-replacement.html.
Ostrovsky. Transcatheter mitral valve implantation technology from CardiAQ. Posted Jan. 15, 2010. Accessed Jun. 27, 2012 from http://medgadget.com/2010/01/transcatheter_mitral_valve_implantation_technology_from_cardiaq.html.
Ratz. CardiAQ Valve Technologies. Innovations in heartvalve therapy. In3 San Francisco. Jun. 18, 2008. PowerPoint presentation in 19 slides.
Ruiz. Overview of novel transcatheter valve technologies. Glimpse into the future. New transcatheter mitral valve treatment. Euro PCR. Paris, France. May 27, 2010.
Al-Attar. Next generation surgical aortic biological prostheses: sutureless valves. European Society of Cardiology. Dec 21, 2011; 10(14):1-3. 0.

(56) References Cited

OTHER PUBLICATIONS

Banai, et al. Tiara: a novel catheter-based mitral valve bioprosthesis: initial experiments and short-term pre-clinical results. J Am Coll Cardiol. Oct. 9, 2012;60(15):1430-1. doi: 10.1016/j.jacc.2012.05.047. Epub Sep. 12, 2012.

Berreklouw, et al. Sutureless mitral valve replacement with bioprostheses and Nitinol attachment rings: feasibility in acute pig experiments. J Thorac Cardiovasc Surg. Aug. 2011;142(2):390-5.e1. doi: 10.1016/j.jtcvs.2010.12.018. Epub Feb. 4, 2011.

Boudjemline, et al. Steps toward the percutaneous replacement of atrioventricular valves an experimental study. J Am Coll Cardiol. Jul. 19, 2005;46(2):360-5.

Brinkman, et al. Transcatheter cardiac valve interventions. Surg Clin North Am. Aug. 2009;89(4):951-66, x. doi: 10.1016/j.suc.2009.06.004.

CardiAQ Valve Technologies to pursue first-in-man studies of its transcatheter mitral valve system. Cardiac Interventions Today. Jan. 12, 2010.

Chiam, et al. Percutaneous transcatheter aortic valve implantation: assessing results, judging outcomes, and planning trials: the interventionalist perspective. JACC Cardiovasc Interv. Aug. 2008;1(4):341-50. doi: 10.1016/j.jcin.2008.03.018.

Condado, et al. Percutaneous treatment of heart valves. Rev Esp Cardiol. Dec. 2006;59(12):1225-31.

CoreValve USA. An advanced TAVR design. Medtronic.com. Accessed Jan. 27, 2015.

De Backer, et al. Percutaneous transcatheter mitral valve replacement: an overview of devices in preclinical and early clinical evaluation. Circ Cardiovasc Interv. Jun. 2014;7(3):400-9. doi: 10.1161/CIRCINTERVENTIONS.114.001607.

Edwards Lifesciences 2005 annual report. Accessed Jan. 27, 2015.

Fanning, et al. Transcatheter aortic valve implantation (TAVI): valve design and evolution. Int J Cardiol. Oct. 3, 2013;168(3):1822-31. doi: 10.1016/j.ijcard.2013.07.117. Epub Aug. 20, 2013.

Gillespie, et al. Sutureless mitral valve replacement: initial steps toward a percutaneous procedure. Ann Thorac Surg. Aug. 2013;96(2):670-4. doi: 10.1016/j.athoracsur.2013.02.065.

Grube, et al. Percutaneous implantation of the CoreValve self-expanding valve prosthesis in high-risk patients with aortic valve disease: the Siegburg first-in-man study. Circulation. Oct. 10, 2006;114(15):1616-24. Epub Oct. 2, 2006.

Harmon, et al. Effect of acute myocardial infarction on the angle between the mitral and aortic valve plane. Am J Cardiol. Aug. 1, 1999;84(3):342-4, A8.

Herrman. Trancatheter mitral valve implantation. Cardiac Interventions Today. Aug./Sep. 2009; 81-85.

Ionasec, et al. Personalized modeling and assessment of the aortic-mitral coupling from 4D TEE and CT. Med Image Comput Comput Assist Interv. 2009;12(Pt 2):767-75.

Karimi, et al. Percutaneous Valve Therapies. SIS 2007 Year book. Chapter 11. 11 pages.

Kumar, et al. Design considerations and quantitative assessment for the development of percutaneous mitral valve stent. Med Eng Phys. Jul. 2014;36(7):882-8. doi: 10.1016/j.medengphy.2014.03.010. Epub Apr. 16, 2014.

Lauten; et al., "Experimental evaluation of the JenaClip transcatheter aortic valve.", Sep. 1, 2009, 74(3), 514-9.

Leon, et al. Transcatheter aortic valve replacement in patients with critical aortic stenosis: rationale, device descriptions, early clinical experiences, and perspectives. Semin Thorac Cardiovasc Surg. 2006 Summer;18(2):165-74.

Lozonschi, et al. Transapical mitrel valved stent implantation. Ann Thorac Surg. Sep. 2008;86(3):745-8. doi: 10.1016/j.athoracsur.2008.05.039.

Lutter, et al. Off-pump transapical mitrel valve replacement. Eur J Cardiothorac Surg. Jul. 2009;36(1):124-8; discussion 128. doi: 10.1016/j.ejcts.2009.02.037. Epub Apr. 25, 2009.

Lutter, et al. Transapical mitrel valve implantation: the Lutter valve. Heart Lung Vessel. 2013;5(4):201-6.

Ma, et al. Double-crowned valved stents for off-pump mitrel valve replacement. Eur J Cardiothorac Surg. Aug. 2005;28(2):194-8; discussion 198-9.

Maisano, et al. Mitral transcatheter technologies. Rambam Maimonides Med J. Jul. 25, 2013;4(3):e0015. doi: 10.5041/RMMJ.10115. Print Jul. 2013.

Navia, et al. Sutureless implantation a expandable mitrel stent-valve prosthesis in acute animal model. TCT728. JACC. Nov. 8, 2011. vol. 58, No. 20 Suppl B. B194.

Orton. Mitralseal: hybrid trancatheter mitrel valve replacement. Colorado State University. 2011; 311-312. https://www.acvs.org/files/proceedings/2011/data/papers/102.pdf.

Piazza, et al. Anatomy of the aortic valvar complex and its implications for transcatheter implantation of the aortic valve. Circ Cardiovasc Interv. Aug. 2008;1(1):74-81. doi: 10.1161/CIRCINTERVENTIONS.108.780858.

Pluth, et al. Aortic and mitrel valve replacement with cloth-covered Braunwald-Cutter prosthesis. A three-year follow-up. Ann Thorac Surg. Sep. 1975;20(3):239-48.

Preston-Maher, et al. A Technical Review of Minimally Invasive Mitral Valve Replacements. Cardiovasc Eng Technol. 2015;6(2):174-184. Epub Nov. 25, 2014.

Quadri, et al. CVT is developing a non-surgical apporach to replacing mitral valves that may be the alternative to open-chest surgery. CardiAQ Valve Technologies. May 8, 2009.

Ribiero, et al. Balloon-expandable prostheses for transcatheter aortic valve replacement. Prog Cardiovasc Dis. May-Jun. 2014;56(6):583-95. doi: 10.1016/j.pcad.2014.02.001. Epub Mar. 1, 2014.

Seidel, et al. A mitrel valve prosthesis and a study of thrombosis on heart valves in dogs. J Surg Res. May 1962;2:168-75.

Shuto, et al. Percutaneous transvenous Melody valve-in-ring procedure for mitrel valve replacement. J Am Coll Cardiol. Dec. 6, 2011;58(24):2475-80. doi: 10.1016/j.jacc.2011.09.021.

Sondergaard, et al. First-in-human CardiAQ transcatheter mitrel valve implantation via transapical approach. TCT-811. JACC. Sep. 13, 2014. vol. 64, No. 11 Suppl B. B237.

Spencer, et al. Surgical treatment of valvular heart disease. Part V. Prosthetic replacement of the mitral valve. American Heart Journal. Oct. 1968; 76(4):576-580.

Spillner, et al. New sutureless 'atrial mitral-valve prosthesis' for minimally invasive mitral valve therapy. Textile Research Journal. 2010:1-7.

Tavr. Engager system. Precise Valve positioning. Accessed Jan. 28, 2015.

The JenaValve—the prosthesis. JenaValve Technology. Accessed Jan. 28, 2015.

Timek, et al. Aorto-mitral annular dynamics. Ann Thorac Surg. Dec. 2003;76(6):1944-50.

Tsang, et al. Changes in aortic-mitral coupling with severe aortic stenosis. JACC. Mar. 9, 2010; vol. 55. Issue 1A.

Veronesi, et al. A study of functional anatomy of aortic-mitral valve coupling using 3D matrix transesophageal echocardiography. Circ Cardiovasc Imaging. Jan. 2009;2(1):24-31. doi: 10.1161/CIRCIMAGING.108.785907. Epub Dec. 2, 2008.

Vu, et al. Novel sutureless mitrel valve implantation method involving a bayonet insertion and release mechanism: a proof of concept study in pigs. J Thorac Cardiovasc Surg. Apr. 2012;143(4):985-8. doi: 10.1016/j.jtcvs.2012.01.037. Epub Feb. 11, 2012.

Walther, et al. Transapical approach for sutureless stent-fixed aortic valve implantation: experimental results. Eur J Cardiothorac Surg. May 2006;29(5):703-8. Epub Apr. 5, 2006.

Webb, et al. Transcatheter aortic valve implantation: the evolution of prostheses, delivery systems and approaches. Arch Cardiovasc Dis. Mar. 2012;105(3):153-9. doi: 10.1016/j.acvd.2012.02.001. Epub Mar. 16, 2012.

50 Early-to Late-Stage Medical Device Companies Seeking Investment and Partnering Opportunities to Present in 3 Weeks at Investment in Innovation (In3) Medical Device Summit. Businesswire.com. Dated May 27, 2008. 3 pages.

(56) References Cited

OTHER PUBLICATIONS

CardiAQ's Complaint and Jury Demand; U.S. District Court—District of Massachusetts; Case No. 1:14-cv-12405-ADB; *CardiAQ Valve, Technologies Inc.* v. *Neovasc Inc. and Neovasc Tiara Inc.*; filed Jun. 6, 2014. 22 pages.
CardiAQ's First Amended Complaint and Jury Demand; U.S. District Court—District of Massachusetts; Case No. 1:14-cv-12405-ADB; *CardiAQ Valve, Technologies Inc.* v. *Neovasc Inc. and Neovasc Tiara Inc.*; filed Aug. 12, 2014. 21 pages.
CardiAQ's Objection in Patent Vindication Action in regard to EP 2 566 416; Administrative Court of Munich; *CardiAQ Valve Technologies, Inc.*, v. *Neovasc Tiara Inc.*; filed on Jun. 25, 2014. 22 pages.
CardiAQ's Second Amended Complaint and Jury Demand; U.S. District Court—District of Massachusetts; Case No. 1:14-cv-12405-ADB; *CardiAQ Valve, Technologies Inc.* v. *Neovasc Inc. and Neovasc Tiara Inc.*; filed Jan. 15, 2015. 25 pages.
CardiAQ Valve Technologies (CVT) Elects Michael Mack, MD, to its Scientific Advisory Board. "CVT's Transcatheter Mitral Valve Implanation (TMVI) platform might be the 'next big thing' in the cardiac cath lab." BusinessWire. Dated Jun. 2, 2009. 4 pages.
CardiAQ Valve Technologies ("CVT") to disclose data during 'EuroPCR 2010' about the world's first successful in vivo transcatheter delivery of a mitral heart valve implant. Irvine, California, Businesswire.com. Dated May 20, 2010. 2 pages.
Company Fact Sheet—CardiAQ Valve Technologies. 2009. 1 page.
Company Overview—CardiAQ Valve Technologies. Dated Jun. 25, 2009 at TVT. 17 pages.
Court's Memorandum & Order; U.S. District Court—District of Massachusetts; Case No. 1:14-cv-12405-ADB; *CardiAQ Valve, Technologies Inc.* v. *Neovasc Inc. and Neovasc Tiara Inc.*; filed Nov. 6, 2014. 14 pages.
Defendants Neovasc Inc.'s and Neovasc Tiara Inc.'s Answer to Plaintiff's First Amended Complaint; U.S. District Court—District of Massachusetts; Case No. 1:14-cv-12405-ADB; *CardiAQ Valve, Technologies Inc.* v. *Neovasc Inc. and Neovasc Tiara Inc.*; filed Nov. 20, 2014. 20 pages.
Defendants Neovasc Inc.'s and Neovasc Tiara Inc.'s Answer to Plaintiff's Second Amended Complaint; U.S. District Court—District of Massachusetts; Case No. 1:14-cv-12405-ADB; *CardiAQ Valve, Technologies Inc.* v. *Neovasc Inc. and Neovasc Tiara Inc.*; filed Jan. 29, 2015. 22 pages.
European Extended Search Report dated Jan. 30, 2014 for EP Application No. EP 11798780.
European Extended Search Report dated Feb. 28, 2013 for EP Application No. EP 06827638.
Exhibits accompanying CardiAQ's Objection in Patent Vindication Action in regard to EP 2 566 416; filed on Jun. 25, 2014. 306 pages.
Exhibits accompanying Neovasc's Statement of Defense in Patent Vindication Action in regard to EP 2 566 416; filed on Dec. 9, 2014. 67 pages.
Feldman, et al. Prospects for percutaneous valve therapies. Circulation. Dec. 11, 2007;116(24):2866-77.
Grube, et al. Percutaneous aortic valve replacement for severe aortic stenosis in high-risk patients using the second- and current third-generation self-expanding CoreValve prosthesis: device success and 30-day clinical outcome. J Am Coll Cardiol. Jul. 3, 2007;50(1):69-76. Epub Jun. 6, 2007.
Horvath, et al. Transapical aortic valve replacement under real-time magnetic resonance imaging guidance: experimental results with balloon-expandable and self-expanding stents. Eur J Cardiothorac Surg. Jun. 2011;39(6):822-8. doi: 10.1016/j.ejcts.2010.09.030. Epub Oct. 22, 2010.
International Search Report and Written Opinion dated Feb. 29, 2012 for PCT/US2011/041306.
International Search Report and Written Opinion dated Mar. 26, 2008 for PCT/US2007/016855.
International Search Report and Written Opinion dated Jun. 25, 2008 for PCT/US2006/043526.
International Search Report and Written Opinion dated Dec. 11, 2009 for PCT/US2009/058893.
International Search Report and Written Opinion dated Dec. 18, 2009 for PCT/US2009/059299.
International Search Report and Written Opinion dated Dec. 22, 2010 for PCT/US2010/031313.
Kronemyer. CardiAQ Valve Technologies: Percutaneous Mitral Valve Replacement. Start Up—Windhover Review of Emerging Medical Ventures, vol. 14, No. 6, Jun. 2009, pp. 48-49.
Lansac, et al. Dynamic balance of the aortomitral junction. J Thorac Cardiovasc Surg. May 2002;123(5):911-8.
Lauten, et al. Experimental evaluation of the JenaClip transcatheter aortic valve. Catheter Cardiovasc Interv. Sep. 1, 2009;74(3):514-9. doi: 10.1002/ccd.22093.
Lutter, G et al.: "Transcatheter Mitral Valve Replacement—Early Animal Results," Universitatsklinikum, Schleswig-Holstein. Aug. 28, 2012.
Mack, Michael, M.D., "Antegrade Transcatheter Mitral valve Implantation: A Short-term Experience in Swine Model." Applicant believes this may have been presented on May of 2011 at TVT. 10 pages.
Masson, et al. Percutaneous treatment of mitral regurgitation. Circ Cardiovasc Interv. Apr. 2009;2(2):140-6. doi: 10.1161/CIRCINTERVENTIONS.108.837781.
Neovasc corporate presentation, Oct. 2009. 21 pages. Available at http://www.neovasc.com/investors/documents/Neovasc-Corporate-Presentation-October-2009.pdf.
Neovasc Ostial Products Overview. 1 page. https://web.archive.org/web/20090930050359/https://www.neovasc.com/vascular-products/ostialproducts/default.php (Neovasc website archived as of Sep. 30, 2008).
Neovasc's Statement of Defense in Patent Vindication Action in regard to EP 2 566 416; Administrative Court of Munich; *CardiAQ Valve Technologies, Inc.*, v. *Neovasc Tiara Inc.*; filed on Dec. 9, 2014. 39 pages.
Neovasc Surgical Products: An Operating Division of Neovasc Inc. Dated Apr. 2009. 17 pages.
Nkomo, et al. Burden of valvular heart diseases: a population-based study. Lancet. Sep. 16, 2006;368(9540):1005-11.
Ormiston, et al. Size and motion of the mitral valve annulus in man. I. A two-dimensional echocardiographic method and findings in normal subjects. Circulation. Jul. 1981;64(1):113-20.
Ostrovsky, Gene, "A Trial of Zenith Fenestrated AAA Endovascular Graft Goes on," medGadget, Aug. 1, 2008, 9 pages. Available at: http://www.medgadget.com/2008/08/a_trial_of_zenith_fenestrated_aaa_endovascular_graft_goes_on.html.
Otto. Clinical practice. Evaluation and management of chronic mitral regurgitation. N Engl J Med. Sep. 6, 2001;345(10):740-6.
Quadri, Arshad M.D., "Transcatheter Mitral Valve Implantation (TMVI) (An Acute In Vivo Study)," Applicant believes this may have been presented on Sep. 22, 2010 at TCT. 19 pages.
Ratz, et al. "Any experiences making an expandable stent frame?" Arch-Pub.com, Architecture Forums: Modeling, Multiple forum postings from Feb. 3, 2009 to Feb. 4, 2009, http://www.arch-pub.com/Any-experiences-making-an-expandable-stent-frame_10601513.html. 5 pages.
Ratz, J. Brent et al., "Fabric, Skin, Cloth expansion . . . best approach'?," AREA by Autodesk, 3ds Max: Modeling, Forum postings from Feb. 18, 2009 to Feb. 19, 2009, http://forums.autodesk.com/t5/modeling/fabric-skin-cloth-expansion-best-approach/td-p/4062607. 3 pages.
Ratz, J. Brent et al., "Isolating Interpolation," Arch-Pub.com, Architecture Forums: Animation and Rigging, Forum postings from Feb. 9, 2009 to Feb. 10, 2009, http://www.arch-pub.com/Isolating-Interpolation_10593153.html. 2 pages.
Ratz, J. Brent, "In3 Company Overview," Jun. 24, 2009. 15 pages.
Ratz, J. Brent, "LSI EMT Spotlight," May 15, 2009. 21 pages.
Ross, Renal Ostial Stent System with Progressi-flex Technology, Evasc Medical Systems. 1 page. Applicant requests the Examiner to consider this reference to be prior art as of Jun. 2009.
Update—CardiAQ Valve Technologies. Presented on Jun. 6, 2010 at TVT. 12 pages.

(56) References Cited

OTHER PUBLICATIONS

Van Mieghem, et al. Anatomy of the mitral valvular complex and its implications for transcatheter interventions for mitral regurgitation. J Am Coll Cardiol. Aug. 17, 2010;56(8):617-26. doi: 10.1016/j.jacc.2010.04.030.

Yamada, et al. The left ventricular ostium: an anatomic concept relevant to idiopathic ventricular arrhythmias. Circ Arrhythm Electrophysiol. Dec. 2008;1(5):396-404. doi: 10.1161/CIRCEP.108.795948.

European Search Report dated Oct. 17, 2016 for European Application No. 14764106.2.

"Australian Application Serial No. 2014231689, First Examination Report daetd Sep. 5, 2018", 3 pgs.

"Australian Application Serial No. 2014231689, Response file Dec. 19, 2018 to Examination Report dated Sep. 5, 2018", 24 pgs.

"European Application Serial No. 14764106.2, Response filed May 15, 2017 to Extended European Search Report dated Oct. 17, 2016", 27 pgs.

"International Application Serial No. PCT/CA2014/000188, International Preliminary Report on Patentability dated Sep. 24, 2015", 8 pgs.

"European Application Serial No. 14764106.2, Communication Pursuant to Article 94(3) EPC dated Jun. 19, 2019", 5 pgs.

"European Application Serial No. 14764106.2, Response filed Oct. 29, 2019 to Communication Pursuant to Article 94(3) EPC dated Jun. 19, 2019", 12 pgs.

* cited by examiner

PROSTHETIC VALVE WITH ANTI-PIVOTING MECHANISM

CROSS-REFERENCE

The present application is a non-provisional of, and claims the benefit of U.S. Provisional Patent Application No. 61/776,566 filed Mar. 11, 2013; the entire contents of which are incorporated herein by reference.

The present application is related to U.S. patent application Ser. No. 13/096,572 filed Apr. 28, 2011; and also related to U.S. patent application Ser. No. 13/679,920 filed Nov. 16, 2012; the entire contents of which are incorporated herein by reference.

BACKGROUND OF THE INVENTION

1. Field of the Invention

The present invention generally relates to medical devices and methods, and more particularly relates to the treatment of valve insufficiency, such as mitral insufficiency, also referred to as mitral regurgitation. The use of prosthetic valves delivered by traditional surgical implantation methods, or by a less invasive percutaneous catheter or by minimally invasive transapical methods are one possible treatment for valvar insufficiency (also referred to as regurgitation).

The heart of vertebrate animals is divided into four chambers, and is equipped with four valves (the mitral, aortic, pulmonary and tricuspid valves) that ensure that blood pumped by the heart flows in a forward direction through the cardiovascular system. The mitral valve of a healthy heart prevents the backflow of blood from the left ventricle into the left atrium of the heart, and comprises two flexible leaflets (anterior and posterior) that close when the left ventricle contracts. The leaflets are attached to a fibrous annulus, and their free edges are tethered by subvalvular chordae tendineae to papillary muscles in the left ventricle to prevent them from prolapsing into the left atrium during the contraction of the left ventricle.

Various cardiac diseases or degenerative changes may cause dysfunction in any of these portions of the mitral valve apparatus, causing the mitral valve to become abnormally narrowed or dilated, or to allow blood to leak (i.e. regurgitate) from the left ventricle back into the left atrium. Any such impairments compromise cardiac sufficiency, and can be debilitating or life threatening.

Numerous surgical methods and devices have accordingly been developed to treat mitral valve dysfunction, including open-heart surgical techniques for replacing, repairing or re-shaping the native mitral valve apparatus, and the surgical implantation of various prosthetic devices such as annuloplasty rings to modify the anatomy of the native mitral valve. More recently, less invasive transcatheter techniques for the delivery of replacement mitral valve assemblies have been developed. In such techniques, a prosthetic valve is generally mounted in a crimped state on the end of a flexible catheter and advanced through a blood vessel or the body of the patient until the valve reaches the implantation site. The prosthetic valve is then expanded to its functional size at the site of the defective native valve.

While these devices and methods are promising treatments for valvar insufficiency, they can be difficult to deliver and anchor, expensive to manufacture, or may not be indicated for all patients. Some of these prosthetic valves having anchoring mechanisms that secure the valve to various portions of the valve anatomy. For example, some the valves are anchored to the atrial floor, the valve annulus, a ventricular wall, or to the valve leaflets. However, in some situations, depending on anatomy, skill of the physician, as well as other factors, the prosthetic valve may not always be successfully anchored. For example, in the case of a prosthetic mitral valve with anchors for securing the valve to the native anterior and posterior leaflets, if the anchor(s) do not successfully engage the posterior leaflet, the prosthetic valve may be pushed upward toward the atrium during ventricular contraction due to the force of the blood. This may result in an improperly positioned valve which can prevent the valve from properly functioning. Therefore, it would be desirable to provide improved devices and methods for the treatment of valvar insufficiency such as mitral insufficiency. Such devices preferably have alternative or improved anchoring mechanisms to more securely anchor the prosthesis to the valve structure. At least some of these objectives will be met by the devices and methods disclosed below.

2. Description of the Background Art

By way of example, PCT international patent number PCT/US2008/054410 (published as PCT international publication No. WO2008/103722), the disclosure of which is hereby incorporated by reference, describes a transcatheter mitral valve prosthesis that comprises a resilient ring, a plurality of leaflet membranes mounted with respect to the ring so as to permit blood flow therethrough in one direction, and a plurality of tissue-engaging positioning elements movably mounted with respect to the ring and dimensioned to grip the anatomical structure of the heart valve annulus, heart valve leaflets, and/or heart wall. Each of the positioning elements defines respective proximal, intermediate, and distal tissue engaging regions cooperatively configured and dimensioned to simultaneously engage separate corresponding areas of the tissue of an anatomical structure, and may include respective first, second, and third elongate tissue-piercing elements. The valve prosthesis may also include a skirt mounted with respect to the resilient ring for sealing a periphery of the valve prosthesis against a reverse flow of blood around the valve prosthesis.

PCT international patent number PCT/US2009/041754 (published as PCT international publication No. WO2009/134701), the disclosure of which is hereby incorporated by reference, describes a prosthetic mitral valve assembly that comprises an anchor or outer support frame with a flared upper end and a tapered portion to fit the contours of the native mitral valve, and a tissue-based one-way valve mounted therein. The assembly is adapted to expand radially outwardly and into contact with the native heart tissue to create a pressure fit, and further includes tension members anchoring the leaflets of the valve assembly to a suitable location on the heart to function as prosthetic chordae tendineae.

Also known are prosthetic mitral valve assemblies that utilize a claw structure for attachment of the prosthesis to the heart (see, for example, U.S. Patent Publication No. US2007/0016286 to Hermann et al., the disclosure of which is hereby incorporated by reference), as are prosthetic mitral valve assemblies that rely on the application of axial rather than radial clamping forces to facilitate the self-positioning and self-anchoring of the prosthesis with respect to the native anatomical structure.

Another method which has been proposed as a treatment of mitral valve regurgitation is the surgical bow tie method, which recently has been adapted into a minimally invasive catheter based treatment where an implant is used to clip the valve leaflets together. This procedure is more fully disclosed in the scientific and patent literature, such as in U.S.

Pat. No. 6,629,534 to St. Goar et al., the entire contents of which are incorporated herein by reference.

Other relevant publications include U.S. Patent Publication No. 2011/0015731 to Carpentier et al. and WO2011/137531 to Lane et al. While some of these devices and methods are promising, there still is a need for improved devices and methods that will further allow more accurate positioning of a prosthetic valve and that will also more securely anchor the valve in place. At least some of these objectives will be met by the exemplary embodiments disclosed herein.

SUMMARY OF THE INVENTION

The present invention generally relates to medical devices and methods, and more particularly prosthetic valves used to treat mitral regurgitation. While the present disclosure focuses on the use of a prosthetic valve for treating mitral regurgitation, this is not intended to be limiting. The prosthetic valves disclosed herein may also be used to treat other body valves including other heart valves or venous valves. Exemplary heart valves include the aortic valve, the tricuspid valve, or the pulmonary valve.

In a first aspect of the present invention, a prosthetic valve for implanting in a native valve of a patient comprises a self-expanding frame having a first end, a second end opposite the first end, an atrial region near the second end, a ventricular region near the first end, an anterior portion, and a posterior portion. The self-expanding frame has an expanded configuration and a collapsed configuration. The expanded configuration is adapted to engage tissue at a treatment site, and the collapsed configuration is adapted to be delivered to the treatment site. The expandable frame comprises a self-expanding atrial skirt disposed in the atrial region, a self-expanding ventricular skirt disposed in the ventricular region, a self-expanding annular region disposed between the atrial region and the ventricular region, a first self-expanding anterior tab disposed on the anterior portion of the self-expanding frame in the ventricular region, and a self-expanding foot coupled to the ventricular region. The foot is disposed in the posterior portion and extends radially outward from the self-expanding frame and has an outer surface for engaging the tissue thereby facilitating anchoring of the prosthetic valve and minimizing or preventing rotation of the prosthetic valve. Preferably the foot prevents or minimizes rotation of the prosthesis upstream into or toward the left atrium, although it may help anchor the prosthesis and prevent or minimize pivoting in a direction that depends on the anatomy being treated.

The prosthetic valve may be a prosthetic mitral valve. The atrial skirt may have a collapsed configuration and an expanded configuration. The collapsed configuration may be adapted for delivery to the treatment site, and the expanded configuration may be radially expanded relative to the collapsed configuration and adapted to lie over a superior surface of the patient's native valve, thereby anchoring the atrial skirt against a superior portion of the native valve. The atrial skirt may comprise a plurality of axially oriented struts connected together with a connector element thereby forming a series of peaks and valleys. After self-expansion of the atrial skirt, the atrial skirt may form a flanged region adjacent the second end of the self-expanding frame. The atrial skirt may have an asymmetrically D-shaped cross-section having a substantially flat anterior portion, and a cylindrically shaped posterior portion after self-expansion. The prosthetic valve may further comprise an alignment element coupled to an anterior portion of the atrial skirt. The alignment element may be adapted to be aligned with an aortic root of a patient's heart and may be adapted to be disposed between two fibrous trigones of an anterior leaflet of the patient's mitral valve.

At least a portion of the ventricular skirt may be covered with tissue or a synthetic material. After self-expanding, the ventricular skirt may comprise an asymmetrically D-shaped cross-section having a substantially flat anterior portion, and a cylindrically shaped posterior portion. The ventricular skirt may have a collapsed configuration and an expanded configuration. The collapsed configuration may be adapted for delivery to the treatment site, and the expanded configuration may be radially expanded relative to the collapsed configuration and may also be adapted to displace native mitral valve leaflets radially outward. The ventricular skirt may further comprise a plurality of barbs coupled thereto. The plurality of barbs may be adapted to anchor the ventricular skirt into the tissue. The ventricular skirt may comprise a plurality of struts connected together with a connector element thereby forming a series of peaks and valleys. Any of the struts in the prosthetic valve may have one or more suture holes extending through the strut and sized to receive a suture.

The annular region may have a collapsed configuration and an expanded configuration. The collapsed configuration may be adapted for delivery to the treatment site. The expanded configuration may be radially expanded relative to the collapsed configuration and may be adapted to conform with and may be adapted to engage an annulus of the native valve. After self-expanding, the annular region may have an asymmetrically D-shaped cross-section having a substantially flat anterior portion, and may also have a cylindrically shaped posterior portion. The annular region may comprise a plurality of axially oriented struts connected together with a connector element, and that may form a series of peaks and valleys. One or more of the plurality of axially oriented struts may comprise one or more suture holes extending through the strut, and the holes may be sized to receive a suture.

The first anterior tab may have a tip portion that is adapted to engage a first fibrous trigone on a first side of an anterior leaflet of the patient's mitral valve. The first anterior tab may be adapted to capture the anterior leaflet and adjacent chordae tendineae between the first anterior tab and an outer anterior surface of the ventricular skirt. The prosthetic valve may further comprise a second self-expanding anterior tab disposed on the anterior portion of the self-expanding frame in the ventricular region. The second anterior tab may have a tip portion that is adapted to engage a second fibrous trigone on a second side of the anterior leaflet of the patient's mitral valve opposite the first side of the anterior leaflet. The second anterior tab may be adapted to capture the anterior leaflet and adjacent chordae tendineae between the second anterior tab and the outer surface of the ventricular skirt.

The prosthetic valve may further comprise a covering disposed over the first or the second anterior tabs. The covering increases contact surface area of the respective first or second anterior tab with the heart or other treatment tissue. The covering may comprise a fabric material disposed over a polymer tab that is coupled to the first or the second anterior tab.

Rotation of the posterior portion of the prosthetic valve may be minimized or prevented relative to the anterior portion of the prosthetic valve with the foot. Rotation may be minimized or prevented in an upstream direction toward the left atrium of the patient's heart. The foot may be covered with a synthetic material or with tissue. The foot may comprise a wedge shaped element extending radially outward from the self-expanding frame. The foot may comprise a central elongate element and a cover. The cover may be disposed over the central elongate element and the cover may be coupled to a strut on either side thereof. The central elongate element may comprise a pair of struts coupled together to form a U-shape or a V-shape. The foot may form a vestibule on the posterior portion of the prosthetic valve. The foot may comprise barbs, texturing or other surface features for anchoring the foot to tissue.

The prosthetic valve may further comprise a plurality of prosthetic valve leaflets. Each of the leaflets may have a first end and a free end, and the first end may be coupled with the self-expanding frame and the free end may be opposite of the first end. The prosthetic valve leaflets may have an open configuration in which the free ends of the prosthetic valve leaflets are disposed away from one another to allow antegrade blood flow therepast, and a closed configuration in which the free ends of the prosthetic valve leaflets engage one another and substantially prevent retrograde blood flow therepast. The plurality of prosthetic valve leaflets may form a tricuspid valve. At least a portion of one or more prosthetic valve leaflets may comprise tissue or a synthetic material. One or more of the prosthetic valve leaflets may comprise a commissure post having a commissure tab. The commissure tab may be adapted to be releasably engaged with a delivery device. The prosthetic valve may carry a therapeutic agent that is adapted to being eluted therefrom. The prosthetic valve may further comprise a posterior ventricular anchoring tab disposed on a posterior portion of the self-expanding frame. The posterior ventricular anchor tab may be anchored over a posterior leaflet of the patient's mitral valve such that the posterior ventricular anchoring tab is seated between the posterior leaflet and a ventricular wall of the patient's heart. The posterior ventricular anchoring tab may have barbs, texturing or other surface features disposed thereon, and that are adapted to engage tissue and anchor the posterior ventricular tab to the tissue.

In another aspect of the present invention, a method for anchoring a prosthetic valve in a native valve of a patient's heart comprises providing a prosthetic valve and advancing the prosthetic valve in a collapsed configuration to the native valve. The prosthetic valve may comprise an expandable frame having a first end, a second end opposite the first end, a first anterior tab on an anterior portion of the expandable frame adjacent the first end, a foot on a posterior portion of the expandable frame adjacent the first end, an atrial skirt adjacent the second end of the expandable frame, and an annular region disposed between the first and second ends. The prosthetic valve also has an expanded configuration for engaging the native valve. The method also includes expanding the first anterior tab, and expanding the foot. The first anterior tab is expanded radially outward such that a tip of the first anterior tab engages a first fibrous trigone on a first side of an anterior leaflet of the native valve. The anterior leaflet may then be disposed between the first anterior tab and an outer surface of the ventricular skirt. The foot is expanded radially outward such that the foot engages a posterior portion of the native valve thereby anchoring the prosthetic valve to a posterior portion of the native valve and preventing or minimizing rotation of the prosthetic valve upstream into or toward the left atrium.

Providing the prosthetic valve may further comprise providing a delivery device for delivering the prosthetic valve to the native valve, and the prosthetic valve may be releasably coupled to the delivery device.

Advancing the prosthetic valve may comprise transapically delivering the prosthetic valve from a region outside of the patient to the patient's heart. Advancing the prosthetic valve may comprise transseptally delivering the prosthetic valve from the right atrium to the left atrium of the patient's heart. Advancing the prosthetic valve may comprise positioning the prosthetic valve across the patient's mitral valve so that the second end is superior to the mitral valve and the first end is inferior to the mitral valve.

Expanding the first anterior tab may comprise retracting a constraining sheath therefrom and allowing the first anterior tab to self-expand radially outward. The prosthetic valve may further comprise a second anterior tab on the anterior portion of the expandable frame, and the method may further comprise expanding the second anterior tab radially outward such that a tip portion of the second anterior tab engages a second fibrous trigone on a second side of the anterior leaflet opposite the first side of the anterior leaflet. The second anterior tab may expand radially outward concurrently with expansion of the first anterior tab. Expanding the second anterior tab may comprise retracting a constraining sheath from the second anterior tab so that the second anterior tab is free to self-expand radially outward. The first and second anterior tabs may both self-expand when a single constraining sheath is retracted.

Expanding the foot may form a vestibule adjacent the first end of the prosthetic valve, and may increase the size of the first end of the prosthetic valve so that it cannot pass through the native valve. Expanding the foot may comprise retracting a constraint therefrom so that the foot self-expands radially outward. The posterior chordae tendineae may engage the expanded foot. The foot may comprise barbs, texturing, or other surface features. Expanding the foot may engage the barbs, texturing or other surface features with tissue thereby anchoring the foot with the tissue.

The method may also comprise expanding the ventricular skirt radially outward into engagement with the anterior and posterior leaflets of the native valve. The anterior chordae tendineae may be disposed between the first anterior tab and the outer surface of the ventricular skirt. Expanding the ventricular skirt may comprise retracting a constraining sheath from the ventricular skirt so that the ventricular skirt is free to self-expand radially outward. The ventricular skirt may comprise a plurality of barbs, and expanding the ventricular skirt may comprise anchoring the plurality of barbs into heart tissue. The prosthetic valve may further comprise a plurality of commissures, and expanding the ventricular skirt may displace the anterior and posterior leaflets of the native valve radially outward thereby preventing interference between the commissures and the leaflets. Expanding the ventricular skirt may displace the anterior and posterior leaflets of the native valve radially outward without contacting an inner wall of the left ventricle, and without obstructing a left ventricular outflow tract. Radially expanding the ventricular skirt may expand the ventricular skirt asymmetrically such that an anterior portion of the ventricular skirt is substantially flat, and a posterior portion of the ventricular skirt is cylindrically shaped.

The method may also include expanding the annular region radially outward so as to engage an annulus of the native valve. Expanding the annular region may comprise retracting a constraining sheath therefrom so that the annular region is free to self-expand radially outward. Expanding the annular region may comprise asymmetrically expanding the annular region such that an anterior portion of the annular region is substantially flat, and a posterior portion of the annular region is cylindrically shaped.

The native valve may be a mitral valve, and the method may further comprise reducing or eliminating mitral regurgitation. The prosthetic valve may carry a therapeutic agent, and the method may further comprise eluting the therapeutic agent from the prosthetic valve into adjacent tissue.

The prosthetic valve may comprise an alignment element, the method may further comprise aligning the alignment element with an aortic root and disposing the alignment element between the first and second fibrous trigones. Aligning the alignment element may comprise rotating the prosthetic valve.

The prosthetic valve may further comprise a plurality of commissures with a covering disposed thereover whereby a plurality of prosthetic valve leaflets are formed. The method may further comprise releasing the plurality of prosthetic valve leaflets from a delivery catheter. The plurality of prosthetic valve leaflets may form a tricuspid valve that has an open configuration and a closed configuration. The plurality of prosthetic valve leaflets are disposed away from one another in the open configuration thereby permitting antegrade blood flow therethrough, and the plurality of prosthetic valve leaflets engage one another in the closed configuration thereby substantially preventing retrograde blood flow therethrough. The prosthetic valve may further comprise an atrial skirt adjacent the second end, and the method may further comprise expanding the atrial skirt radially outward so as to lie over a superior surface of the native valve, and engaging the atrial skirt against the superior surface of the native valve. Expanding the atrial skirt may comprise retracting a constraining sheath from the atrial skirt so that the atrial skirt is free to self-expand radially outward. The method may also comprise moving the prosthetic valve upstream or downstream relative to the native valve to ensure that the atrial skirt engages the superior surface of the native valve. Engaging the atrial skirt against the superior surface may seal the atrial skirt against the superior surface of the native valve to prevent or substantially prevent blood flow therebetween. The prosthetic valve may further comprise a posterior ventricular anchoring tab that is disposed on a posterior portion of the self-expanding frame. The method may further comprise anchoring the posterior ventricular anchoring tab over a posterior leaflet of the patient's mitral valve such that the posterior ventricular anchoring tab is seated between the posterior leaflet and a ventricular wall of the patient. The posterior ventricular tab may comprise barbs, texturing, or other surface features. Anchoring the posterior ventricular tab may comprise engaging the barbs, texturing or other surface features with tissue.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

Figure 1:
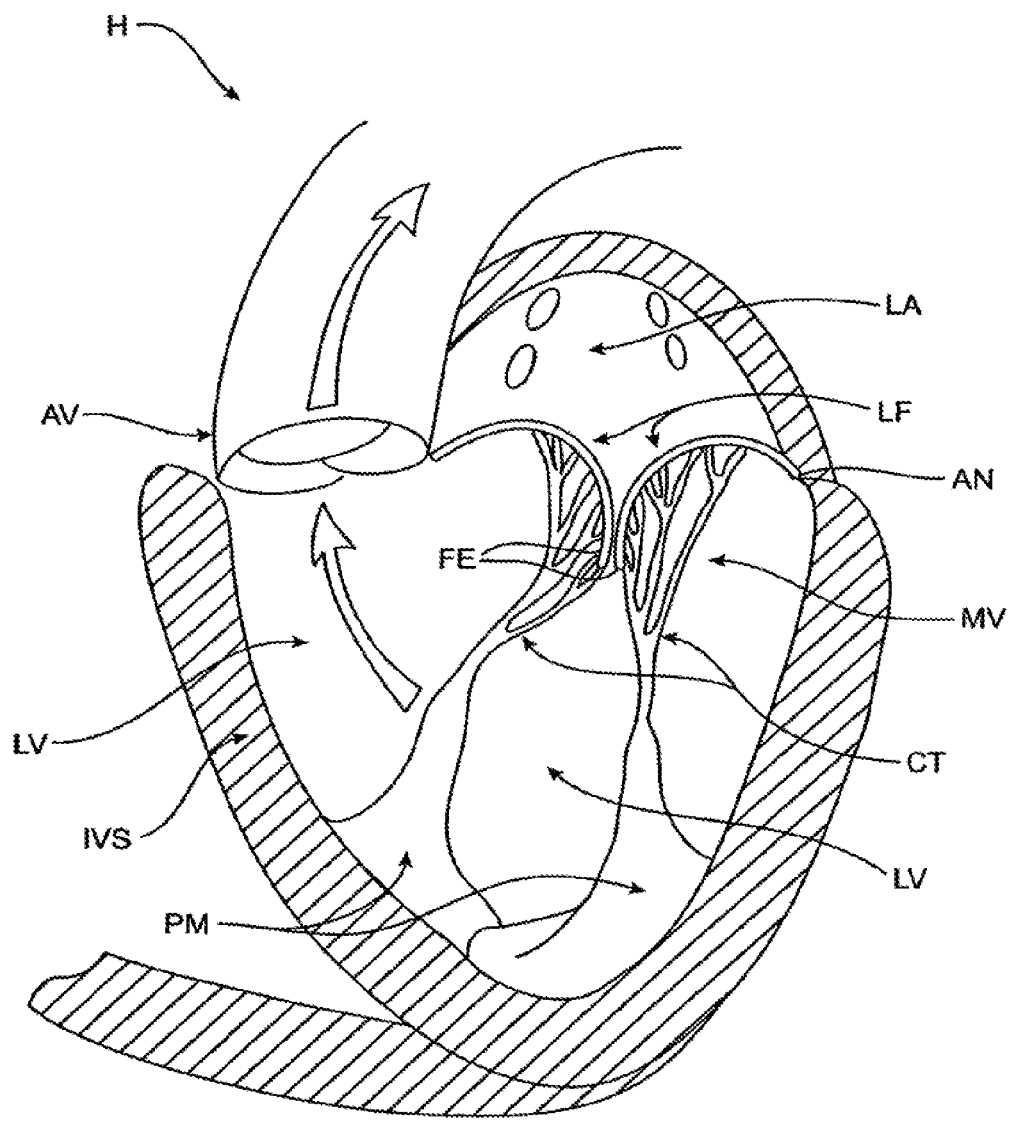
FIG. 1 is a schematic illustration of the left ventricle of a heart showing blood flow during systole with arrows.

Cardiac Anatomy. The left ventricle LV of a normal heart H in systole is illustrated in FIG. 1. The left ventricle LV is contracting and blood flows outwardly through the aortic valve AV, a tricuspid valve in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (also referred to herein as the chordae) which include a plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2:
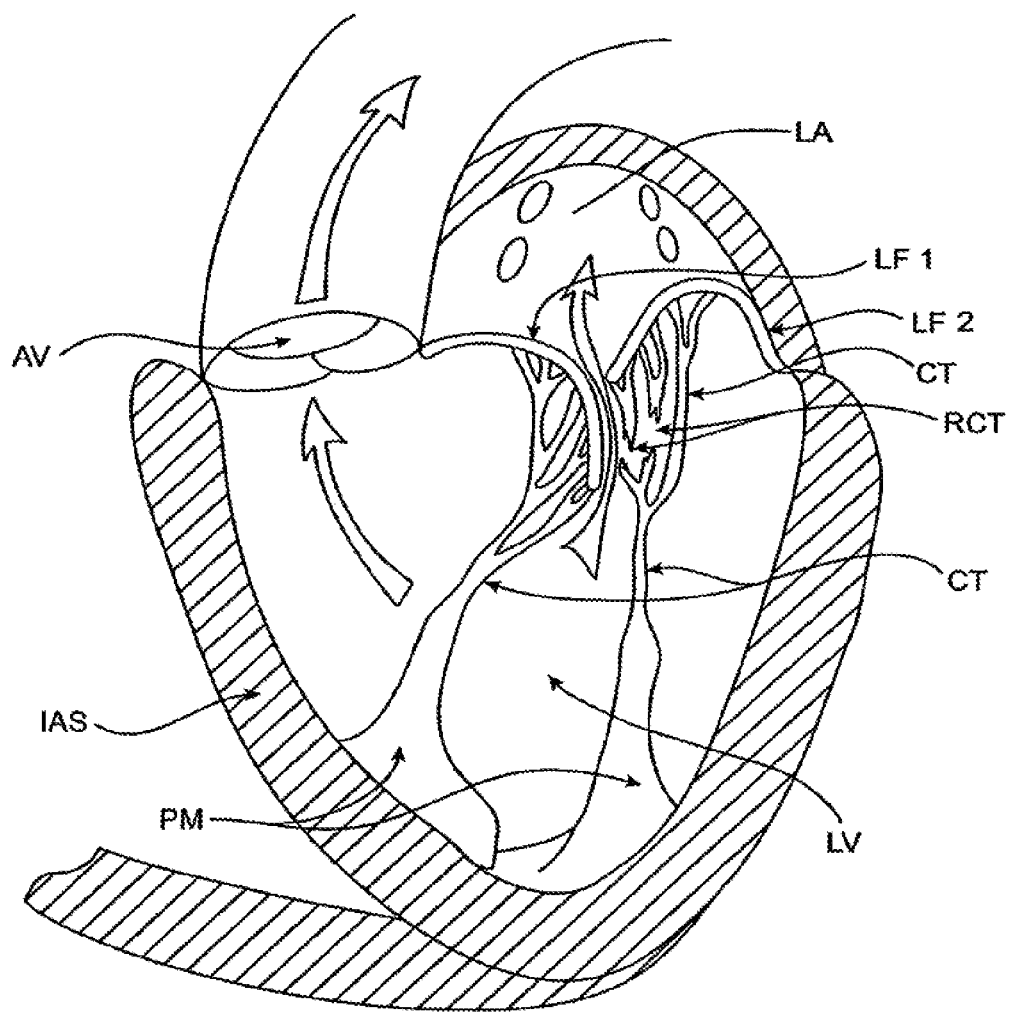
FIG. 2 is a schematic illustration of the left ventricle of a heart having prolapsed leaflets in the mitral valve.
Figure 3:
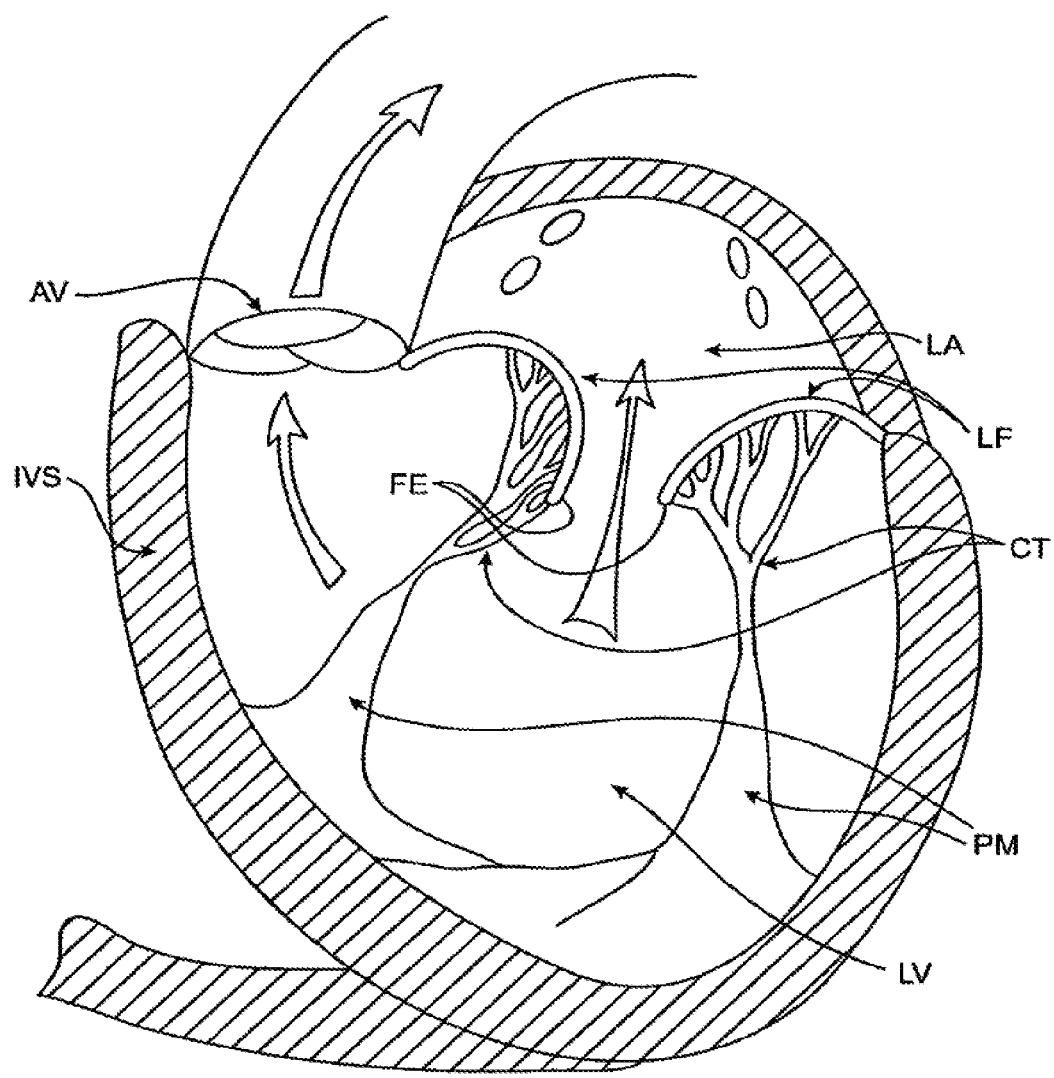
FIG. 3 is a schematic illustration of a heart in a patient suffering from cardiomyopathy where the heart is dilated and the leaflets do not meet.
Figure 4:
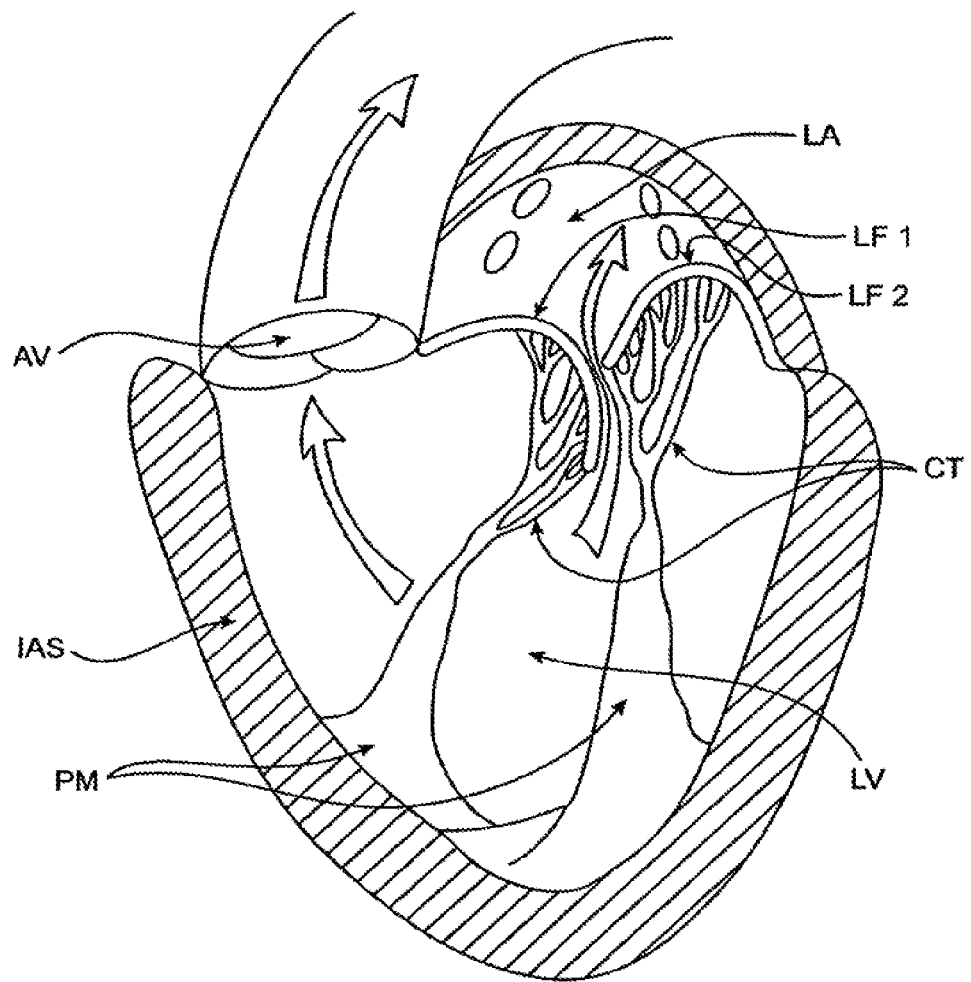
FIG. 4 illustrates mitral valve regurgitation in the left ventricle of a heart having impaired papillary muscles.

Referring now to FIGS. 2-4, a number of structural defects in the heart can cause mitral valve regurgitation. Ruptured chordae RCT, as shown in FIG. 2, can cause a valve leaflet LF2 to prolapse since inadequate tension is transmitted to the leaflet via the chordae. While the other leaflet LF1 maintains a normal profile, the two valve leaflets do not properly meet and leakage from the left ventricle LV into the left atrium LA will occur, as shown by the arrow.

Figure 3A:
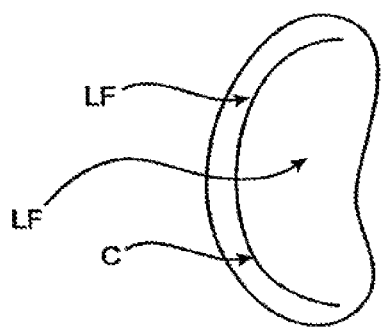
FIG. 3A shows normal closure of the valve leaflets.
Figure 3B:
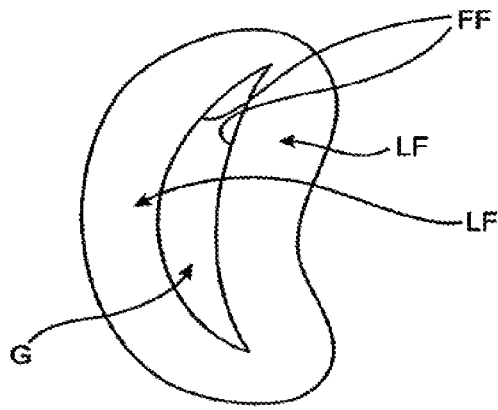
FIG. 3B shows abnormal closure of the valve leaflets.

Regurgitation also occurs in the patients suffering from cardiomyopathy where the heart is dilated and the increased size prevents the valve leaflets LF from meeting properly, as shown in FIG. 3. The enlargement of the heart causes the mitral annulus to become enlarged, making it impossible for the free edges FE to meet during systole. The free edges of the anterior and posterior leaflets normally meet along a line of coaptation C as shown in FIG. 3A, but a significant gap G can be left in patients suffering from cardiomyopathy, as shown in FIG. 3B.

Mitral valve regurgitation can also occur in patients who have suffered ischemic heart disease where the functioning of the papillary muscles PM is impaired, as illustrated in FIG. 4. As the left ventricle LV contracts during systole, the papillary muscles PM do not contract sufficiently to effect proper closure. The leaflets LF1 and LF2 then prolapse, as illustrated. Leakage again occurs from the left ventricle LV to the left atrium LA, as shown by the arrow.

Figure 5A:
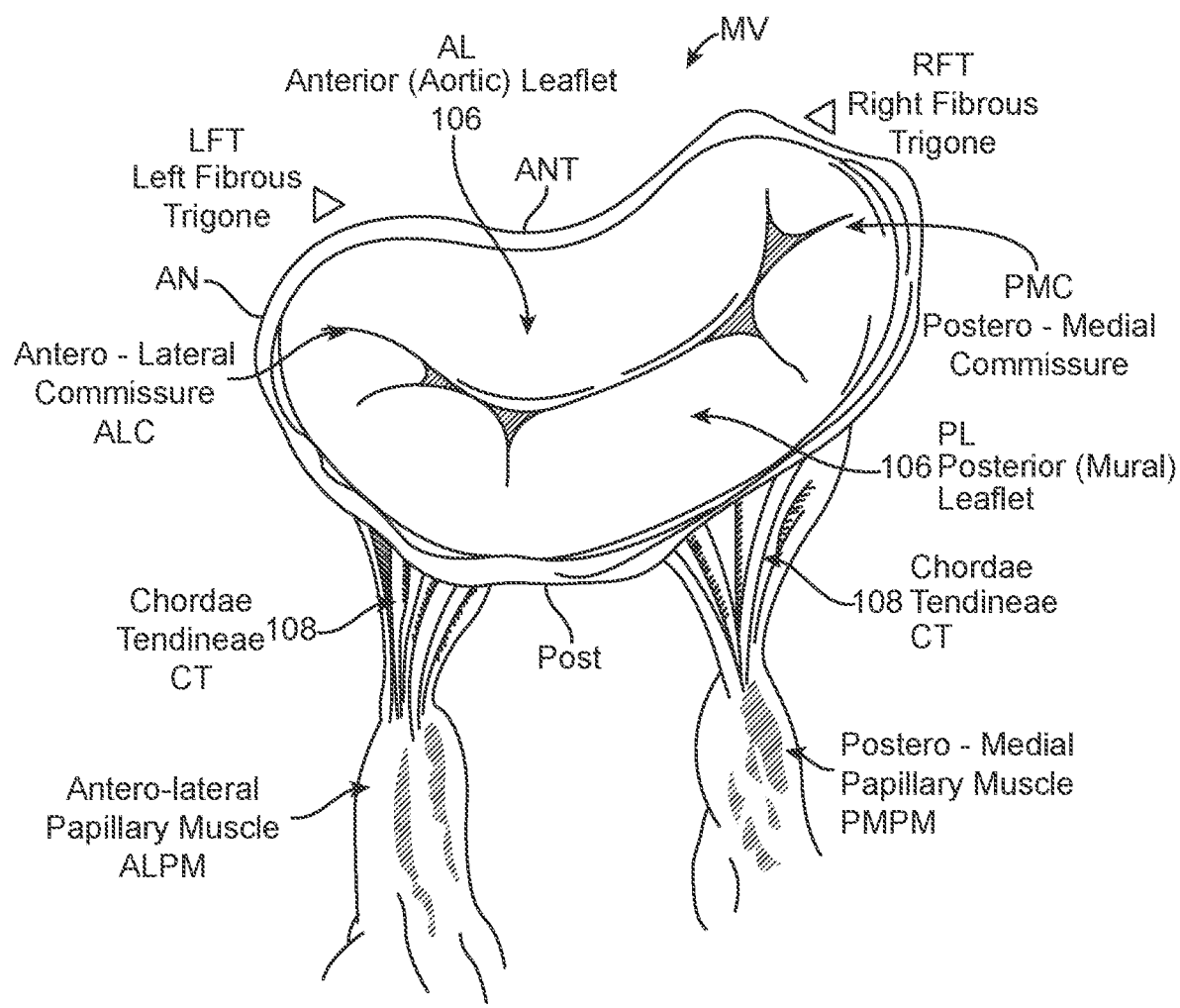
FIGS. 5A-5B illustrate anatomy of the mitral valve.
Figure 5B:
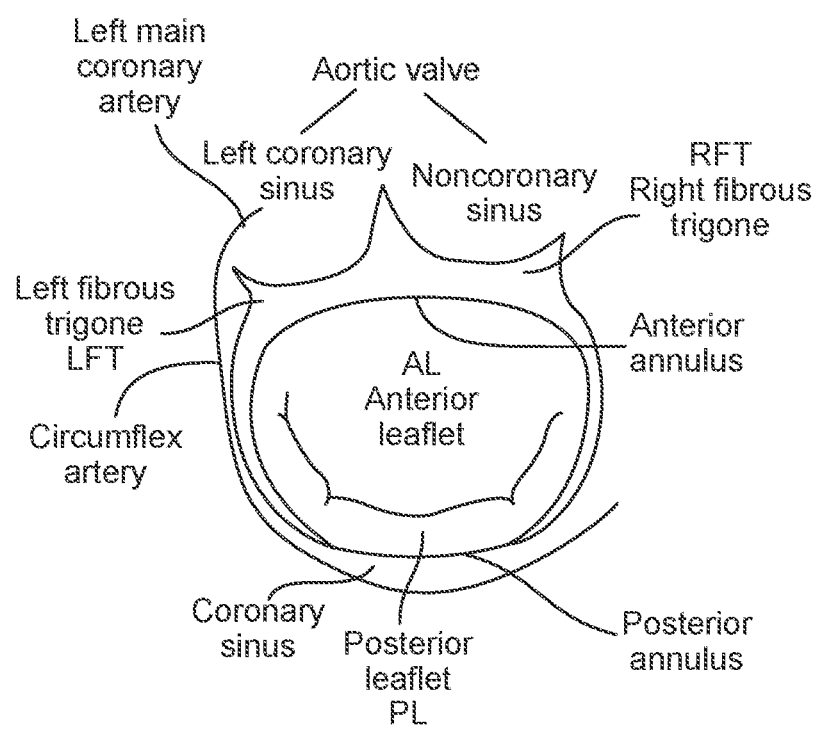

FIG. 5A more clearly illustrates the anatomy of a mitral valve MV which is a bicuspid valve having an anterior side ANT and a posterior side POST. The valve includes an anterior (aortic) leaflet AL and a posterior (mural) leaflet PL. Chordae tendineae CT couple the valve leaflets AL, PL with the antero-lateral papillary muscle ALPM and the postero-medial papillary muscle PMPM. The valve leaflets AL, PL join one another along a line referred to as the antero-lateral commissure ALC and the posterior-medial commissure PMC. The annulus AN circumscribes the valve leaflets, and two regions adjacent an anterior portion of the annulus, on opposite sides of the anterior leaflet are referred to as the left fibrous trigone LFT and also the right fibrous trigone RFT. These areas are indicted generally by the solid triangles. FIG. 5B more clearly illustrates the left and right fibrous trigones, LFT, RFT.

While various surgical techniques as well as implantable devices have been proposed and appear to be promising treatments for mitral regurgitation, surgical approaches can require a lengthy recovery period, and implantable devices have varying clinical results. Therefore, there still is a need for improved devices and methods for treating mitral regurgitation. While the embodiments disclosed herein are directed to an implantable prosthetic mitral valve for treating mitral regurgitation, one of skill in the art will appreciate that this is not intended to be limiting, and the device and methods disclosed herein may also be used to treat other cardiac valves such as the tricuspid valve, aortic valve, pulmonary valve, etc, as well as other valves in the body such as venous valves.

Prosthetic Valve. Prosthetic valves have been surgically implanted in the heart as a treatment for mitral regurgitation. Some of these valves have been valves harvested from animals such as porcine valves, and others have been prosthetic mechanical valves with or without a tissue covering. More recently, minimally invasive catheter technology has been used to deliver prosthetic valves to the heart. These valves typically include an anchor for securing the valve to the patient's heart, and a valve mechanism, either a mechanical valve, a valve with animal tissue, or combinations thereof. The prosthetic valve once implanted, takes over for the malfunctioning native valve, thereby reducing or eliminating valvar insufficiency. While some of these valves appear promising, there still is a need for improved valves. Positioning and anchoring the prosthetic valve in the native anatomy remains a challenge. The following specification discloses exemplary embodiments of a prosthetic valve, a delivery system for the prosthetic valve, and methods of delivering the valve that overcome some of the challenges associated with existing prosthetic valves.

Figure 6:
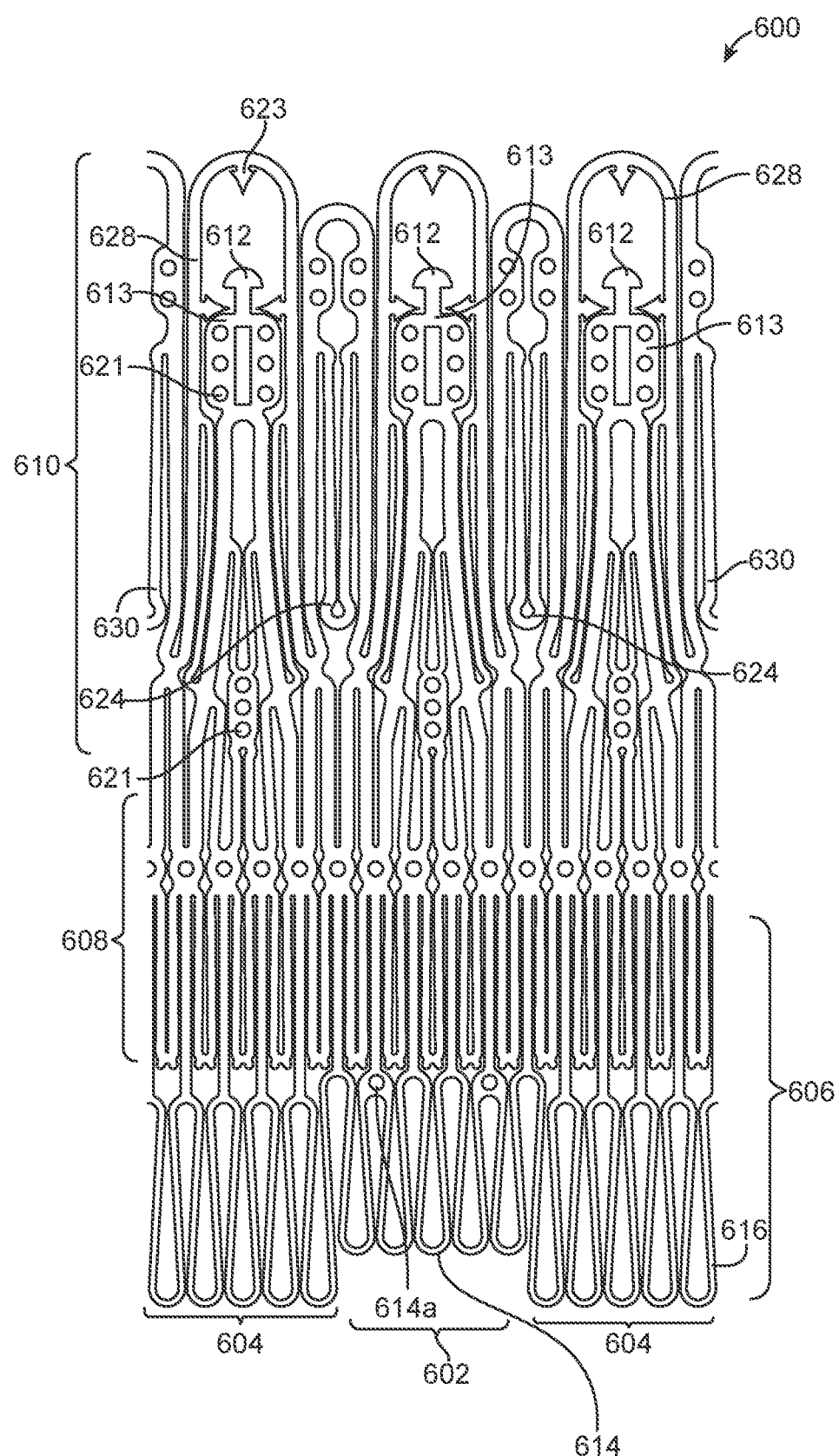
FIG. 6 illustrates an exemplary embodiment of an uncovered frame in a prosthetic cardiac valve, with the frame flattened out and unrolled.

FIG. 6 illustrates an exemplary embodiment of a prosthetic cardiac valve in the collapsed configuration. Coverings from the frame (e.g. fabric or tissue) have been removed to permit observation of the underlying frame 600. The frame has been unrolled and flattened out. The prosthetic valve frame 600 has an atrial region 606, an annular region 608, and a ventricular region 610. The frame 600 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using superelastic nitinol or other self-expanding materials. Shape memory alloys that spring open above a transition temperature may also be used, and expandable members may also be used to expand the frame when plastic deformation (e.g. balloon expansion) is required to open the frame.

Atrial region 606 has a skirt 616 which includes a plurality of interconnected struts that form a series of peaks and valleys. In this region, the struts are skewed relative to one another and thus the resulting cell pattern has an enlarged end and the opposite end tapers to a smaller end. In preferred embodiments, the anterior portion of the atrial skirt does not have a flanged region like the posterior portion, thus the anterior portion 602 of the atrial region may have shorter struts than the posterior region 604. Thus the peaks and valleys in the anterior portion are axially offset from those in the remaining posterior portion of the atrial region. This may be advantageous as it prevents the struts in the anterior portion of the atrial skirt from protruding upwards potentially impinging against the left atrium and causing perforations. Additionally, the shortened struts and offset peaks and valleys form an alignment element 614 that can assist the physician with visualization of delivery of the prosthetic valve to the mitral valve and also with alignment of the prosthetic valve prior to expansion of the prosthetic valve. Optional radiopaque markers 614*a* are disposed on either side of the offset peaks and valleys and further help with visualization during implantation of the valve. The atrial region preferably self-expands to either a cylindrical shape, or it may have a D-shaped cross-section where the anterior portion 602 is substantially flat, and the posterior portion 604 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 608 with connecting struts which are preferably linear and substantially parallel to the longitudinal axis of the frame.

The annular region 608 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded into engagement with the mitral valve annulus. Connector struts join the annular region with the ventricular region 610.

The ventricular region 610 also includes a plurality of interconnected struts that form peaks and valleys. Additionally, the struts in the ventricular region form the leaflet commissures 613 which are covered with fabric, pericardial tissue, or other materials to form the prosthetic valve leaflets. Holes in the commissures allow suture to be attached thereto. Struts in the ventricular region also form a ventricular skirt 628 which expands outward to engage the anterior and posterior mitral valve leaflets, and struts in the ventricular region also form the anterior tabs 624 and the posterior tab 630. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below.

By controlling strut length or axial position of the anterior or posterior tabs along the frame, deployment of the tabs may be controlled. Thus in this exemplary embodiment, because the length of the struts in the anterior tabs and posterior tabs 624, 630 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward. Further retraction of the constraining sheath then allows the remainder of the posterior tab to finish its radial expansion, and finally the ventricular skirt will radially expand outward. While strut lengths and axial position of the posterior tab and the ventricular skirt are similar, internal struts connect the ventricular skirt with the commissures, and this delays expansion of the ventricular skirt slightly, thus the posterior tab finishes expansion before the ventricular skirt. Using this sequence of deploying the prosthetic valve may allow the valve to be more accurately delivered and also more securely anchored into position.

Suture holes 621 are disposed along the struts of the annular region as well as the ventricular region to allow attachment of a cover such as pericardium or a polymer such as Dacron or ePTFE, or another biocompatible material. The suture holes may also be disposed along any other part of the frame. Barbs 623 are disposed along the ventricular skirt 628 to help anchor the prosthetic valve to adjacent tissue. Commissure tabs or tabs 612 are disposed on the tips of the commissures 613 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc. may be adjusted in order to provide the prosthesis with the desired mechanical properties such as stiffness, radial crush strength, commissure deflection, etc. Therefore, the illustrated geometry is not intended to be limiting.

The frame may be formed by electrical discharge machining (EDM), laser cutting, photochemical etching, or other techniques known in the art. Hypodermic tubing or flat sheets may be used to form the frame. Once the frame has been cut and formed into a cylinder (if required), it may be radially expanded into a desired geometry and heat treated using known processes to set the shape. Thus, the prosthetic valve may be loaded onto a delivery catheter in a collapsed configuration and constrained in the collapsed configuration with a constraining sheath. Removal of the constraining sheath will allow the prosthesis to self-expand into its unbiased pre-set shape. In other embodiments, an expandable member such as a balloon may be used to radially expand the prosthesis into its preferred expanded configuration by plastic deformation.

Figure 7:
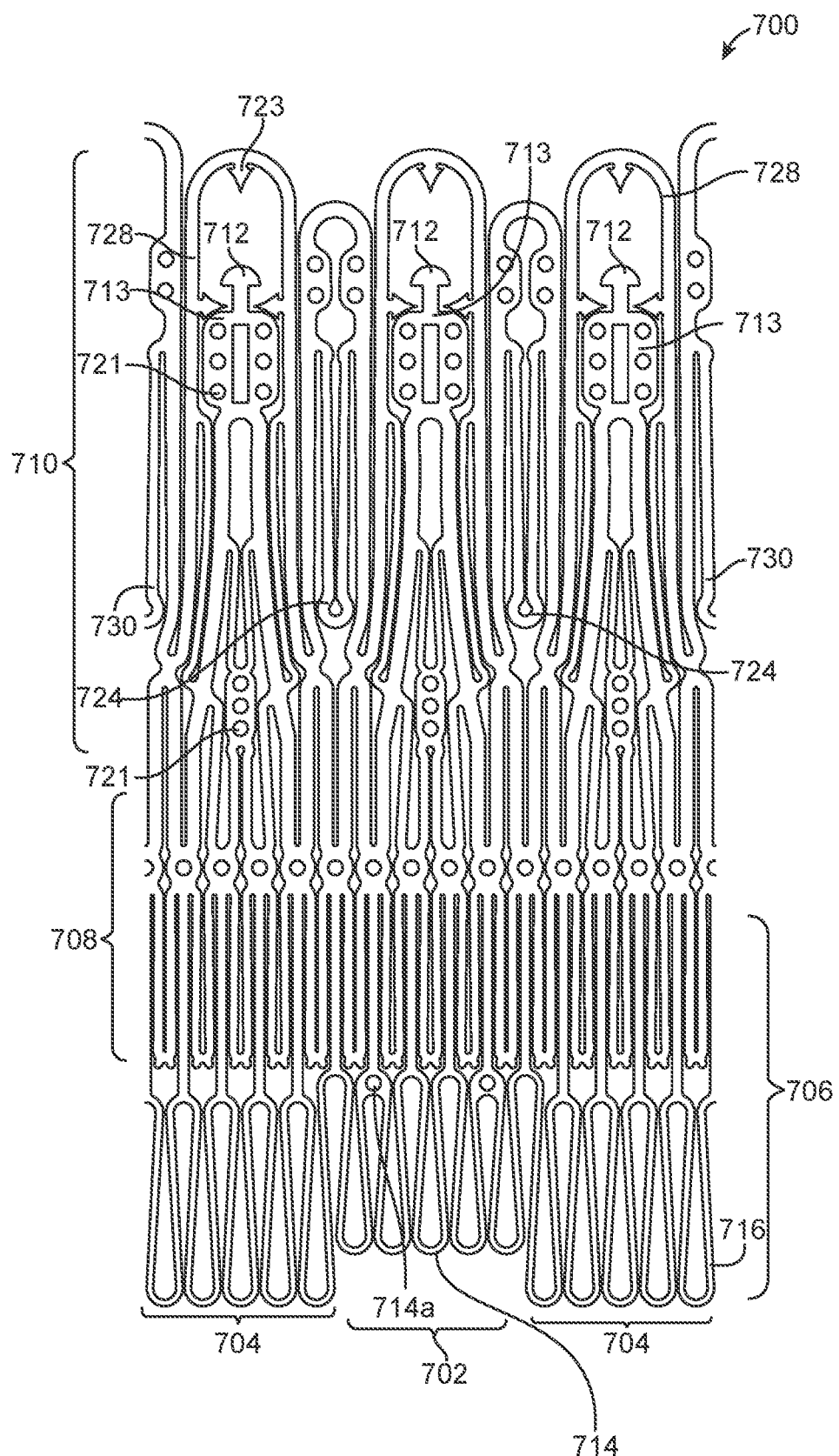
FIG. 7 illustrates another exemplary embodiment of an uncovered frame in a prosthetic cardiac valve, with the frame flattened out and unrolled.

FIG. 7 illustrates another exemplary embodiment of a prosthetic cardiac valve in the collapsed configuration, and similar to the previous embodiment with the major difference being the strut lengths in the anterior tabs, posterior tab, and ventricular skirt. Varying the strut lengths allow the sequence of expansion of the anterior and posterior tabs and ventricular skirt to be controlled. Coverings from the frame (e.g. fabric or tissue) has been removed to permit observation of the underlying frame 700. The frame has been unrolled and flattened out. The prosthetic valve frame 700 has an atrial region 706, an annular region 708, and a ventricular region 710. The frame 700 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using superelastic nitinol or other self-expanding materials. Shape memory alloys that spring open above a transition temperature may also be used, and expandable members may also be used to expand the frame when plastic deformation (e.g. balloon expansion) is required to open the frame.

Atrial region 706 has a skirt 716 which includes a plurality of interconnected struts that form a series of peaks and valleys. In this region, the struts are skewed relative to one another and thus the resulting cell pattern has an enlarged end and the opposite end tapers to a smaller end. An anterior portion 702 of the atrial region has shorter struts than the posterior region 704. Thus the peaks and valleys in the anterior portion are axially offset from those in the remaining posterior portion of the atrial region. This allows creation of an alignment element 714 to help the physician deliver the prosthetic valve to the mitral valve and align the prosthetic valve prior to expansion of the prosthetic valve. Other aspects of the atrial region 706 are similar to those of the atrial region 606 in FIG. 6. Optional radiopaque markers 714a are disposed on either side of the offset peaks and valleys and help with visualization during implantation of the valve. The atrial region preferably self-expands to either a cylindrical shape, or it may have a D-shaped cross-section where the anterior portion 702 is substantially flat, and the posterior portion 704 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 708 with connecting struts which are preferably linear and substantially parallel to the longitudinal axis of the frame.

The annular region 708 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded into engagement with the mitral valve annulus. Connector struts join the annular region with the ventricular region 710.

The ventricular region 710 also includes a plurality of interconnected struts that form peaks and valleys. Additionally, the struts in the ventricular region form the leaflet commissures 713 which are covered with fabric, pericardial tissue, or other materials to form the prosthetic valve leaflets. Holes in the commissures allow suture to be attached thereto. Struts in the ventricular region also form a ventricular skirt 728 which expands outward to engage the anterior and posterior mitral valve leaflets, and struts in the ventricular region also form the anterior tabs 724 and the posterior tab 730. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similar captures the posterior mitral valve leaflet between an inner surface of the posterior tab and an outer surface of the ventricular skirt, along with any adjacent chordae tendineae. This will be described in more detail below.

By controlling strut length or axial position of the anterior or posterior tabs along the frame, deployment of the tabs may be controlled. Thus in this exemplary embodiment, because the length of the struts in the anterior tabs and posterior tabs 724, 730 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward because they are the shortest relative to the struts in the ventricular skirt and the posterior tab. Further retraction of the constraining sheath then allows the ventricular skirt to radially expand, and finally further retraction of the sheath allows the remainder of the posterior tab to finish its radial expansion. Using this sequence of deploying the prosthetic valve may allow the valve to be more accurately delivered and also more securely anchored into position.

Suture holes 721 are disposed along the struts of the annular region as well as the ventricular region to allow attachment of a cover such as pericardium or a polymer such as Dacron or ePTFE. The suture holes may also be disposed along any other part of the frame. Barbs 723 are disposed along the ventricular skirt 728 to help anchor the prosthetic valve to adjacent tissue. Commissure tabs or tabs 712 are disposed on the tips of the commissures 713 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc. may be adjusted in order to provide the prosthesis with the desired mechanical properties such as stiffness, radial crush strength, commissure deflection, etc. Therefore, the illustrated geometry is not intended to be limiting. The frame may be formed similarly as described above with respect to FIG. 6.

Figure 8:
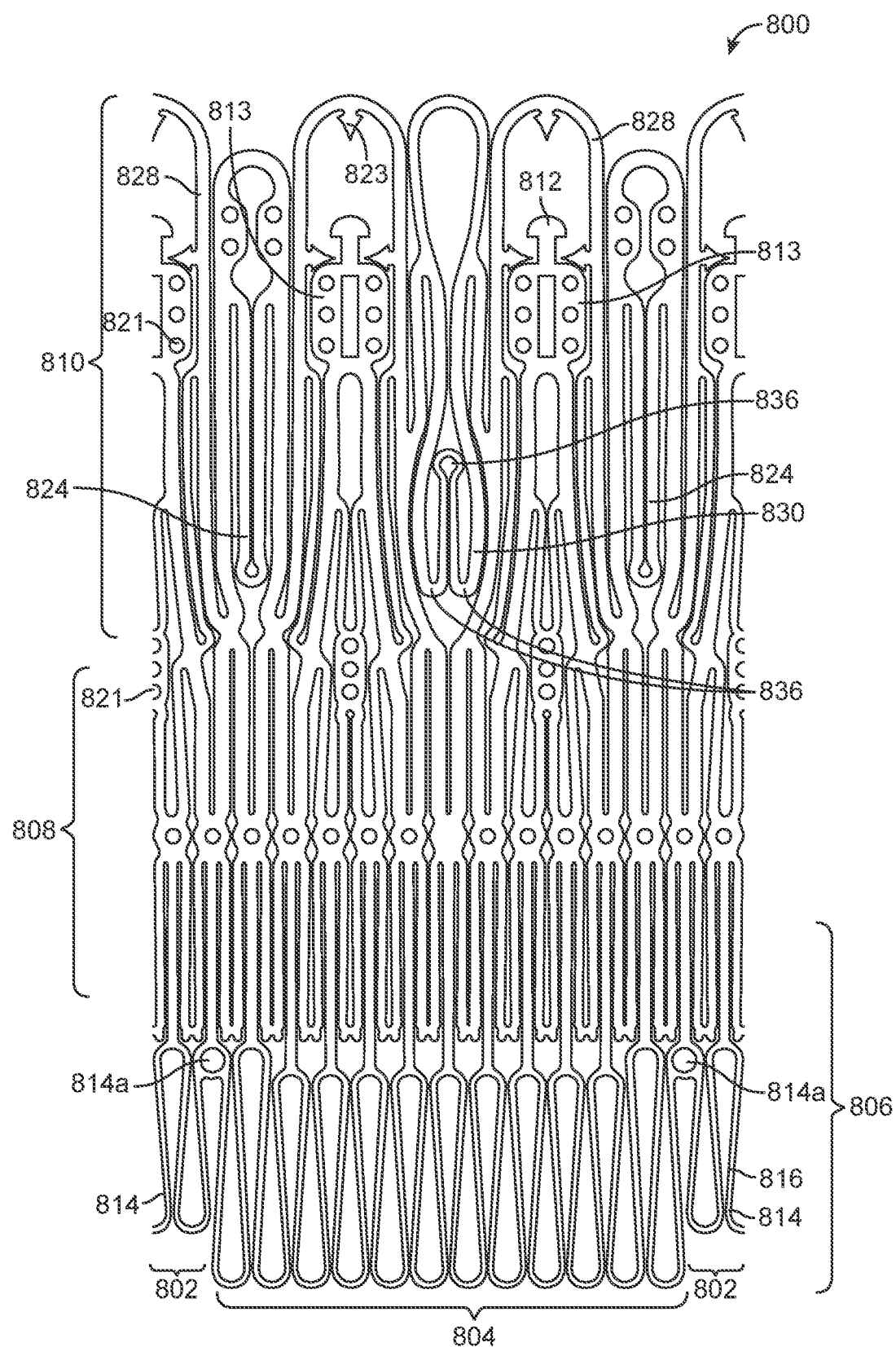
FIG. 8 illustrates still another exemplary embodiment of an uncovered frame in a prosthetic cardiac valve, with the frame flattened out and unrolled.

FIG. 8 illustrates another exemplary embodiment of a prosthetic cardiac valve in the collapsed configuration, and is similar to the previous embodiments, with the major difference being that the posterior tab is designed to expand to form an elongate horizontal section which allows engagement and anchoring of the posterior tab with the sub-annular region between the posterior leaflet and the ventricular wall. Thus, the elongate horizontal section contacts a larger region of the sub-annular region as compared with a posterior tab that only has a tapered tip formed from a single hinge between struts. This provides enhanced anchoring of the prosthetic valve. In this exemplary embodiment, the anterior tabs will completely self-expand first, followed by the posterior tab and then the ventricular skirt. However, in some situations external factors such as the delivery system, anatomy, etc. may alter the sequence of expansion, and therefore this is not intended to be limiting. Coverings from the frame (e.g. fabric or tissue) have been removed to permit observation of the underlying frame 800. The frame has been unrolled and flattened out. The prosthetic valve frame 800 has an atrial region 806, an annular region 808, and a ventricular region 810. The frame 800 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using superelastic nitinol or other self-expanding materials. Shape memory alloys that spring open above a transition temperature may also be used, and expandable members may also be used to expand the frame when plastic deformation (e.g. balloon expansion) is required to open the frame.

Atrial region 806 has a skirt 816 which includes a plurality of interconnected struts that form a series of peaks and valleys. In this region, the struts are skewed relative to one another and thus the resulting cell pattern has an enlarged end and the opposite end tapers to a smaller end. An anterior portion 802 of the atrial region has shorter struts than the posterior region 804. Thus the peaks and valleys in the anterior portion are axially offset from those in the remaining posterior portion of the atrial region. This allows creation of an alignment element 814 to help the physician deliver the prosthetic valve to the mitral valve and align the prosthetic valve prior to expansion of the prosthetic valve. Other aspects of the atrial region 806 are similar to those of the atrial region 606 in FIG. 6. Optional radiopaque markers 814a are disposed on either side of the offset peaks and valleys and help with visualization during implantation of the valve. The atrial region preferably self-expands to either a cylindrical shape, or it may have a D-shaped cross-section where the anterior portion 802 is substantially flat, and the posterior portion 804 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 808 with connecting struts which are preferably linear and substantially parallel to the longitudinal axis of the frame.

The annular region 808 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded into engagement with the mitral valve annulus. Connector struts join the annular region with the ventricular region 810.

The ventricular region 810 also includes a plurality of interconnected struts that form peaks and valleys. Additionally, the struts in the ventricular region form the leaflet commissures 813 which are covered with fabric, pericardial tissue, or other materials to form the prosthetic valve leaflets. Holes in the commissures allow suture to be attached thereto. Struts in the ventricular region also form a ventricular skirt 828 which expands outward to engage the anterior and posterior mitral valve leaflets, and struts in the ventricular region also form the anterior tabs 824 and the posterior tab 830. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below. The posterior tab is similar to the posterior tabs described above in FIGS. 6-7, except that in this embodiment, the posterior tab comprises four interconnected struts as opposed to two interconnected struts. Thus, in this embodiment the plurality of interconnected struts form three hinged regions 836 along the tab. Upon expansion of the posterior tab, the hinged regions will also expand, thereby forming an elongate horizontal section which allows engagement and anchoring of the posterior tab with the sub-annular region between the posterior leaflet and the ventricular wall. This may help position and anchor the prosthetic valve better than posterior tabs which only have a smaller footprint or a single tapered tip for engagement with the posterior portion of the mitral valve. The posterior tab in this embodiment, may be substituted with any of the other posterior tabs described in this specification.

By controlling strut length or axial position of the anterior or posterior tabs along the frame, deployment of the tabs may be controlled. Thus in this exemplary embodiment, because the length of the struts in the anterior tabs and posterior tabs 824, 830 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward because they are the shortest relative to the struts in the ventricular skirt and the posterior tab. Further retraction of the constraining sheath then allows the remainder of the posterior tab to finish self-expanding, followed by self-expansion of the ventricular skirt. Using this sequence of deploying the prosthetic valve may allow the valve to be more accurately delivered and also more securely anchored into position.

Suture holes 821 are disposed along the struts of the annular region as well as the ventricular region to allow attachment of a cover such as pericardium or a polymer such as Dacron or ePTFE. The suture holes may also be disposed along any other part of the frame. Barbs 823 are disposed along the ventricular skirt 828 to help anchor the prosthetic valve to adjacent tissue. Commissure tabs or tabs 812 are disposed on the tips of the commissures 813 and may be used to releasably couple the commissures with a delivery system as will be described below. This allows the frame to expand first, and then the commissures may be released from the delivery system afterwards. One of skill in the art will appreciate that a number of strut geometries may be used, and additionally strut dimensions such as length, width, thickness, etc. may be adjusted in order to provide the prosthesis with the desired mechanical properties such as stiffness, radial crush strength, commissure deflection, etc. Therefore, the illustrated geometry is not intended to be limiting. The frame may be formed similarly as described above.

Figure 9A:
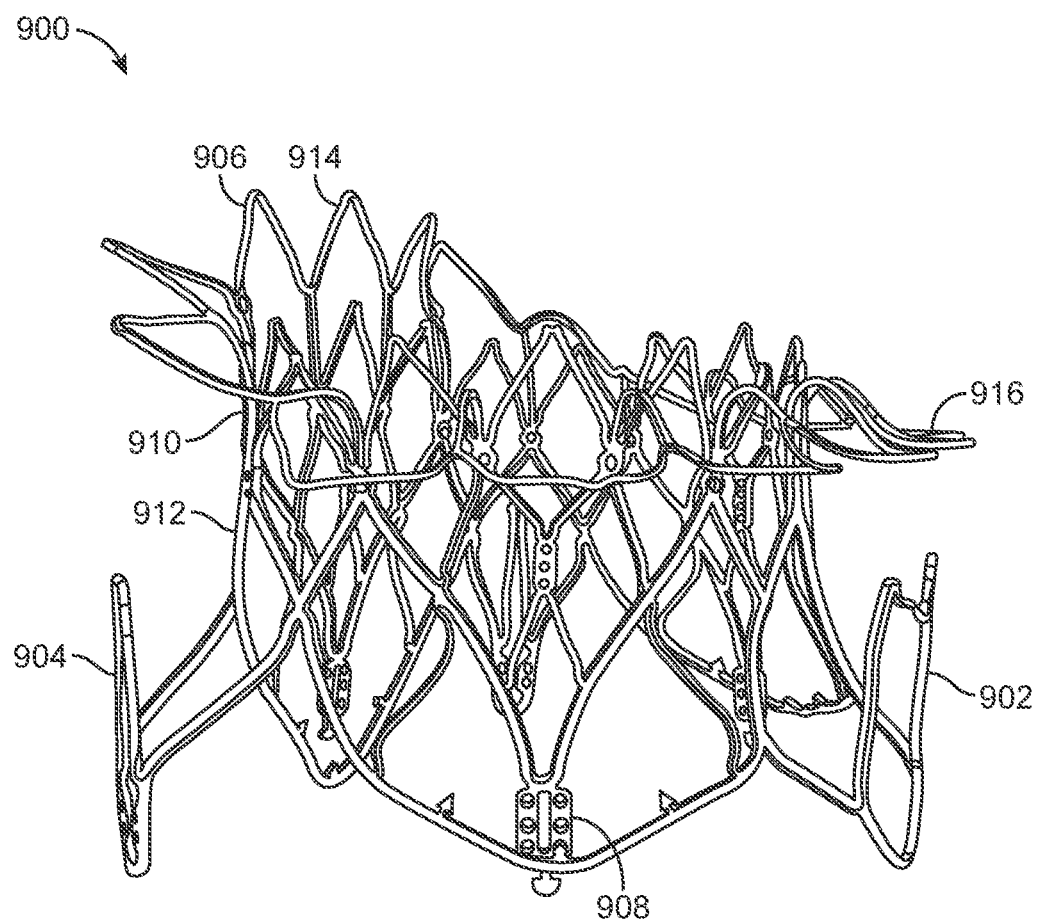
FIG. 9A illustrates a perspective view of an uncovered frame in a prosthetic cardiac valve after it has expanded.
Figure 9B:
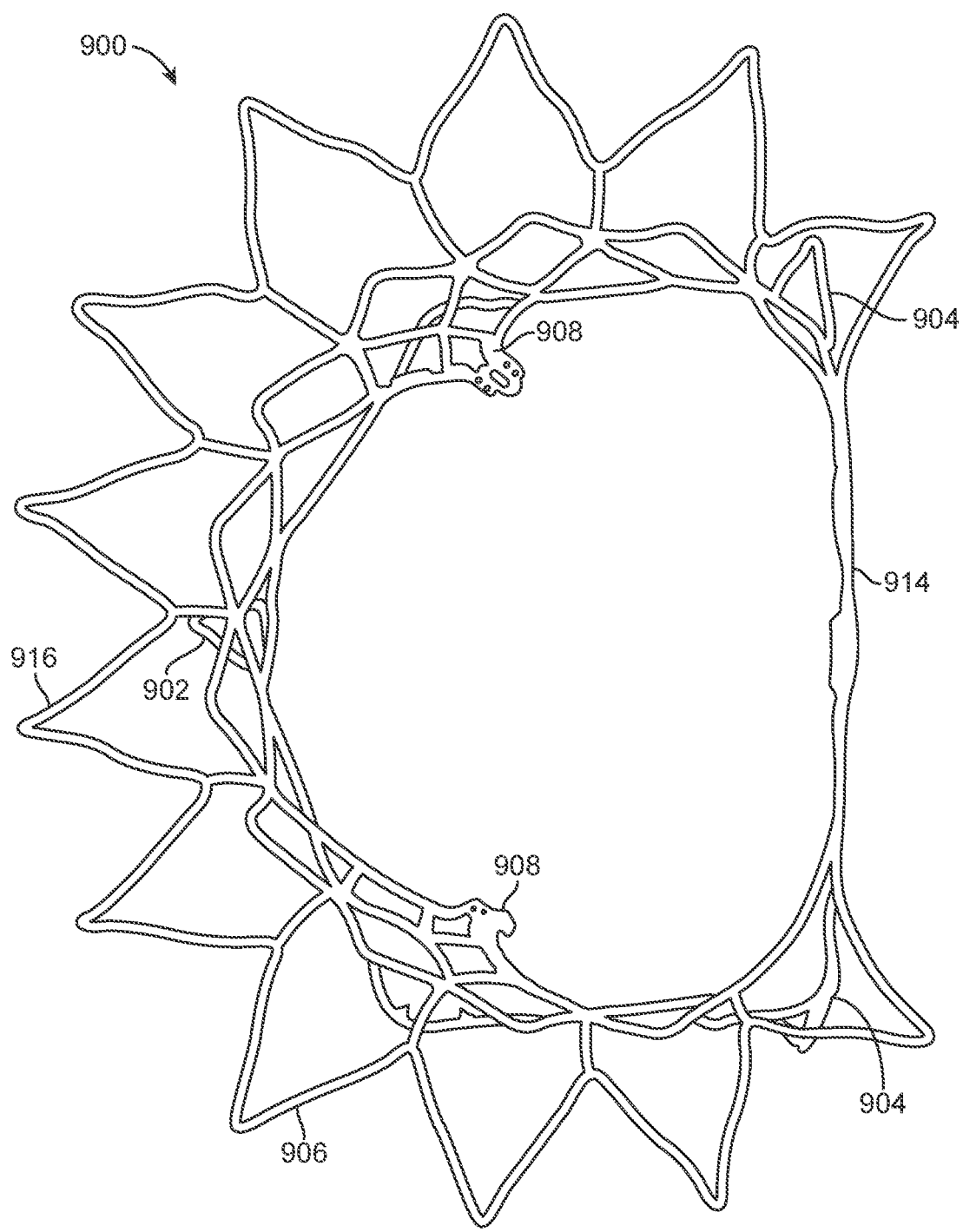
FIG. 9B illustrates a top view of the embodiment in FIG. 9A.

FIG. 9A illustrates the frame 900 of a prosthetic cardiac valve after it has expanded. Any of the frame embodiments described above may take this form as each of the above frames have similar geometry but they expand in different order. The frame includes the atrial skirt 906 with anterior portion 914 and posterior portion 916. A flanged region is formed around the posterior portion and the anterior portion remains flangeless. Additionally, the anterior portion is generally flat, while the posterior portion is cylindrically shaped, thereby forming a D-shaped cross-section which accommodates the mitral valve anatomy. FIG. 9B is a top view of the embodiment in FIG. 9A and more clearly illustrates the D-shaped cross-section.

The frame also includes the annular region 910 and ventricular skirt 912. Anterior tabs 904 (only one visible in this view) is fully expanded such that a space exists between the inner surface of the anterior tab and an outer surface of the ventricular skirt. This allows the anterior leaflet and adjacent chordae to be captured therebetween. Similarly, the posterior tab 902 is also fully deployed, with a similar space between the inner surface of the posterior tab 902 and an outer surface of the ventricular skirt. This allows the posterior leaflet and adjacent chordae tendineae to be captured therebetween. The commissure posts 908 are also visible and are disposed in the inner channel formed by the frame. The commissure posts are used to form the prosthetic mitral valve leaflets. The overall shape of the expanded frame is D-shaped, with the anterior portion flat and the posterior portion cylindrically shaped.

Figure 10:
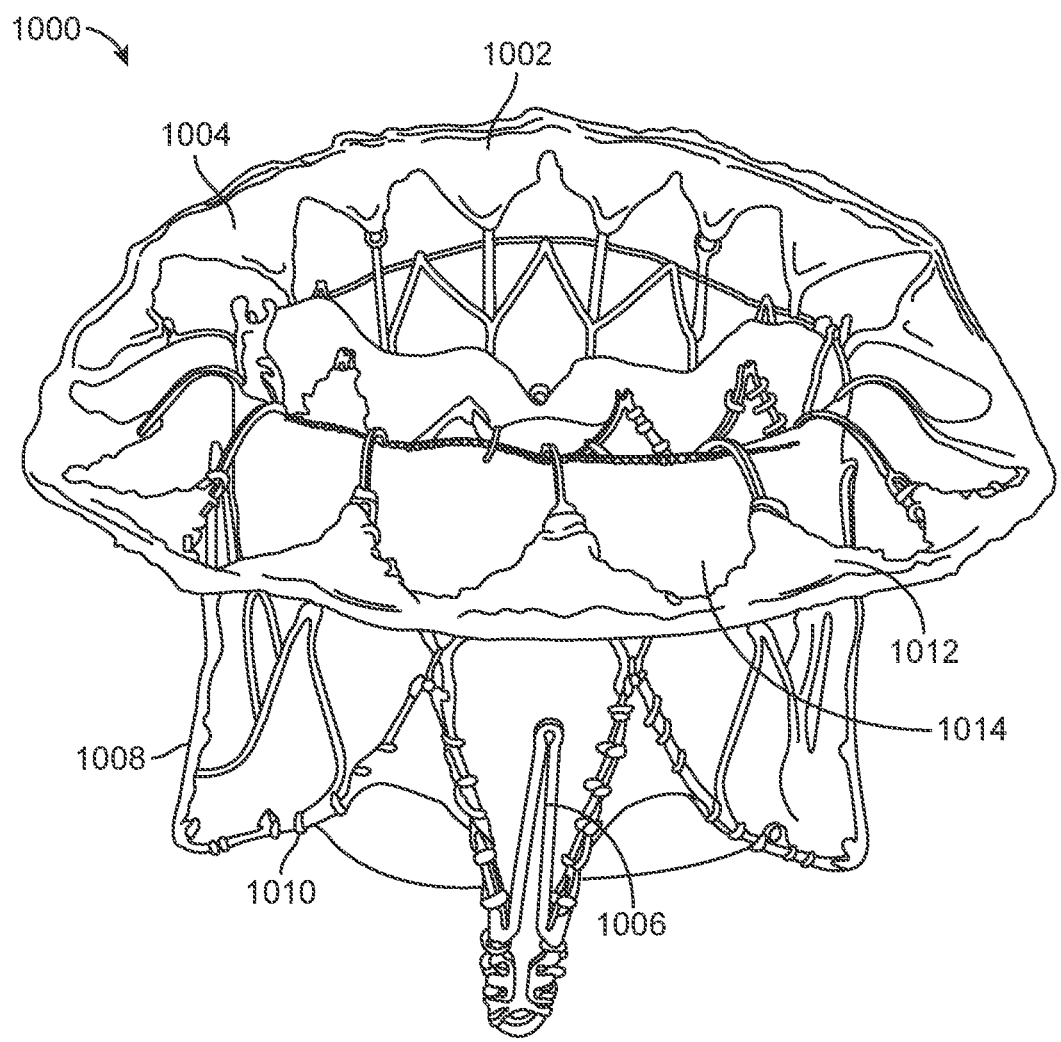
FIG. 10 illustrates the frame of FIG. 9A with the covering thereby forming a prosthetic cardiac valve.

FIG. 10 illustrates the expanded frame covered with a cover 1002 such as pericardial tissue or a polymer such as ePTFE or a fabric like Dacron attached to the frame, thereby forming the prosthetic cardiac valve 1000. The atrial skirt may be entirely covered by a material, or in preferred embodiments, the covering is only disposed between adjacent struts 1012 in adjacent cells in the flanged portion of the atrial skirt. The area 1014 between adjacent struts within the same cell remain uncovered. This allows blood flow to remain substantially uninterrupted while the prosthetic valve is being implanted. Suture 1010 may be used to attach the cover to the frame. In this view, only the posterior tab 1006 is visible on the posterior portion of the prosthetic valve along with ventricular skirt 1008 and atrial skirt 1004.

Anti-Pivoting Mechanism

Figure 15:
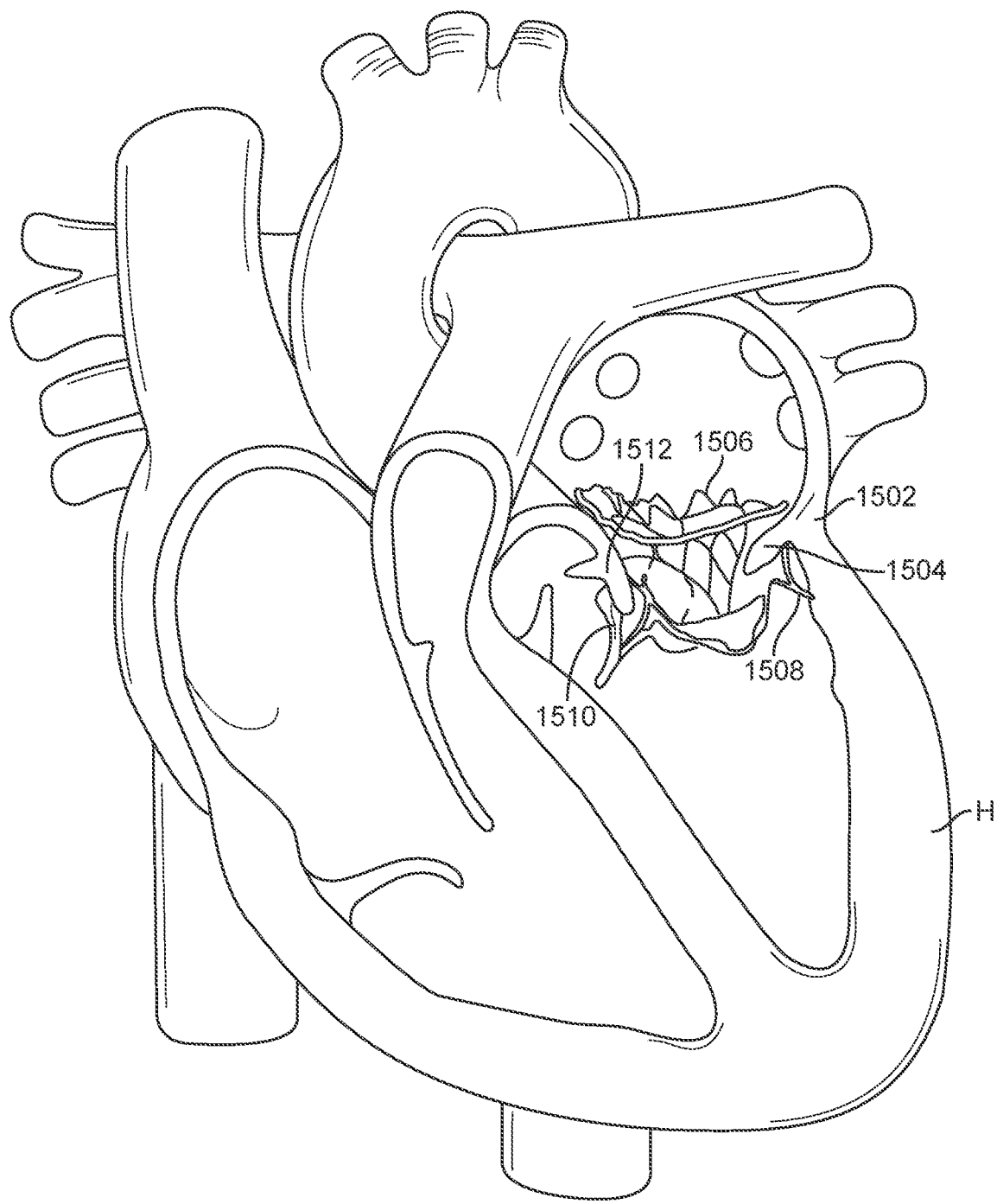
FIG. 15 illustrates a preferred positioning of a prosthetic valve in a native mitral valve.

As discussed above, preferred embodiments of the device anchor the prosthetic valve to the anterior and posterior valve leaflets. FIG. 15 illustrates an example of this where the prosthetic valve 1506 which may be any of the embodiments having both anterior and posterior tabs described herein, is successfully anchored to the mitral valve 1502 of a patient's heart H. The posterior tab 1508 has successfully engaged the posterior leaflet 1504, and the anterior tab 1510 has successfully engaged the anterior leaflet 1512. Proper anterior and posterior anchoring secures the inferior portion of the prosthetic valve and prevents unwanted rotation or pivoting of the prosthetic valve, as well as preventing unwanted axial movement upstream or downstream. However, as previously discussed, in certain situations the posterior tab may not anchor the prosthetic device to the posterior leaflet of native valve. For example, if the physician improperly delivers and deploys the prosthetic valve it may not properly engage the posterior leaflet. Or, in some situations, the posterior leaflet may have an irregular shape or may be fragile and therefore not be strong enough for anchoring with the posterior tab.

Figure 16:
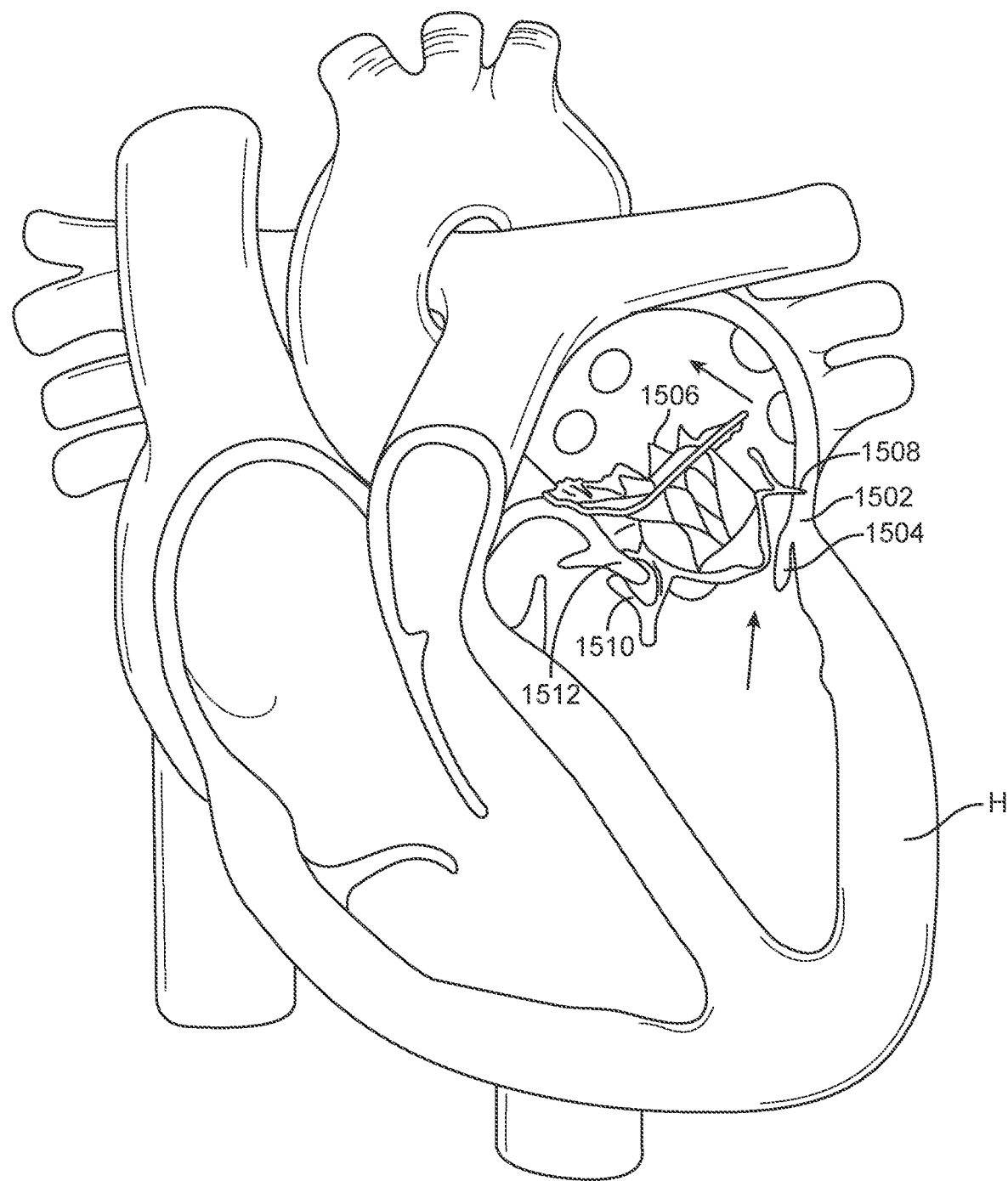
FIG. 16 illustrates dislodgement of a prosthetic valve from a native valve.

When the posterior tab fails to anchor the prosthetic valve to the posterior leaflet, the prosthetic valve will only be anchored with the anterior tabs and therefore may pivot or rotate counter-clockwise, or upward into the left atrium as seen in FIG. 16 which illustrates the prosthetic valve 1506 rotating due to the retrograde blood pressure from the left ventricle of the heart H and exerted on the prosthesis during systole. The posterior portion of the prosthesis pivots upward into the left atrium creating a leak around the prosthesis as indicated by the arrows.

Figure 17:
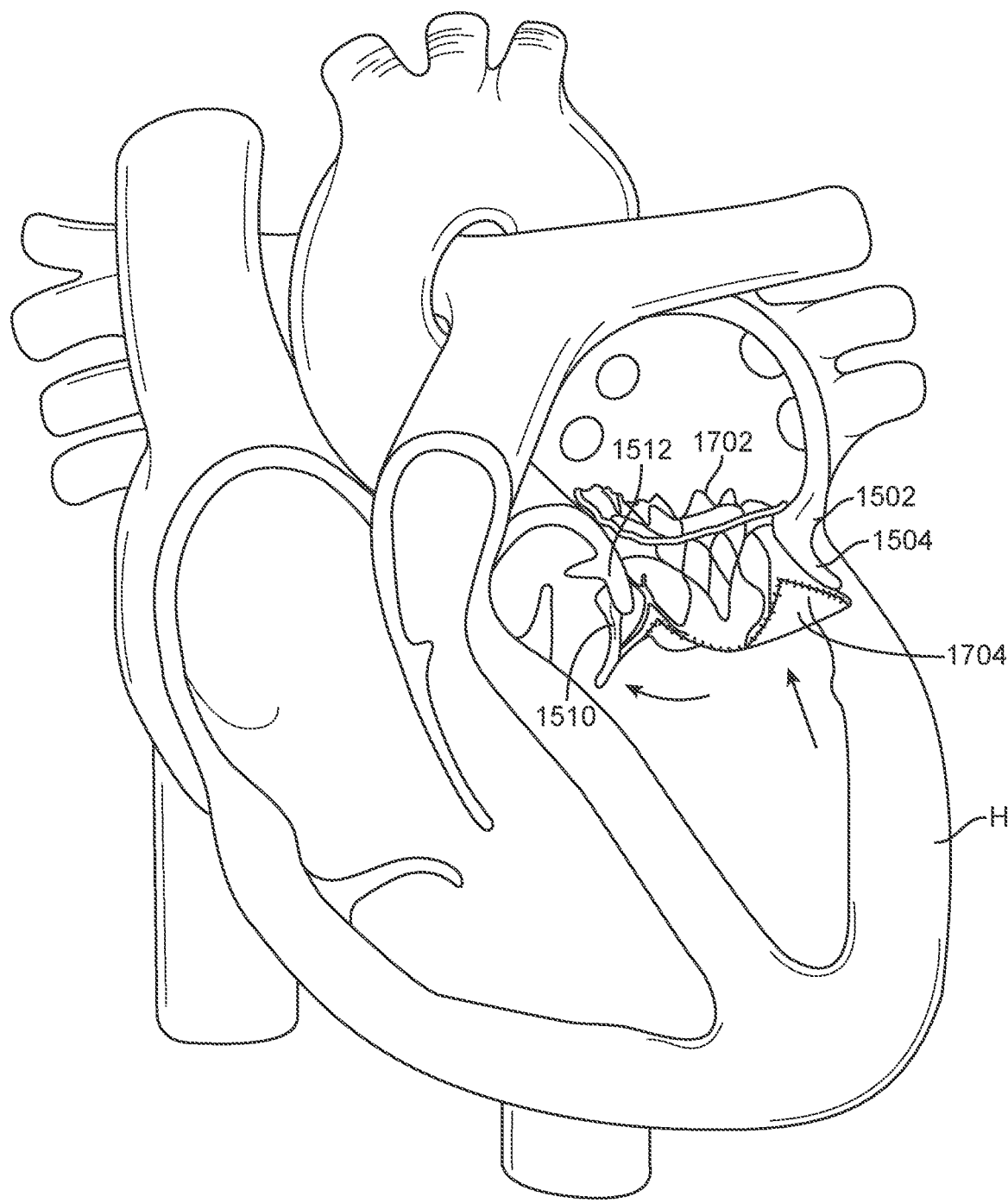
FIG. 17 illustrates an alternative embodiment of a prosthetic valve anchored to a native valve.

FIG. 17 illustrates an alternative embodiment of prosthetic valve that helps prevent posterior pivoting. The prosthetic valve 1702 in this embodiment is a prosthetic mitral valve and it is implanted in a native mitral valve 1502 of a patient's heart H. The prosthetic valve 1702 generally takes the same form as other prosthetic valves described in this specification, with the major exception that it does not have posterior tabs. Instead of the posterior tabs, the prosthetic valve includes a foot 1704 which prevents pivoting. The foot is an enlarged portion of the prosthetic valve that extends radially outward from the body of the prosthesis sufficiently far so that the cross-sectional area of the ventricular portion of the prosthetic valve is large enough to prevent it from pivoting or rotating up into the atrium. Thus, blood flows out the left ventricle into the aorta during systole and retrograde flow into the atrium is eliminated or substantially reduced. Leaks around the prosthetic valve are also reduce or eliminated. The foot may be any number of structures which prevent pivoting of the prosthesis.

Figure 18A:
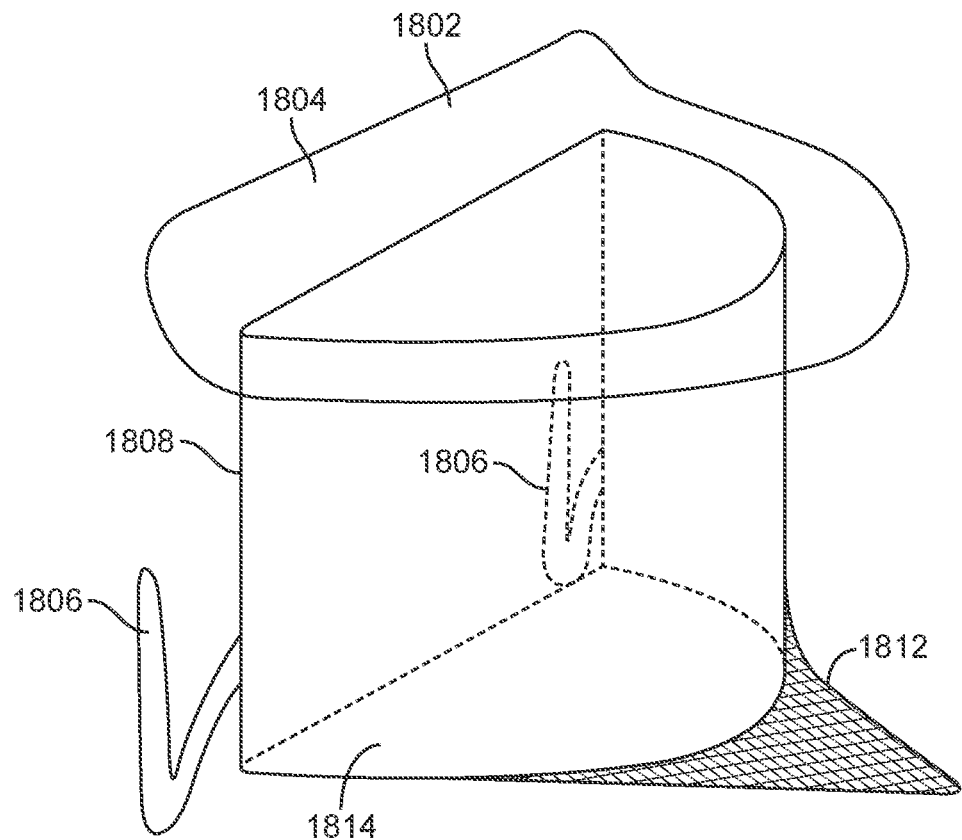
FIGS. 18A-18B illustrate a schematic diagram of a prosthetic valve with an anti-pivoting mechanism.
Figure 18B:
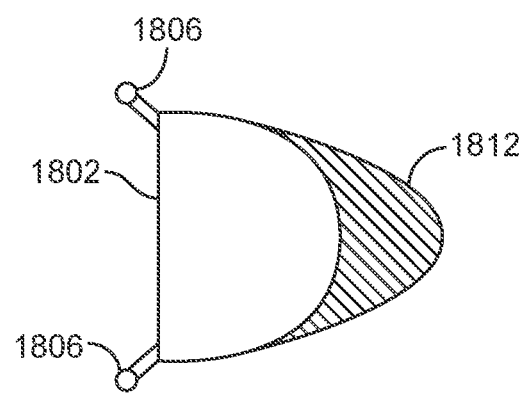

FIGS. 18A-18B illustrate a schematic of a prosthetic valve having an anti-pivoting mechanism. FIG. 18A illustrates the prosthetic valve 1802 which is generally the same as any of the other valve embodiments described herein with the major difference being that it does not have a posterior tab. The prosthetic valve 1802 may have any of the features described in any other embodiments disclosed herein. For example, the prosthetic valve may include an atrial flange 1804, an annular region 1808 and a ventricular region or ventricular skirt 1814. The valve preferably also includes two anterior tabs 1806 for engaging the anterior leaflet and the trigones. Also, the valve has a foot 1812 which is a wedge shaped region of the prosthesis that extends radially outward. FIG. 18B illustrates a top view of the prosthetic valve 1802 seen in FIG. 18A.

Figure 18C:
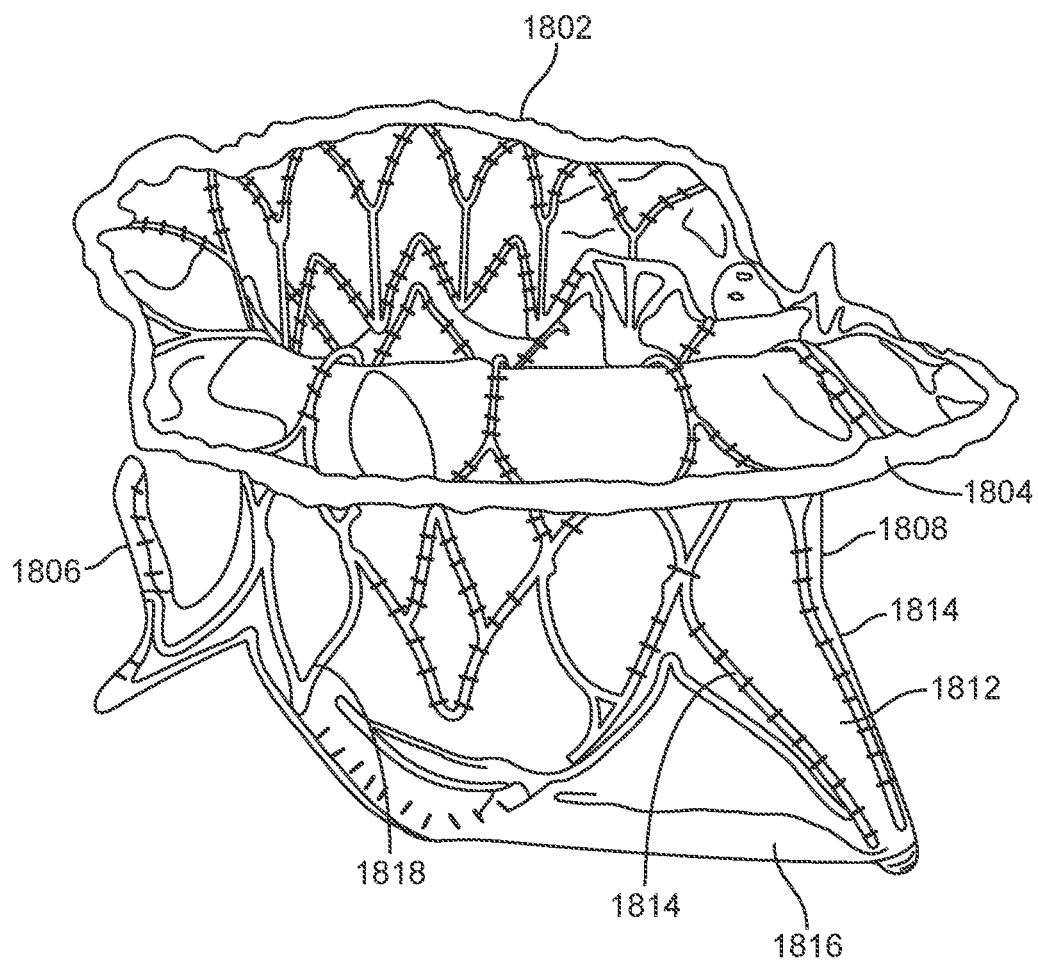
FIG. 18C illustrates a perspective view of a prosthetic valve with an anti-pivoting mechanism.

FIG. 18C illustrates a perspective view of a prosthetic valve 1802 that generally takes the same form as other valve embodiments described herein with the major difference being that instead of having a posterior tab for anchoring to a valve leaflet, the valve has a foot 1812 which anchors the posterior part of the valve to the posterior portion of the native valve. The valve includes an atrial flange 1804, anterior trigonal tabs 1806, an annular region 1808, and a ventricular skirt region 1818 that generally take the same form as described in other embodiments. The foot 1812 may be any structure which extends radially outward and prevents the prosthetic valve from rotating or pivoting. In some embodiments, the foot may extend radially outward 10 mm or more. In this embodiment, the foot includes a central element 1812 which has been formed from two struts 1814 that are coupled together with a connector to form a V or U-shaped structure that extends radially outward. A cover 1816 such as pericardial tissue, or any of the other cover materials discussed herein is attached to the central element 1812 and to adjacent struts on either side, thereby forming a vestibule similar to that seen on a camping tent, or a cattle pusher on a locomotive engine (sometimes referred to as a pilot). This structure has a larger cross-section than the native valve, and thus it prevents the prosthetic valve from rotating through the valve into the atrium (in the case of a mitral valve prosthesis).

Figure 19:
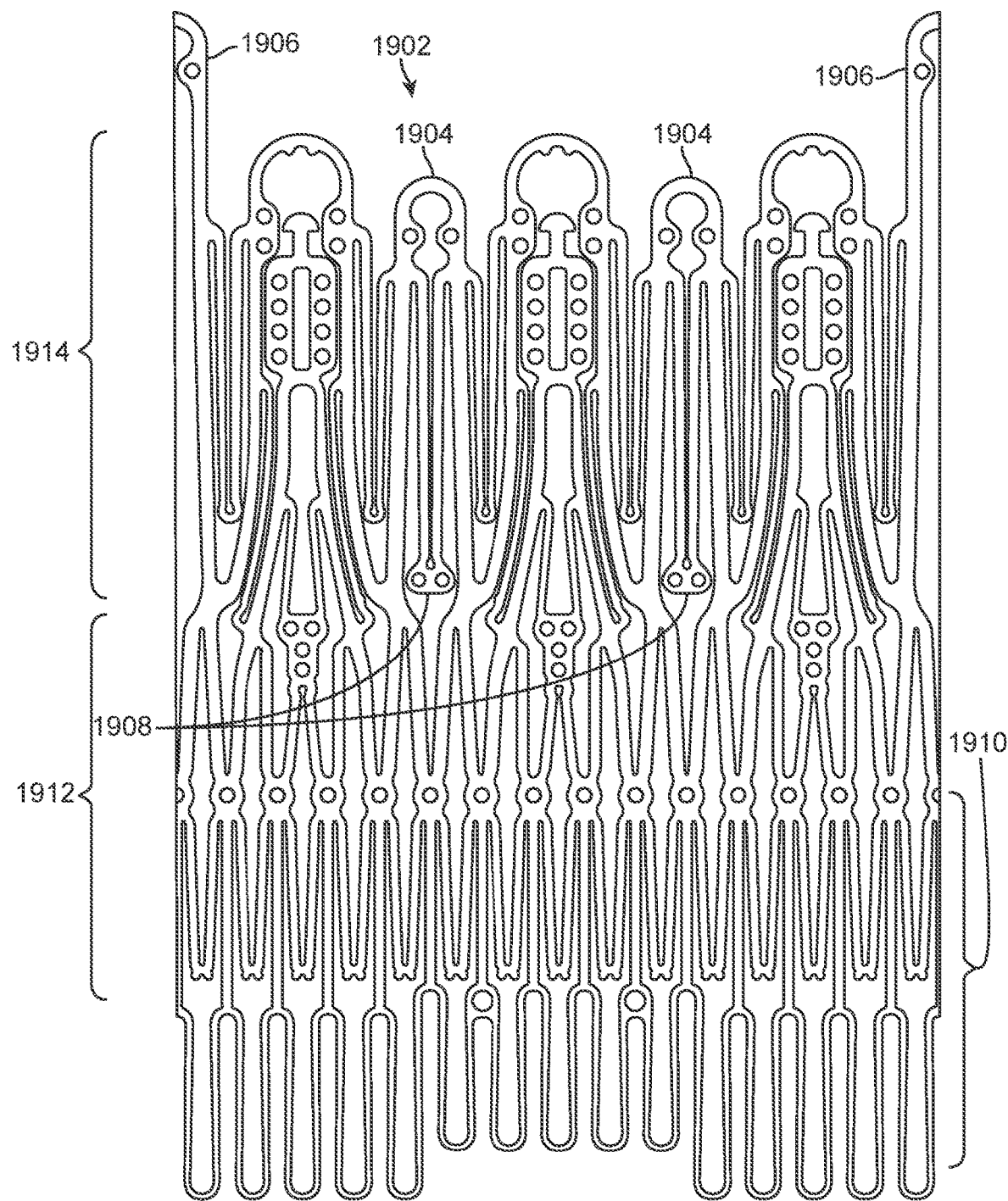
FIG. 19 illustrates an exemplary embodiment of an uncovered prosthetic valve flattened out and unrolled.

FIG. 19 illustrates a flat pattern used to cut the prosthetic valve from tubing or a flat sheet which is then rolled and welded into a cylinder. Electrical discharge machining (EDM), laser cutting, or photochemical etching are techniques that may be used to cut the flat pattern. The prosthesis 1902 generally takes the same form as other prosthetic valves disclosed herein, and thus not every feature will be described in detail. The prosthesis 1902 includes an atrial region 1910 having an atrial skirt, an annular region 1912 and a ventricular region 1914. The ventricular region includes anterior tabs 1904 with tips 1908 that engage the fibrous trigones on either side of the anterior leaflet of a mitral valve. The anti-pivoting mechanism is formed from an elongate pair of struts 1906 which extend axially further than the struts of the ventricular region. The struts 1906 may be formed to flare radially outward upon self-expansion and they may be covered with tissue or synthetic material to form the enlarged area of the foot which prevents pivoting. Other aspects of the prosthetic valve such as the atrial flange, the annular region, the ventricular skirt, suture holes, commissure posts, commissure tabs, alignment element, flat anterior shape, cylindrical posterior shape, D-shaped cross-section may generally take the same form as described in other embodiments of this specification. The prosthetic valve is preferably formed from shape memory or super-elastic nitinol, or it may be made from other self-expanding materials known in the art. The valve may also be balloon expandable and be made from materials such as stainless steel, cobalt-chromium, or other materials known in the art. The foot may take any number of shapes and may be a combination of metal or fabric and/or polymer features integral with or coupled to the prosthetic valve. The anchoring elements on the prosthetic valve may be deployed in any desired order. However, in preferred embodiments, the atrial skirt deploys first and anchors the valve to the atrial floor followed by deployment of the annular region into the annulus, then the anterior tabs capture the valve leaflets, followed by the foot, and then the ventricular skirt, and then the commissures.

Figure 20A:
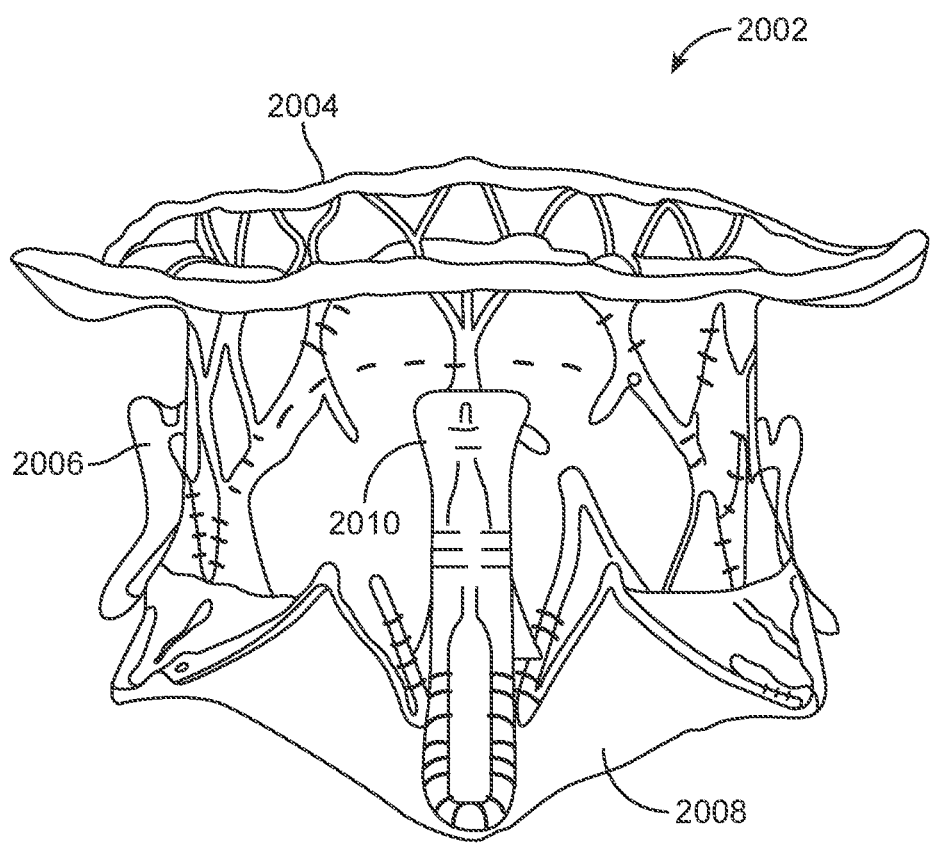
FIGS. 20A-20B illustrate another exemplary embodiment of a prosthetic valve having an anti-pivoting mechanism and a posterior tab.
Figure 20B:
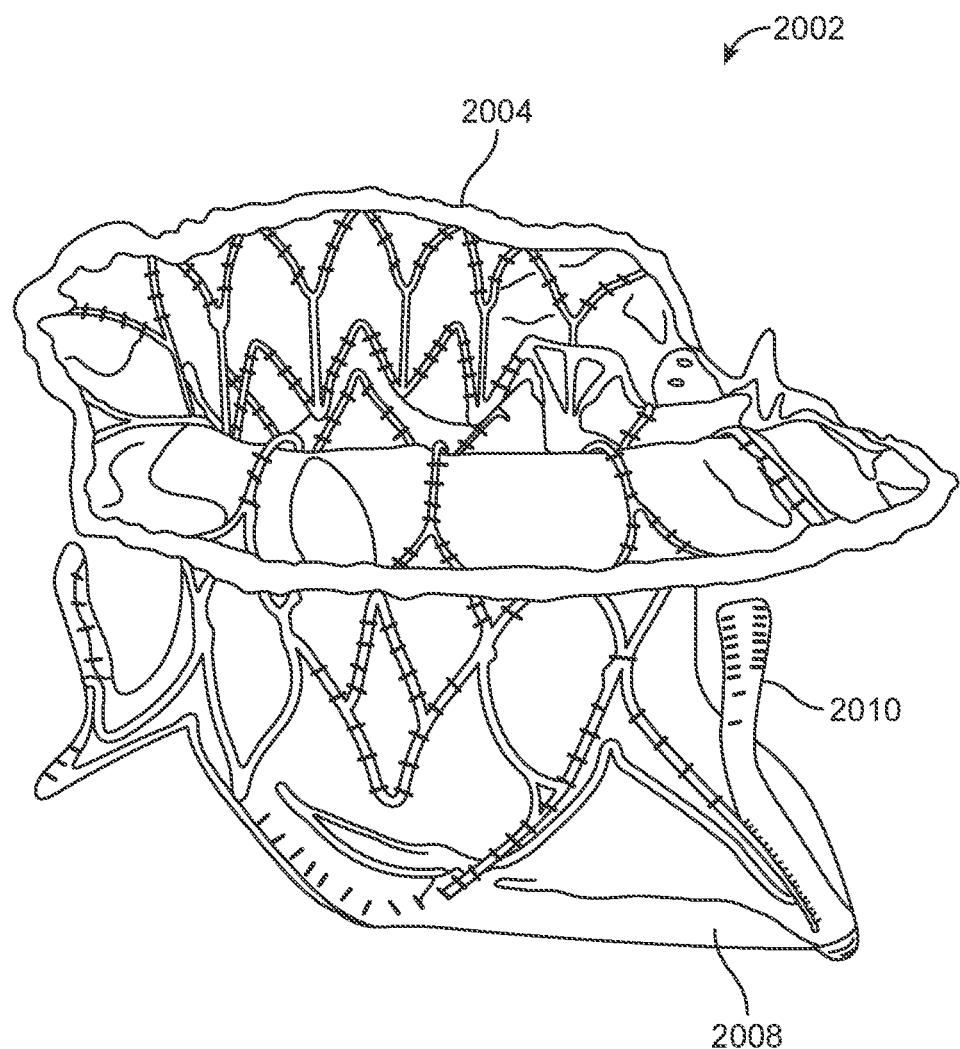

FIGS. 20A-20B illustrate another exemplary embodiment of a prosthetic valve combining features of several previously disclosed embodiments such as the foot and a posterior tab. FIG. 20A illustrates a rear view looking head on at a prosthetic valve 2002 which may take the form of any of the embodiments disclosed herein. The upper end of the prosthesis includes an atrial flange 2004 which helps anchor the device to the floor of the atrium as previously described. The prosthesis also includes a pair of anterior trigonal tabs for anchoring the prosthesis to the fibrous trigones of the anterior portion of the valve annulus. The posterior portion of the prosthesis includes a foot 2008 like the foot previously described above, and a posterior tab 2010 which may take the form of any of the previous embodiments. Other portions of the prosthesis may take the form of any previous embodiment described herein, including but not limited to the annular region, ventricular region, commissures, etc. Having both a posterior tab and a foot provides a fail safe anchoring mechanism on the prosthesis. Thus, in case the posterior tab fails to anchor the device to the posterior portion of the valve, the foot anchors the device as described before and prevents unwanted pivoting of the prosthesis upward toward the left atrium. FIG. 20B illustrates another side view of the prosthesis 2020, this time rotated about its longitudinal axis to more clearly illustrate one anterior tab (the other is obstructed), as well as the foot and the posterior tab. In addition to having a posterior tab and a foot, alternative embodiments may also have barbs, texturing or other surface features on the foot, the posterior tab, or adjacent thereto in order to help further anchor the prosthesis into the tissue.

Figure 21:
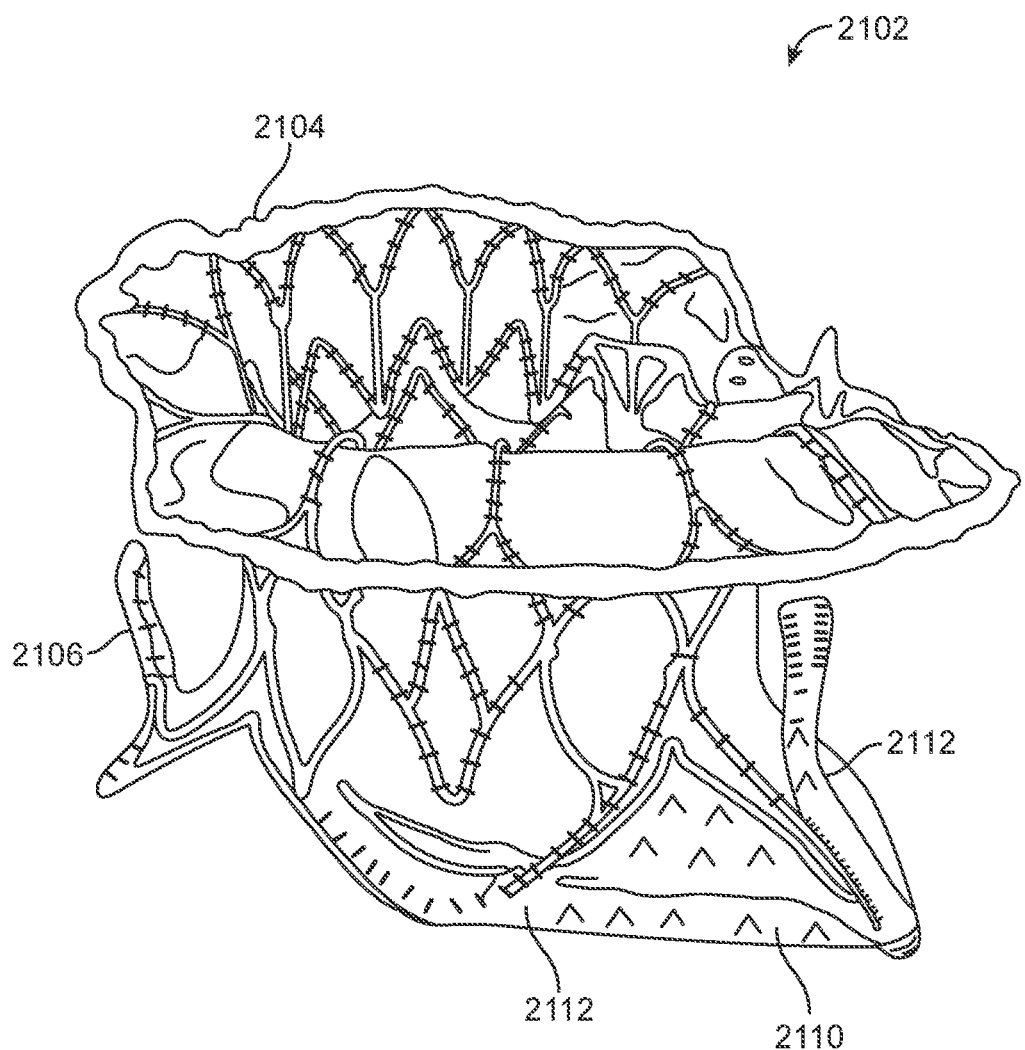
FIG. 21 illustrates an exemplary embodiment of a prosthetic valve having an anti-pivoting mechanism with a posterior tab, and barbs.

FIG. 21 illustrates an exemplary embodiment of a prosthesis 2102 having a foot 2110, posterior tab 2106, anterior tab 2106 and barbs 2112. The barbs may be pointed protrusions, or they may be textured regions. They may be disposed on the foot, on the posterior tab, or on both portions of the device. Other aspects of the prosthesis such as the atrial flange 2104, anterior tab 2106, as well as other features including the annular skirt, ventricular skirt, commissures, etc. may take the form of any embodiment described herein.

Delivery System. FIGS. 11A-11D illustrate an exemplary embodiment of a delivery system that may be used to deliver any of the prosthetic valves disclosed in this specification. While the delivery system is designed to preferably deliver the prosthetic valve transapically, one of skill in the art will appreciate that it may also be modified so that the prosthetic valve may be delivered via a catheter transluminally, such using a transseptal route. One of skill in the art will appreciate that using a transseptal route may require the relative motion of the various shafts to be modified in order to accommodate the position of the delivery system relative to the mitral valve.

Figure 11A:
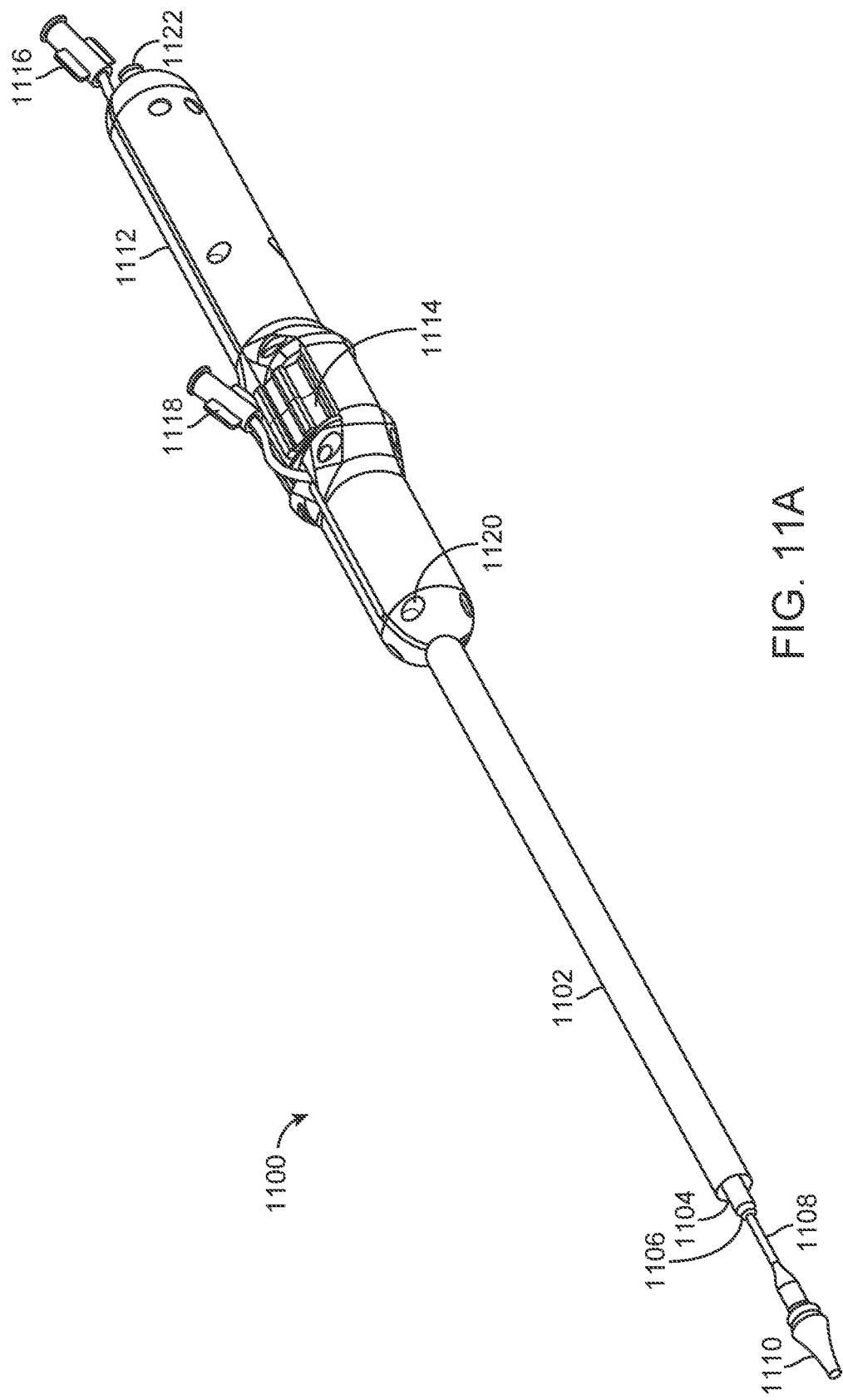
FIGS. 11A-11D illustrate an exemplary embodiment of a delivery system used to transapically deliver a prosthetic cardiac valve.
Figure 11B:
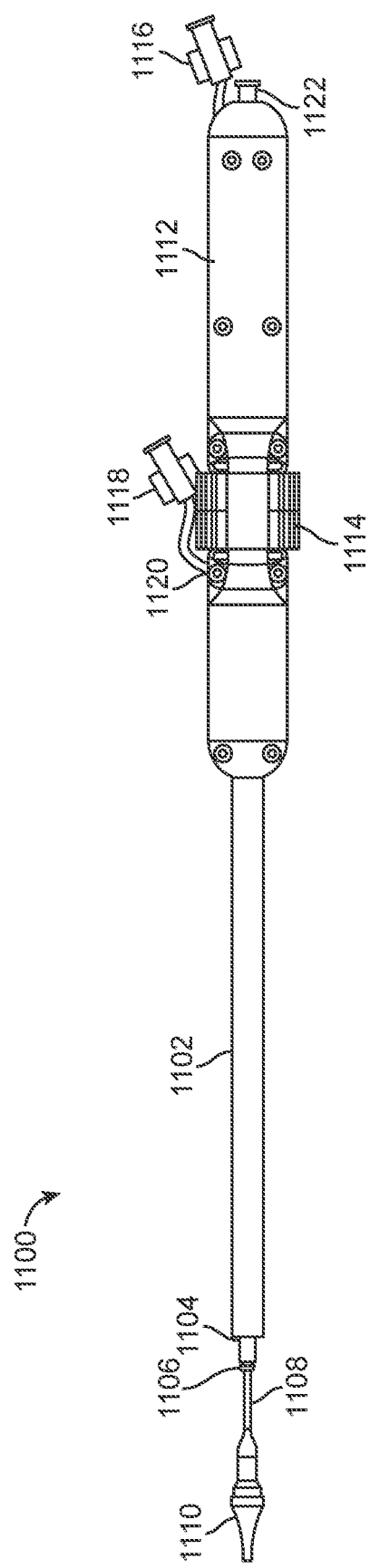

FIG. 11A illustrates a perspective view of delivery system 1100. The delivery system 1100 includes a handle 1112 near a proximal end of the delivery system and a distal tissue penetrating tip 1110. Four elongate shafts are included in the delivery system and include an outer sheath catheter shaft 1102, a bell catheter shaft 1104 which is slidably disposed in the outer sheath catheter shaft 1102, a hub catheter shaft 1106 which remains stationary relative to the other shafts, but the bell catheter shaft slides relative to the hub shaft, and finally an inner guidewire catheter shaft 1108 which is also fixed relative to the other shafts and has a lumen sized to receive a guidewire which passes therethrough and exits the distal tissue penetrating tip. An actuator mechanism 1114 is used to control movement of the various shafts as will be explained in greater detail below, and flush lines 1116, 1118 with luer connectors are used to flush the annular regions between adjacent shafts. Flush line 1118 is used to flush the annular space between the outer sheath catheter shaft 1102 and the bell catheter shaft 1104. Flush line 1116 is used to flush the annular space between the bell catheter 1104 and the hub catheter 1106. The inner guidewire catheter shaft 1108 is stationary relative to the hub catheter 1106 therefore the annular space may be sealed with an o-ring or other material. Luer connector 1122 allows flushing of the guidewire lumen and a hemostatic valve such as a Tuohy-Borst may be coupled to the luer connector to allow a guidewire to be advanced through the guidewire catheter shaft while maintaining hemostasis. Screws 1120 keep the handle housing coupled together. FIG. 11B illustrates a side view of the delivery system 1100.

Figure 11C:
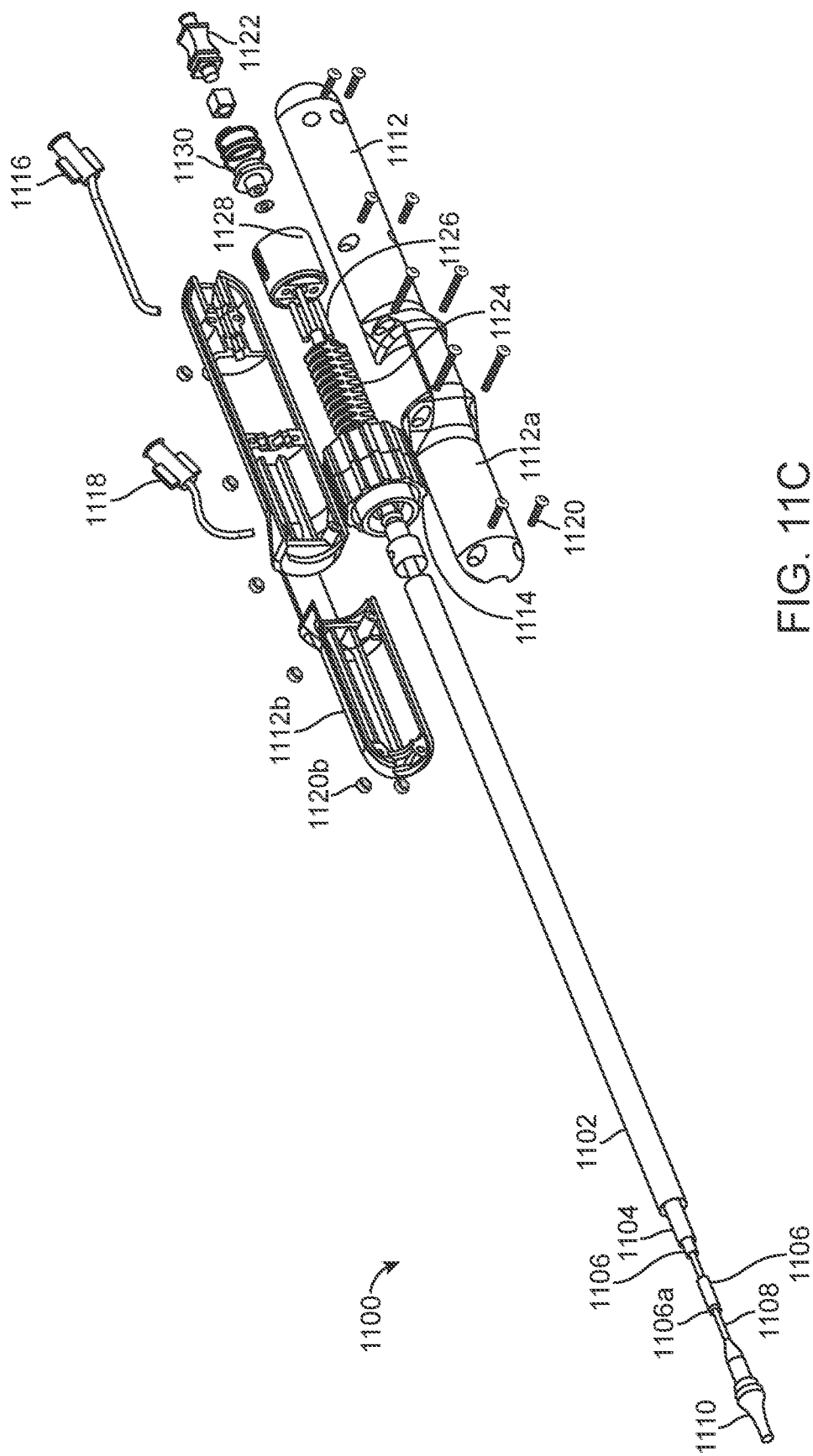

FIG. 11C is a partial exploded view of the delivery system 1100 and more clearly illustrates the components in the handle 1112 and how they interact. The handle 1112 includes a housing having two halves 1112a, 1112b which hold all the components. The handle is preferably held together with screws 1120 and nuts 1120b, although it may also be sealed using other techniques such as a press fit, snap fit, adhesive bonding, ultrasonic welding, etc. Rotation of actuator wheel 1114 is translated into linear motion of threaded insert 1124. The outer sheath catheter shaft 1102 is coupled to the threaded insert 1124, therefore rotation of actuator wheel 1114 in one direction will advance the sheath catheter shaft 1102, and rotation in the opposite direction will retract the sheath catheter shaft 1102. Further rotation of actuator wheel 1114 retracts threaded insert 1124 enough to bump into pins 1126 which are coupled to insert 1128, thereby also moving insert 1128. The bell catheter shaft 1106 is coupled to insert 1128, therefore further rotation of the actuator wheel 1114 will move the outer shaft 1102 and also move the bell catheter shaft 1106. Rotation of the actuator wheel in the opposite direction advances the sheath and threaded insert 1124 disengages from pins 1126. Spring 1130 returns insert 1128 to its unbiased position, thereby returning the bell catheter shaft to its unbiased position.

Any of the prosthetic cardiac valves disclosed herein may be carried by delivery system 1100. The atrial skirt, annular skirt, anterior tabs, posterior tab and ventricular skirt are loaded over the bell catheter shaft and disposed under the outer sheath catheter shaft 1102. The ventricular skirt is loaded proximally so that it is closest to the handle 1112 and the atrial skirt is loaded most distally so it is closest to the tip 1110. Therefore, retraction of outer sheath catheter shaft 1102 plays a significant part in controlling deployment of the prosthetic cardiac valve. The atrial skirt therefore expands first when the outer sheath catheter is retracted. The prosthetic valve commissures may be coupled with a hub 1106a on the distal portion of hub catheter 1106 and then the bell catheter shaft is disposed thereover, thereby releasably engaging the commissures with the delivery catheter. Once other portions of the prosthetic cardiac valve have expanded, the commissures may be released.

Figure 11D:
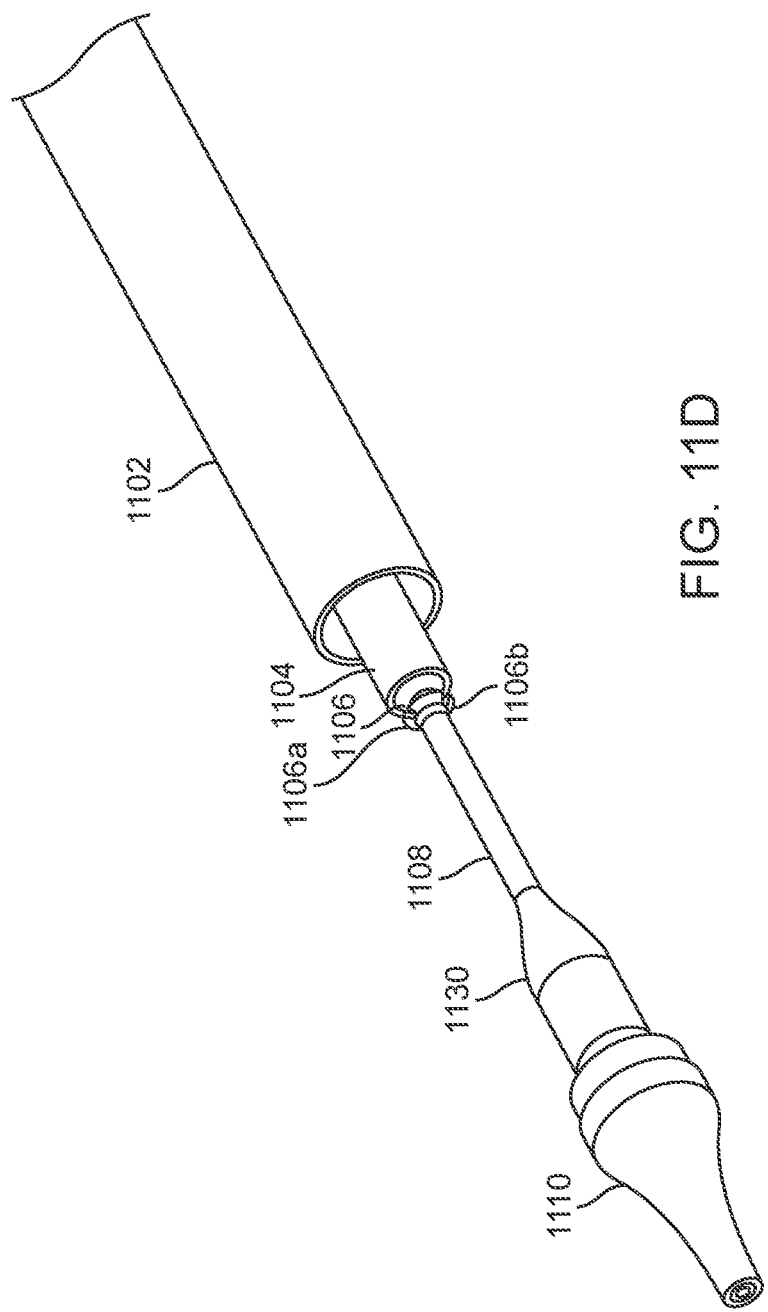

FIG. 11D highlights the distal portion of the delivery system 1100. Outer sheath catheter shaft 1102 advances and retracts relative to bell catheter shaft 1104 which is slidably disposed in the outer sheath catheter shaft 1102. Hub catheter shaft 1106 is shown slidably disposed in bell catheter shaft 1104 and with bell catheter shaft 1104 retracted so as to expose the hub 1106a having slots 1106b that hold the prosthetic valve commissures. Inner guidewire catheter shaft 1108 is the innermost shaft and has a tapered conical section 1130 which provides a smooth transition for the prosthetic valve and prevents unwanted bending or buckling of the prosthetic cardiac valve frame. Tissue penetrating tip 1110 is adapted to penetrate tissue, especially in a cardiac transapical procedure.

Delivery Method. A number of methods may be used to deliver a prosthetic cardiac valve to the heart. Exemplary methods of delivering a prosthetic mitral valve may include a transluminal delivery route which may also be a transseptal technique which crosses the septum between the right and left sides of the heart, or in more preferred embodiments, a transapical route may be used such as illustrated in FIGS. 12A-12L. The delivery device previously described above may be used to deliver any of the embodiments of prosthetic valves described herein, or other delivery devices and other prosthetic valves may also be used, such as those disclosed in U.S. patent application Ser. No. 13/096,572, previously incorporated herein by reference. However, in this preferred exemplary embodiment, the prosthetic cardiac valve of FIG. 6 is used so that the anterior tabs deploy first, followed by the posterior tab, and then the ventricular skirt. In the embodiment where the prosthetic valve has a foot instead of a posterior tab, deployment is generally the same, but the foot is expanded instead of the posterior tab.

Figure 12A:
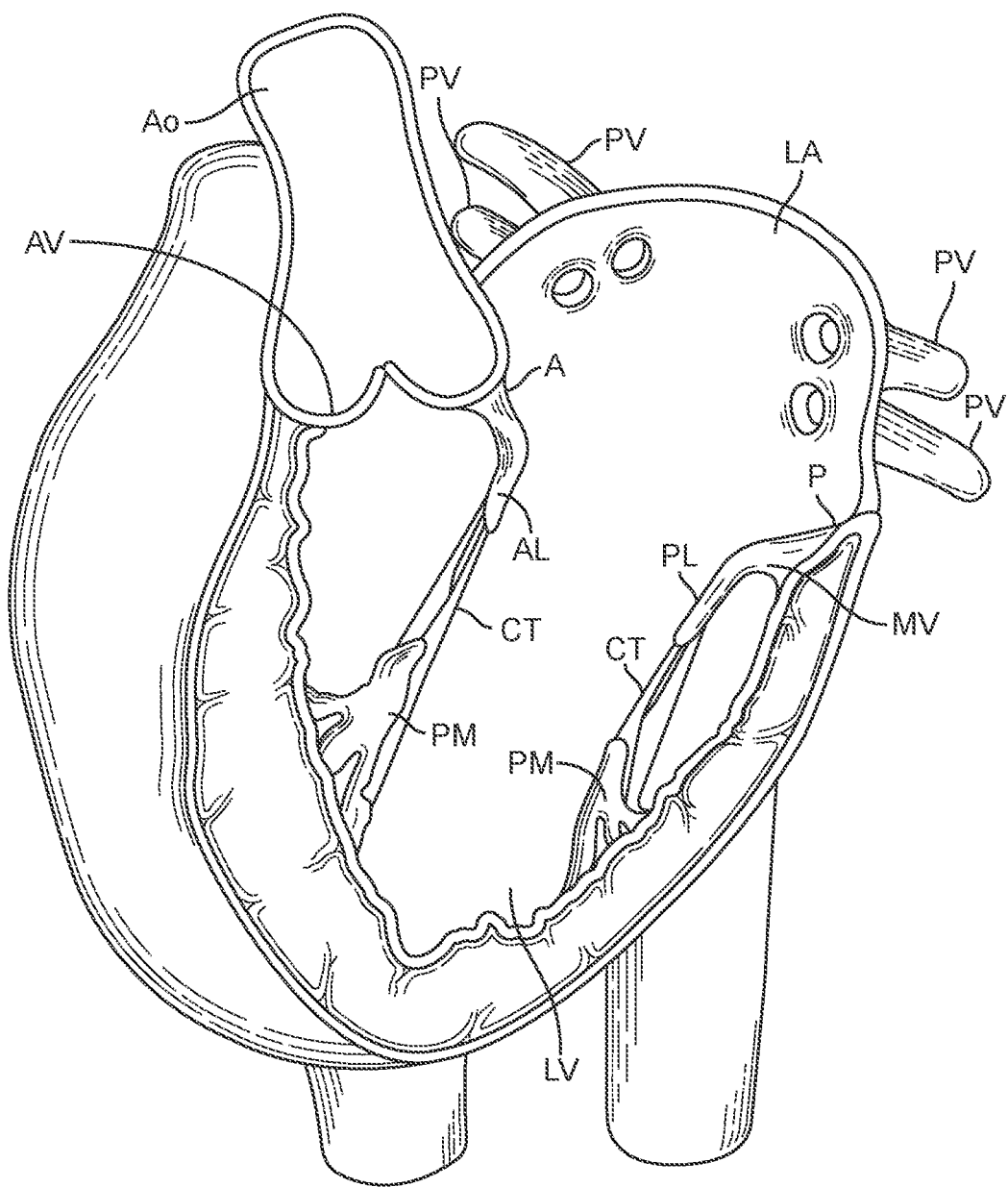
FIGS. 12A-12L illustrate an exemplary method of implanting a prosthetic cardiac valve.

FIG. 12A illustrates the basic anatomy of the left side of a patient's heart including the left atrium LA and left ventricle LV. Pulmonary veins PV return blood from the lungs to the left atrium and the blood is then pumped from the left atrium into the left ventricle across the mitral valve MV. The mitral valve includes an anterior leaflet AL on an anterior side A of the valve and a posterior leaflet PL on a posterior side P of the valve. The leaflets are attached to chordae tendineae CT which are subsequently secured to the heart walls with papillary muscles PM. The blood is then pumped out of the left ventricle into the aorta Ao with the aortic valve AV preventing regurgitation.

Figure 12B:
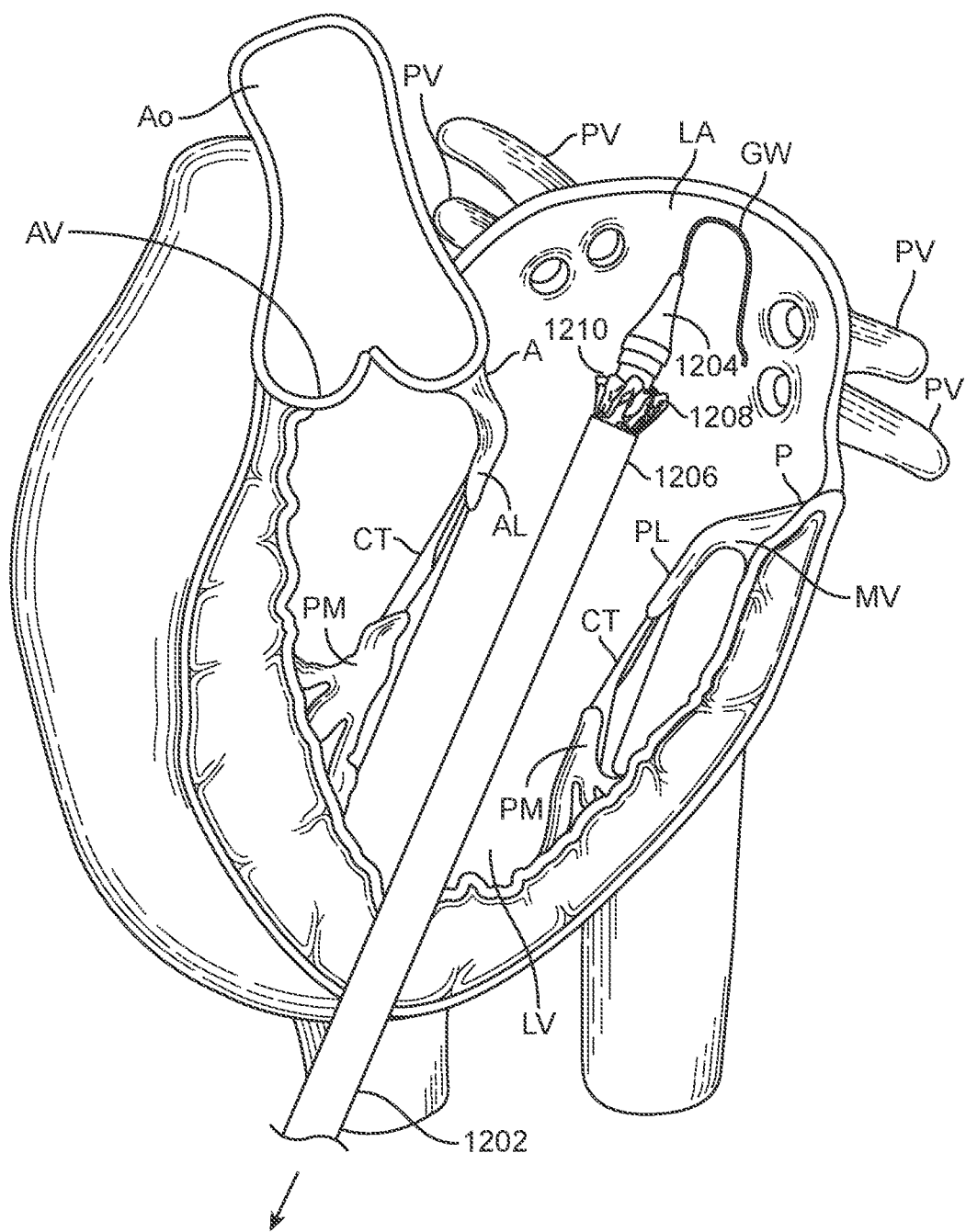
Figure 12C:
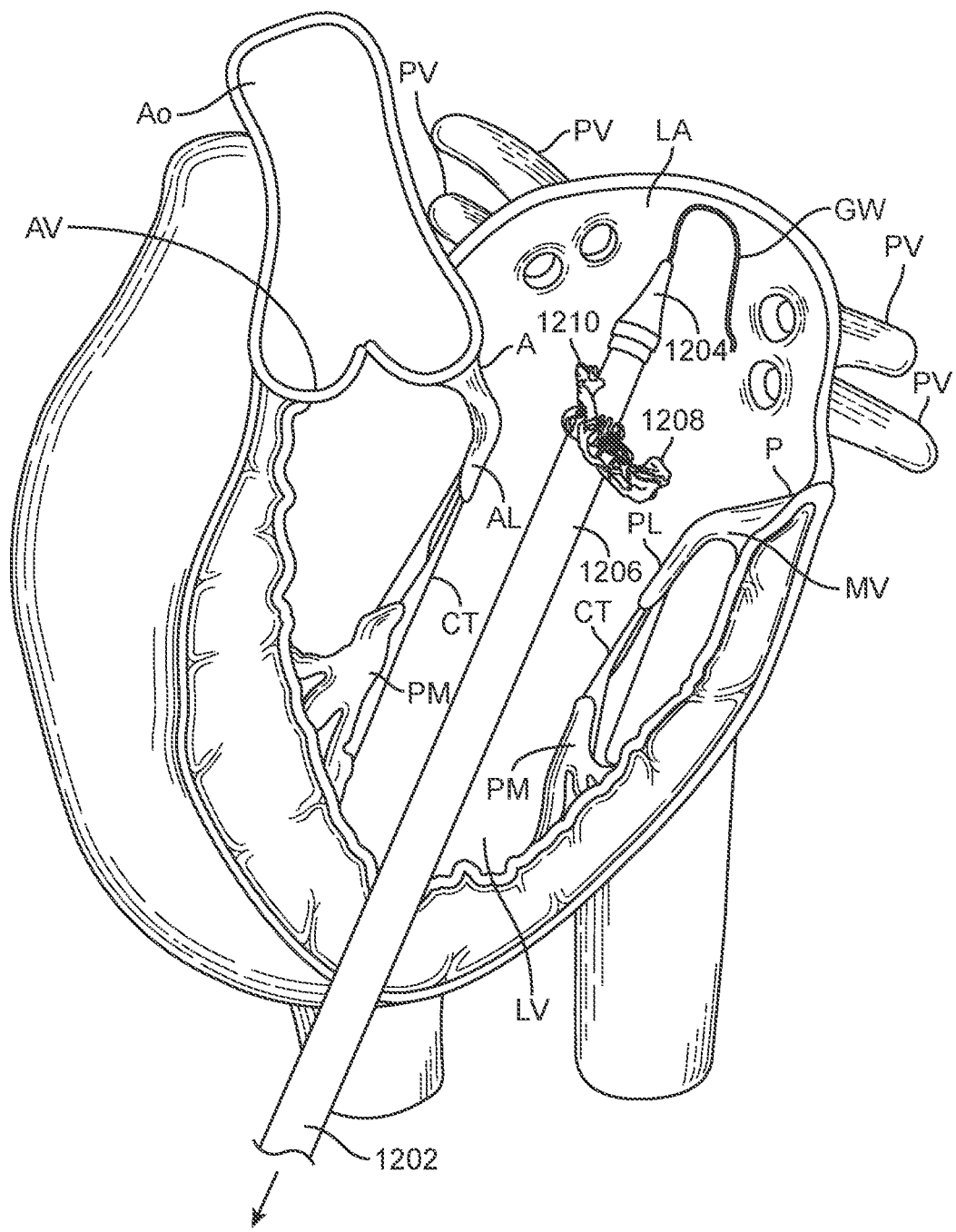
Figure 12D:
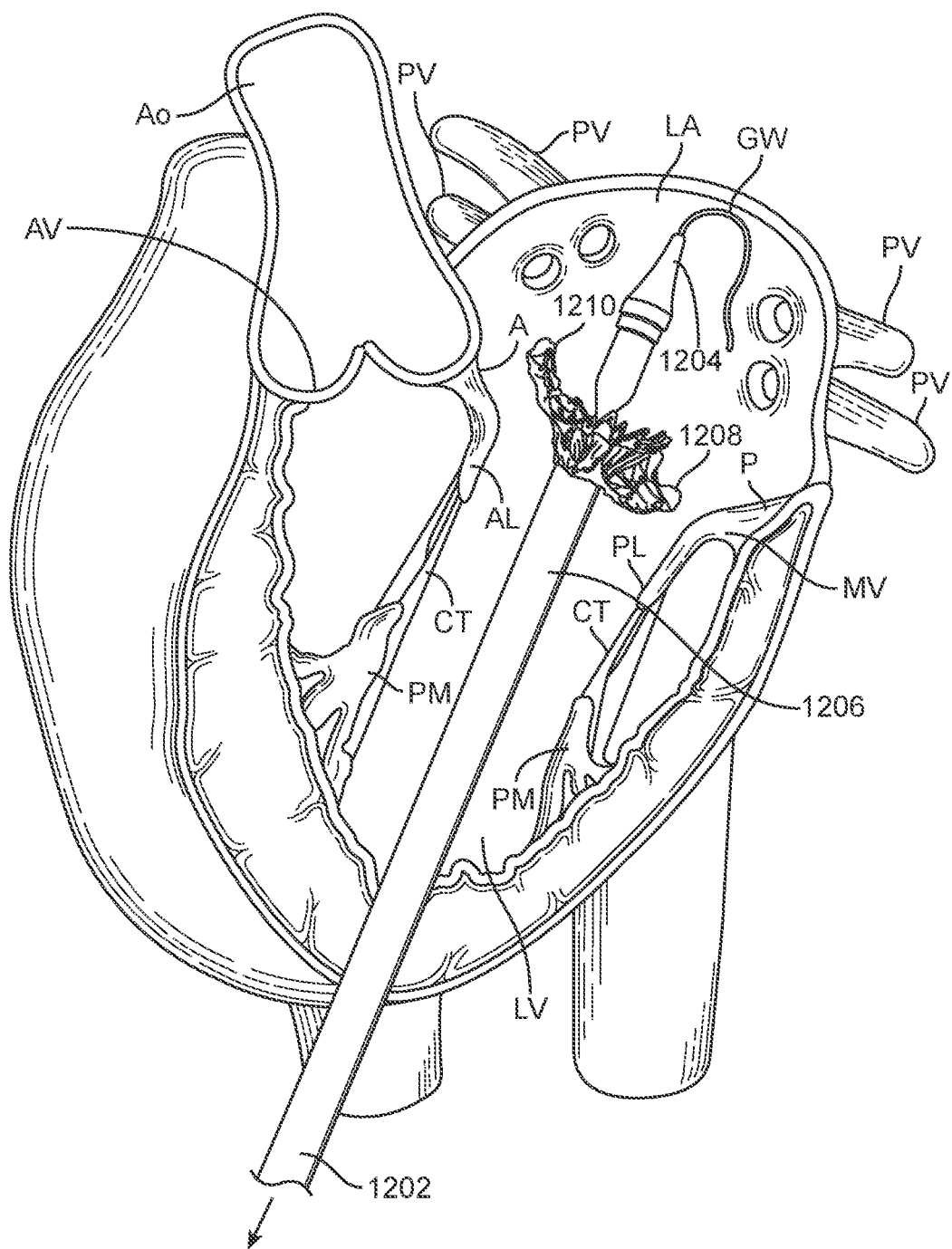

FIG. 12B illustrates transapical delivery of a delivery system 1202 through the apex of the heart into the left atrium LA via the left ventricle LV. The delivery system 1202 may be advanced over a guidewire GW into the left atrium, and a tissue penetrating tip 1204 helps the delivery system pass through the apex of the heart by dilating the tissue and forming a larger channel for the remainder of the delivery system to pass through. The delivery catheter carries prosthetic cardiac valve 1208. Once the distal portion of the delivery system has been advanced into the left atrium, the outer sheath 1206 may be retracted proximally (e.g. toward the operator) thereby removing the constraint from the atrial portion of the prosthetic valve 1208. This allows the atrial skirt 1210 to self-expand radially outward. In FIG. 12C, as the outer sheath is further retracted, the atrial skirt continues to self-expand and peek out, until it fully deploys as seen in FIG. 12D. The atrial skirt may have a cylindrical shape or it may be D-shaped as discussed above with a flat anterior portion and a cylindrical posterior portion so as to avoid interfering with the aortic valve and other aspects of the left ventricular outflow tract. The prosthesis may be oriented and properly positioned by rotating the prosthesis and visualizing the alignment element previously described. Also, the prosthetic cardiac valve may be advanced upstream or downstream to properly position the atrial skirt. In preferred embodiments, the atrial skirt forms a flange that rests against a superior surface of the mitral valve and this anchors the prosthetic valve and prevents it from unwanted movement downstream into the left ventricle.

Figure 12E:
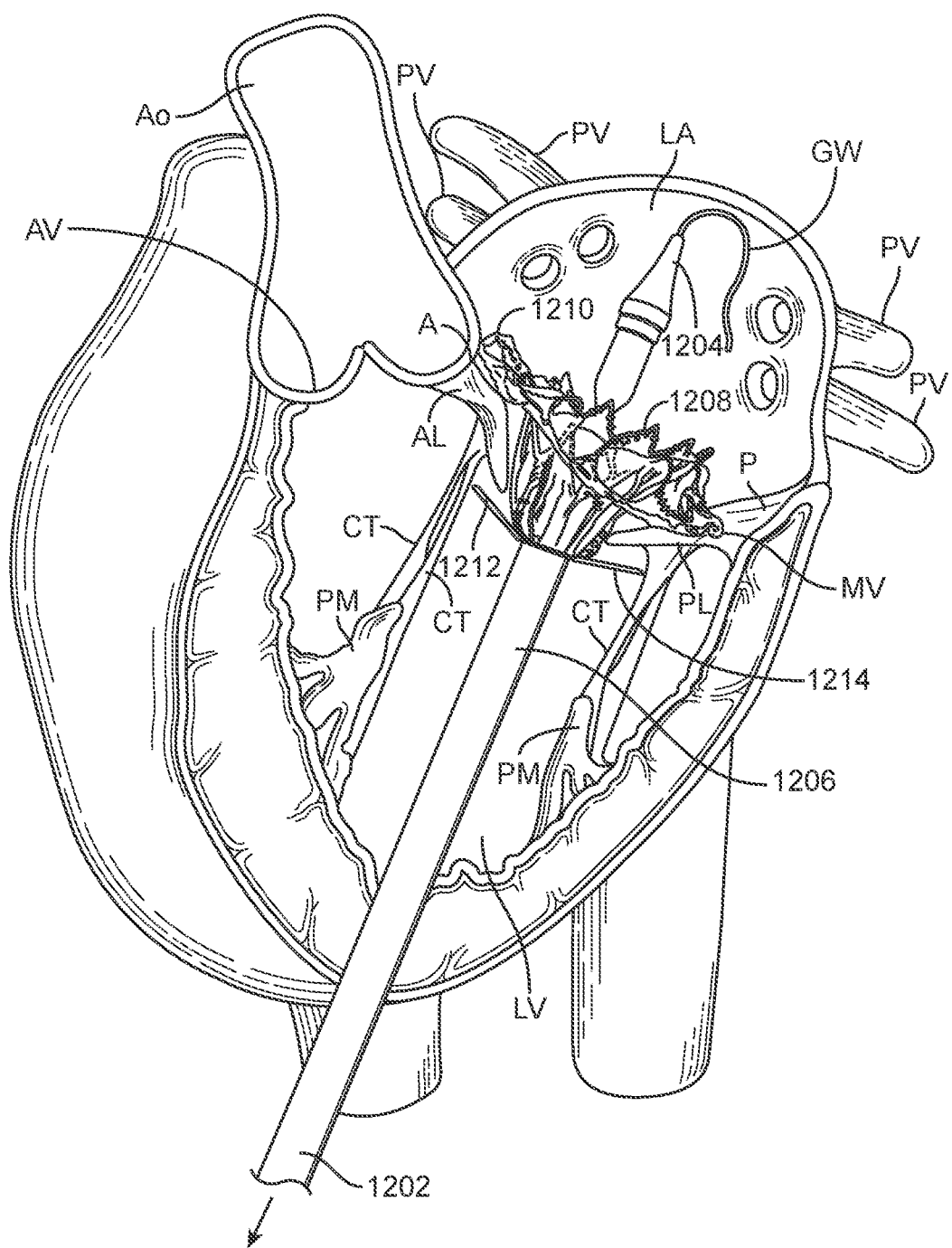
Figure 12F:
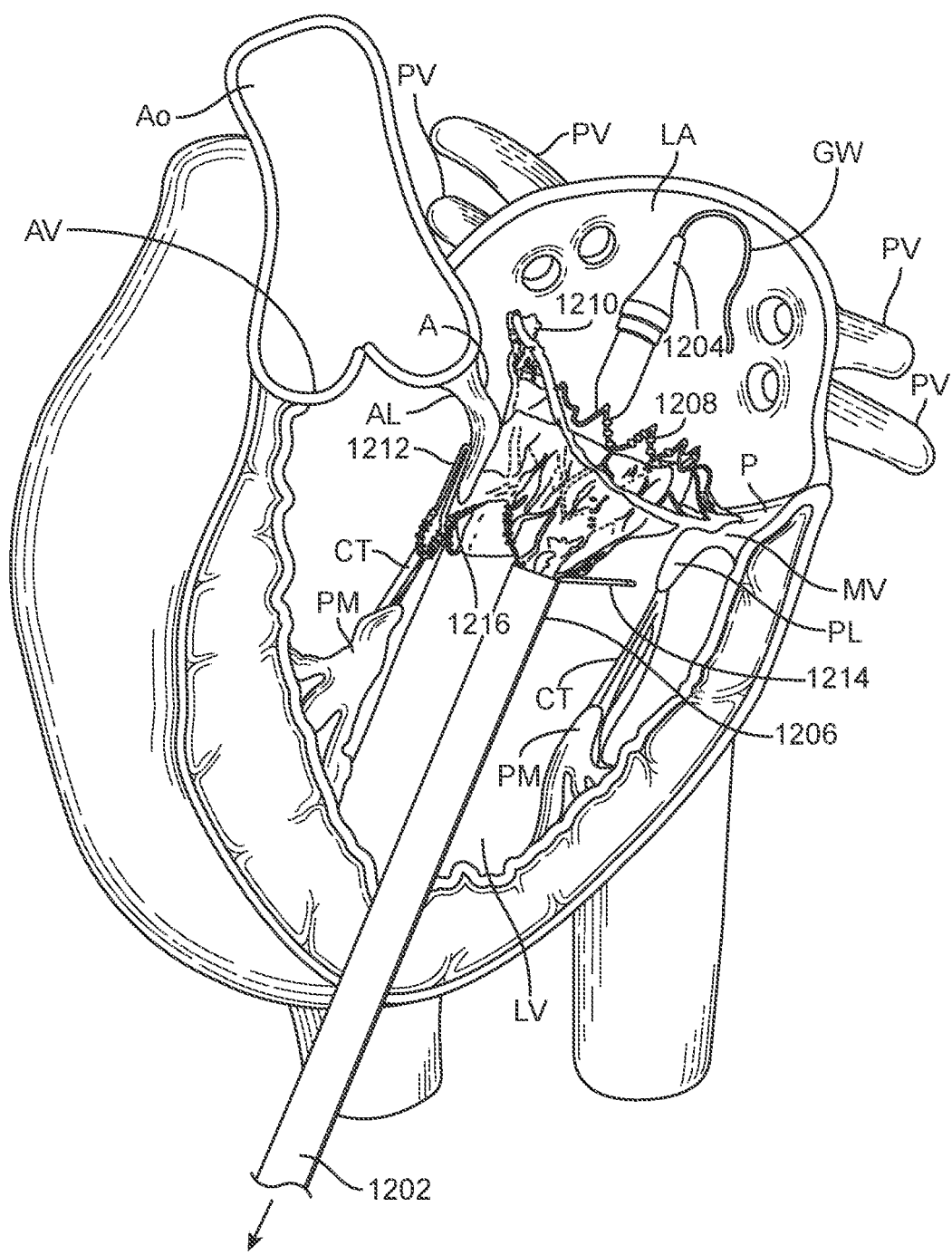

As the outer sheath 1206 continues to be proximally retracted, the annular region of the prosthetic cardiac valve self-expands next into engagement with the valve annulus. The annular region also preferably has the D-shaped geometry, although it may also be cylindrical or have other geometries to match the native anatomy. In FIG. 12E, retraction of sheath 1206 eventually allows both the anterior 1212 and posterior 1214 tabs to partially self-expand outward preferably without engaging the anterior or posterior leaflets or the chordae tendineae. In this embodiment, further retraction of the outer sheath 1206 then allows both the anterior tabs 1212 (only one visible in this view) to complete their self-expansion so that the anterior leaflet is captured between an inner surface of each of the anterior tabs and an outer surface of the ventricular skirt 1216, as illustrated in FIG. 12F. The posterior tab 1214 remains partially open, but has not completed its expansion yet. Additionally, the tips of the anterior tabs also anchor into the left and right fibrous trigones of the mitral valve, as will be illustrated in greater detail below.

Figure 12G:
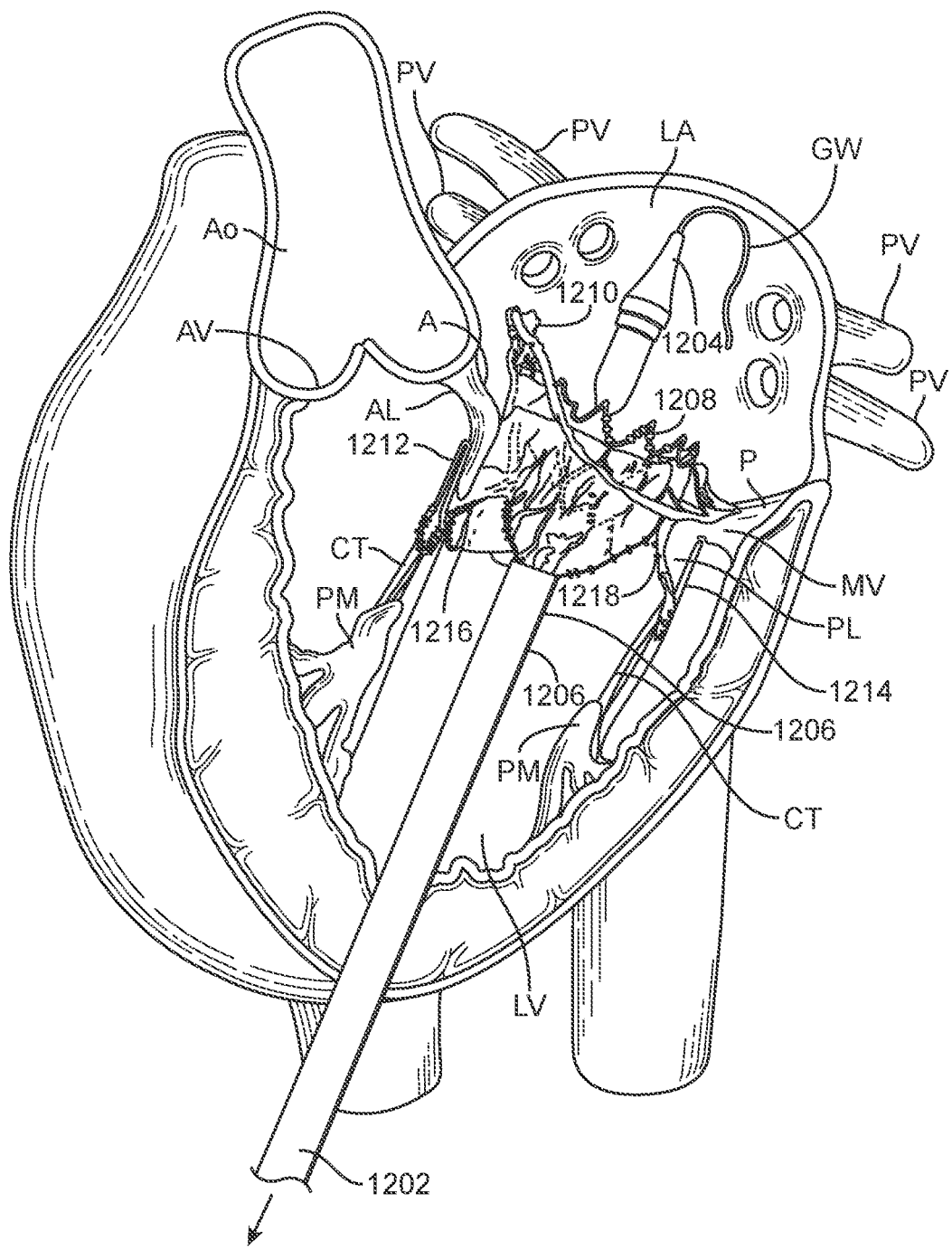
Figure 12H:
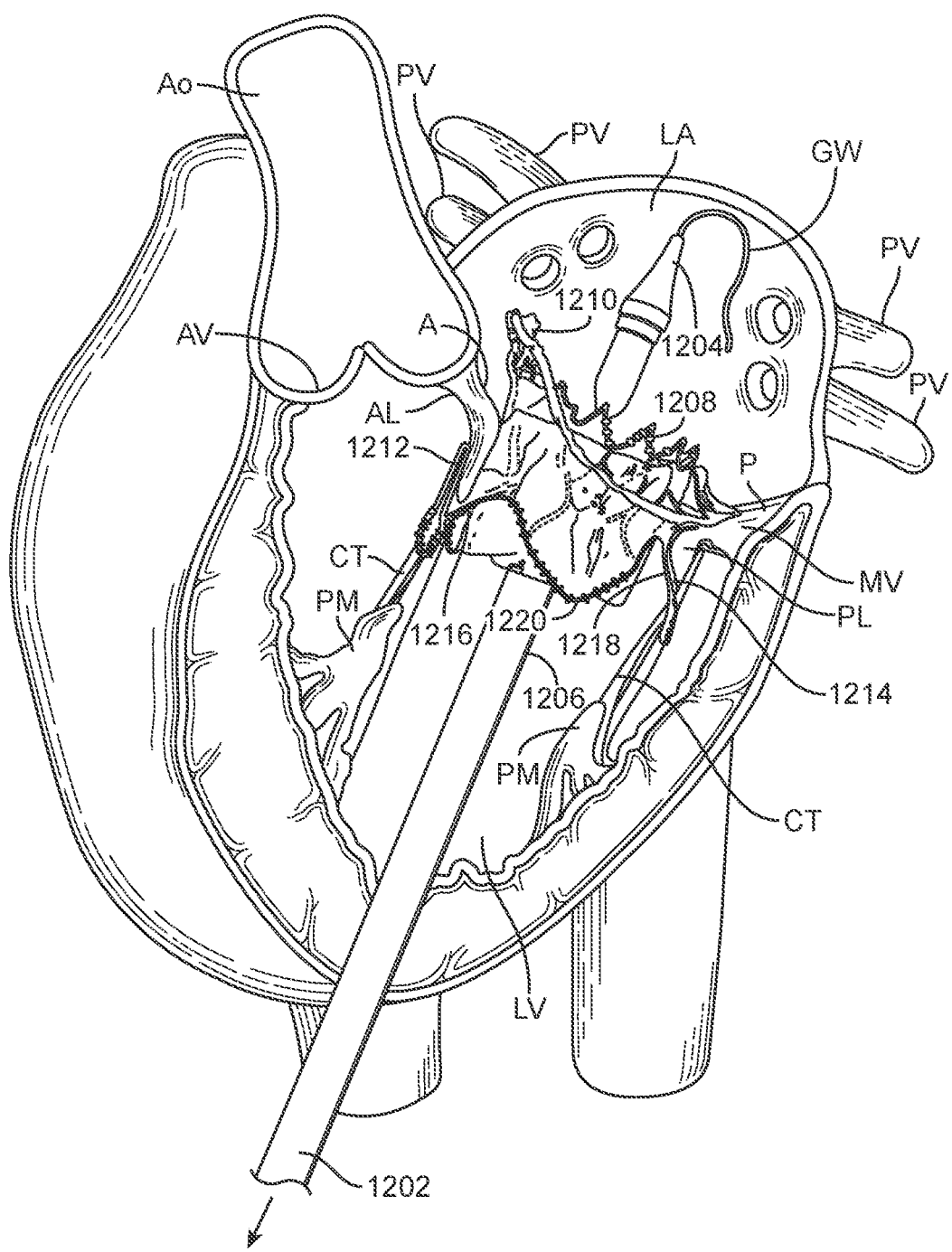

In FIG. 12G, further retraction of the outer sheath 1206 then releases the constraints from the posterior tab 1214 allowing it to complete its self-expansion, thereby capturing the posterior leaflet PL between an inner surface of the posterior tab 1214 and an outer surface of the ventricular skirt 1218. In FIG. 12H, the sheath is retracted further releasing the ventricular skirt 1220 and allowing the ventricular skirt 1220 to radially expand outward, further capturing the anterior and posterior leaflets between the outer surface of the ventricular skirt and their respective anterior or posterior tabs. Expansion of the ventricular skirt also pushes the anterior and posterior leaflets outward, thereby ensuring that the native leaflets do not interfere with any portion of the prosthetic valve or the prosthetic valve leaflets. The prosthetic valve is now anchored in position above the mitral valve, along the annulus, to the valve leaflets, and below the mitral valve, thereby securing it in position.

Figure 12I:
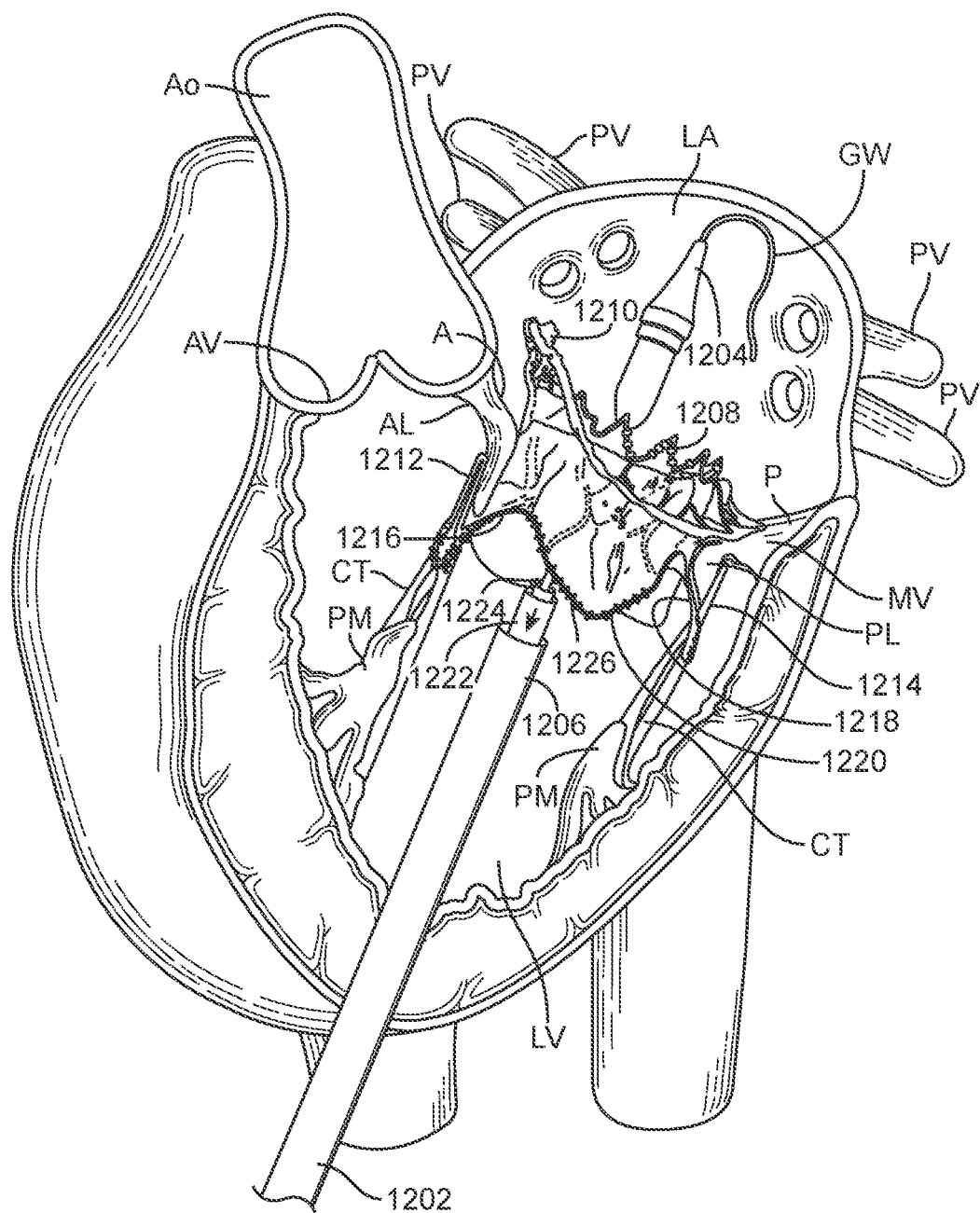
Figure 12J:
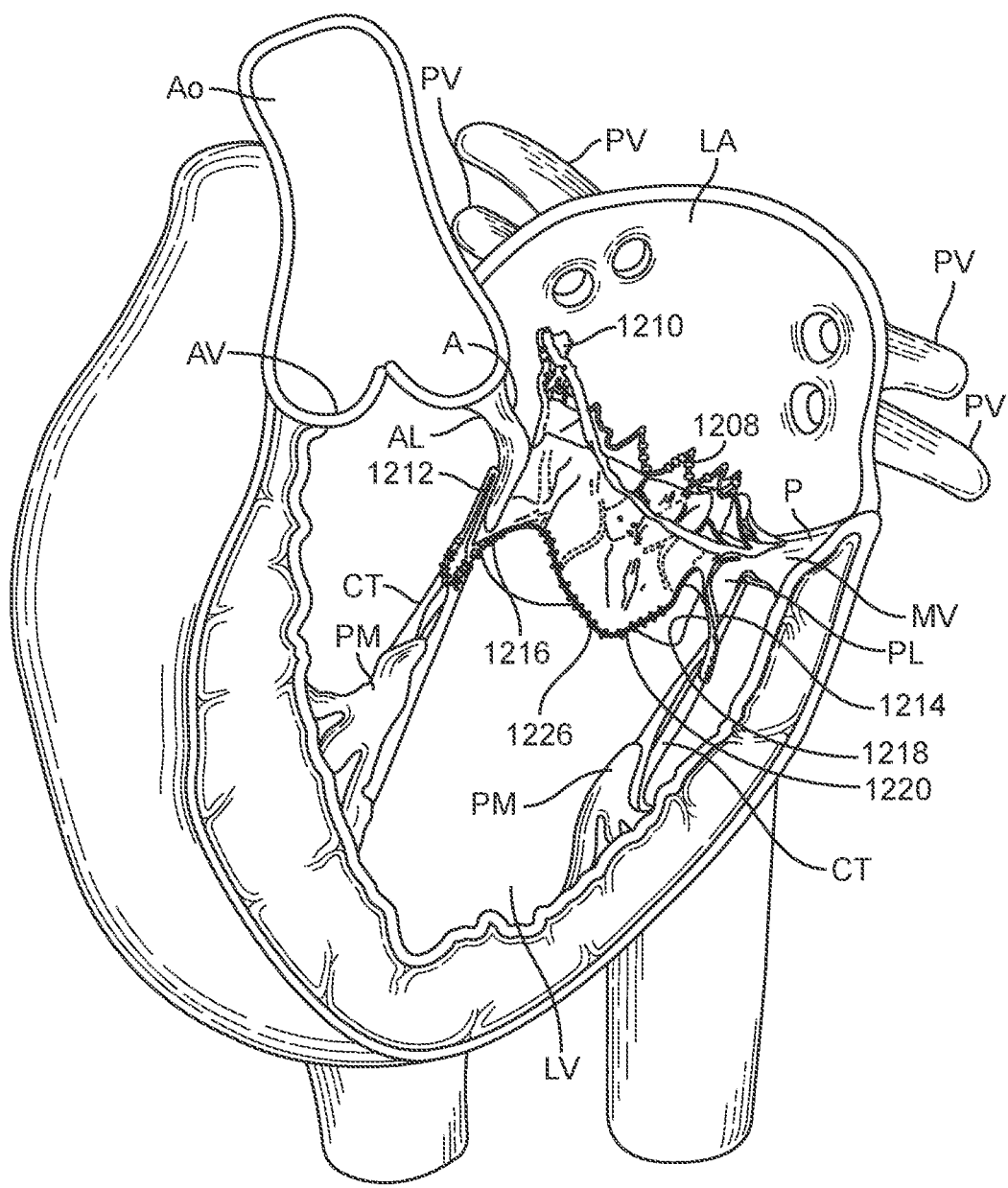

Further actuation of the delivery device now retracts the outer sheath 1206 and the bell catheter shaft 1222 so as to remove the constraint from the hub catheter 1224, as illustrated in FIG. 12I. This permits the prosthetic valve commissures 1226 to be released from the hub catheter, thus the commissures expand to their biased configuration. The delivery system 1202 and guidewire GW are then removed, leaving the prosthetic valve 1208 in position where it takes over for the native mitral valve, as seen in FIG. 12J.

Figure 12K:
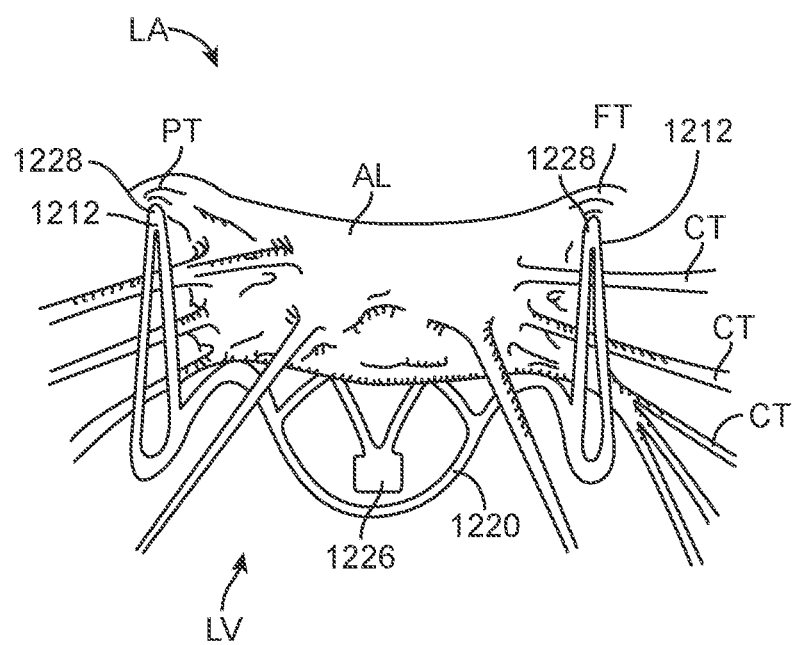
Figure 12L:
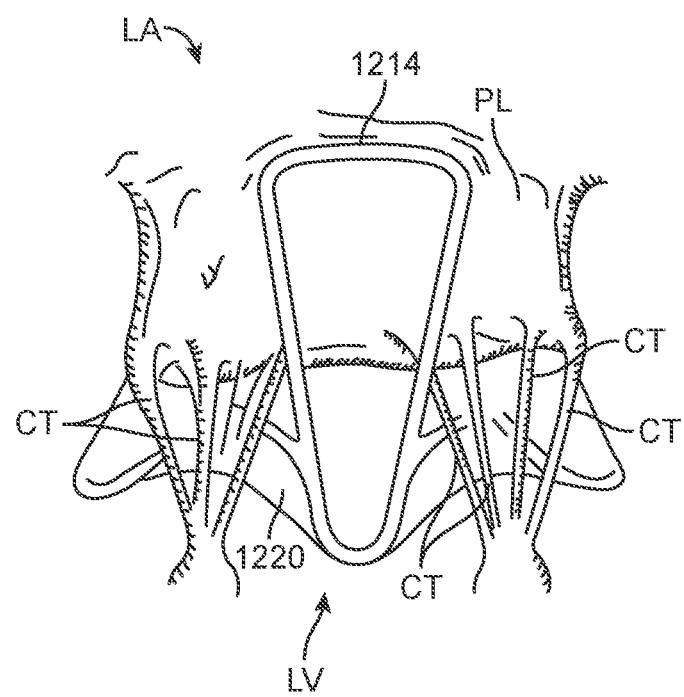

FIGS. 12K and 12L highlight engagement of the anterior and posterior tabs with the respective anterior and posterior leaflets. In FIG. 12K, after anterior tabs 1212 have been fully expanded, they capture the anterior leaflet AL and may capture adjacent chordae tendineae between an inside surface of the anterior tab and an outer surface of the ventricular skirt 1220. Moreover, the tips 1228 of the anterior tabs 1212 are engaged with the fibrous trigones FT of the anterior side of the mitral valve. The fibrous trigones are fibrous regions of the valve thus the anterior tabs further anchor the prosthetic valve into the native mitral valve anatomy. One anterior tab anchors into the left fibrous trigone, and the other anterior tabs anchors into the right fibrous trigone. The trigones are on opposite sides of the anterior side of the leaflet. FIG. 12L illustrates engagement of the posterior tab 1214 with the posterior leaflet PL which is captured between an inner surface of the posterior tab and an outer surface of the ventricular skirt 1220. Additionally, adjacent chordae tendineae may be captured between the posterior tab and ventricular skirt.

FIGS. 13A-13L illustrate another exemplary embodiment of a delivery method. This embodiment is similar to that previously described, with the major difference being the order in which the prosthetic cardiac valve self-expands into engagement with the mitral valve. Any delivery device or any prosthetic valve disclosed herein may be used, however in preferred embodiments, the embodiment of FIG. 7 is used. Varying the order may allow better positioning of the implant, easier capturing of the valve leaflets, and better anchoring of the implant. This exemplary method also preferably uses a transapical route, although transseptal may also be used.

Figure 13A:
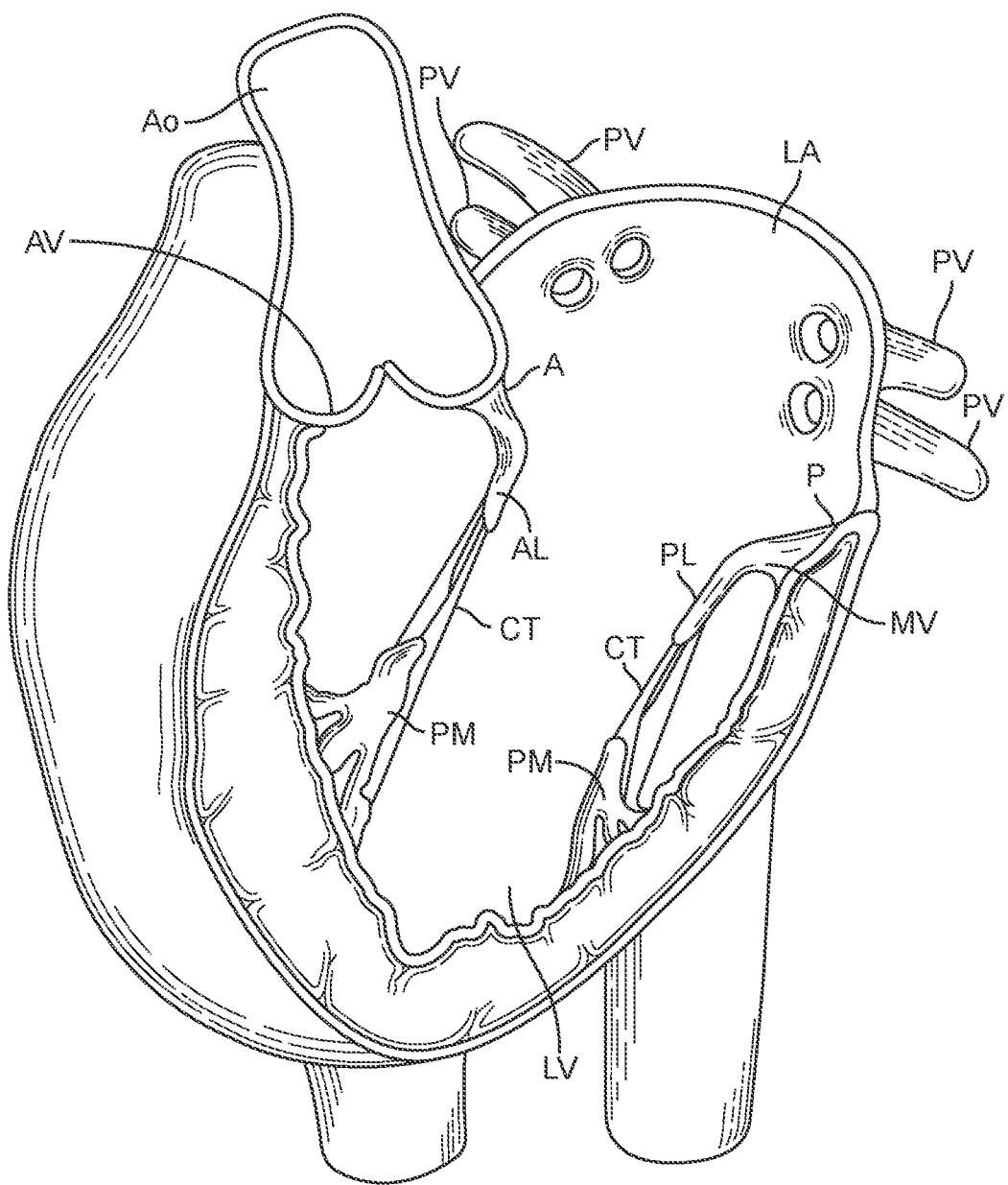
FIGS. 13A-13L illustrate another exemplary method of implanting a prosthetic cardiac valve.

FIG. 13A illustrates the basic anatomy of the left side of a patient's heart including the left atrium LA and left ventricle LV. Pulmonary veins PV return blood from the lungs to the left atrium and the blood is then pumped from the left atrium into the left ventricle across the mitral valve MV. The mitral valve includes an anterior leaflet AL on an anterior side A of the valve and a posterior leaflet PL on a posterior side P of the valve. The leaflets are attached to chordae tendineae CT which are subsequently secured to the heart walls with papillary muscles PM. The blood is then pumped out of the left ventricle into the aorta AO with the aortic valve AV preventing regurgitation.

Figure 13B:
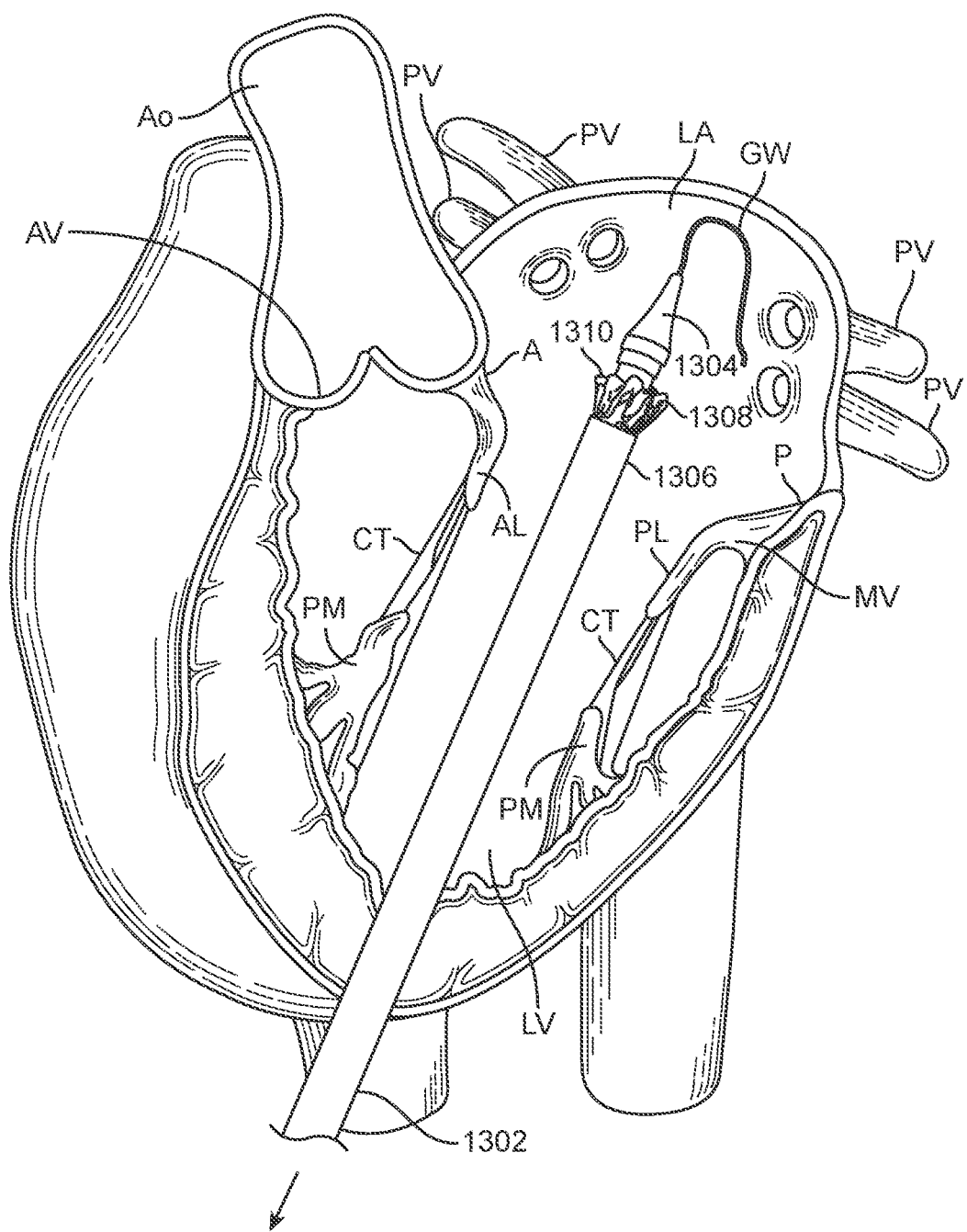
Figure 13C:
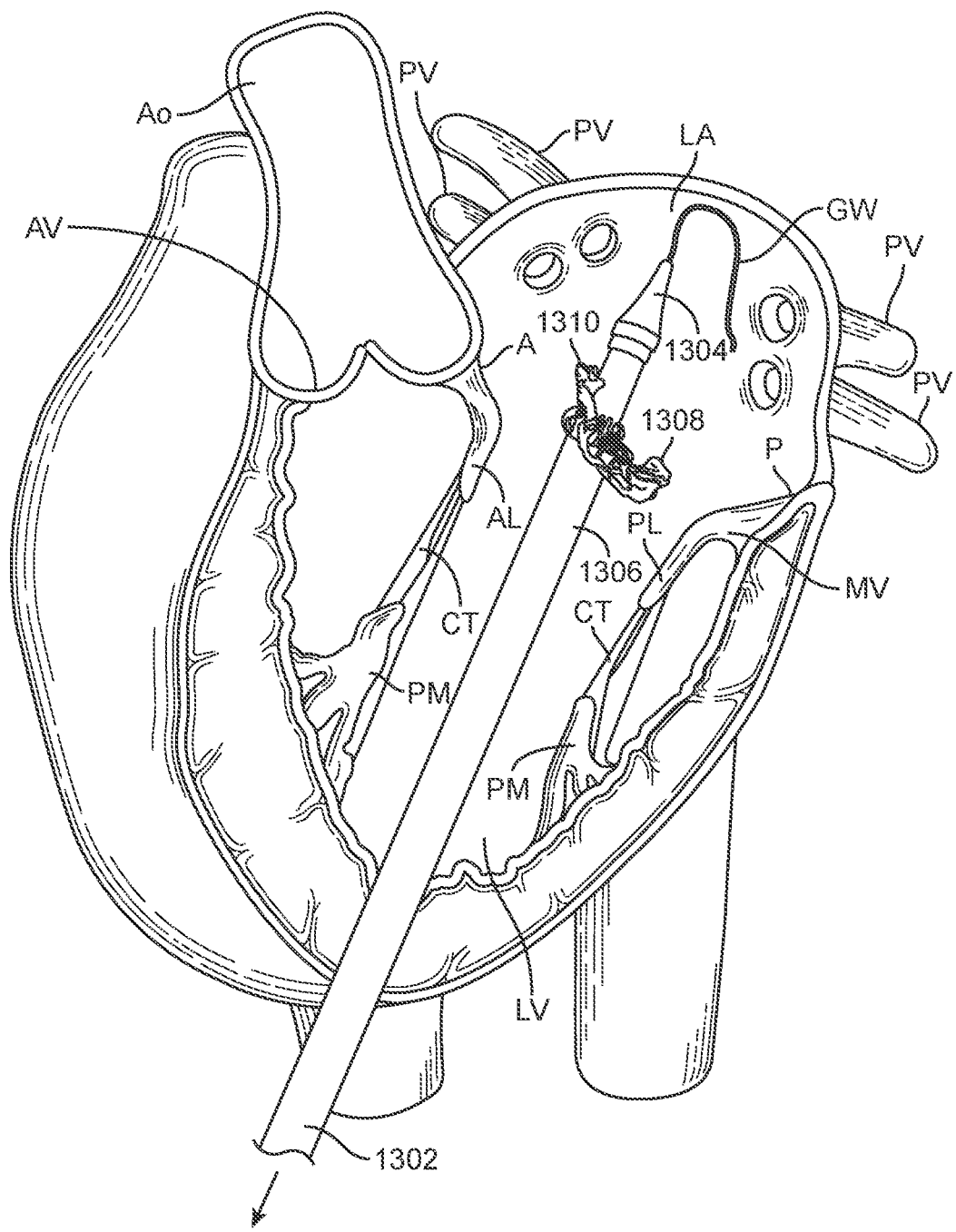
Figure 13D:
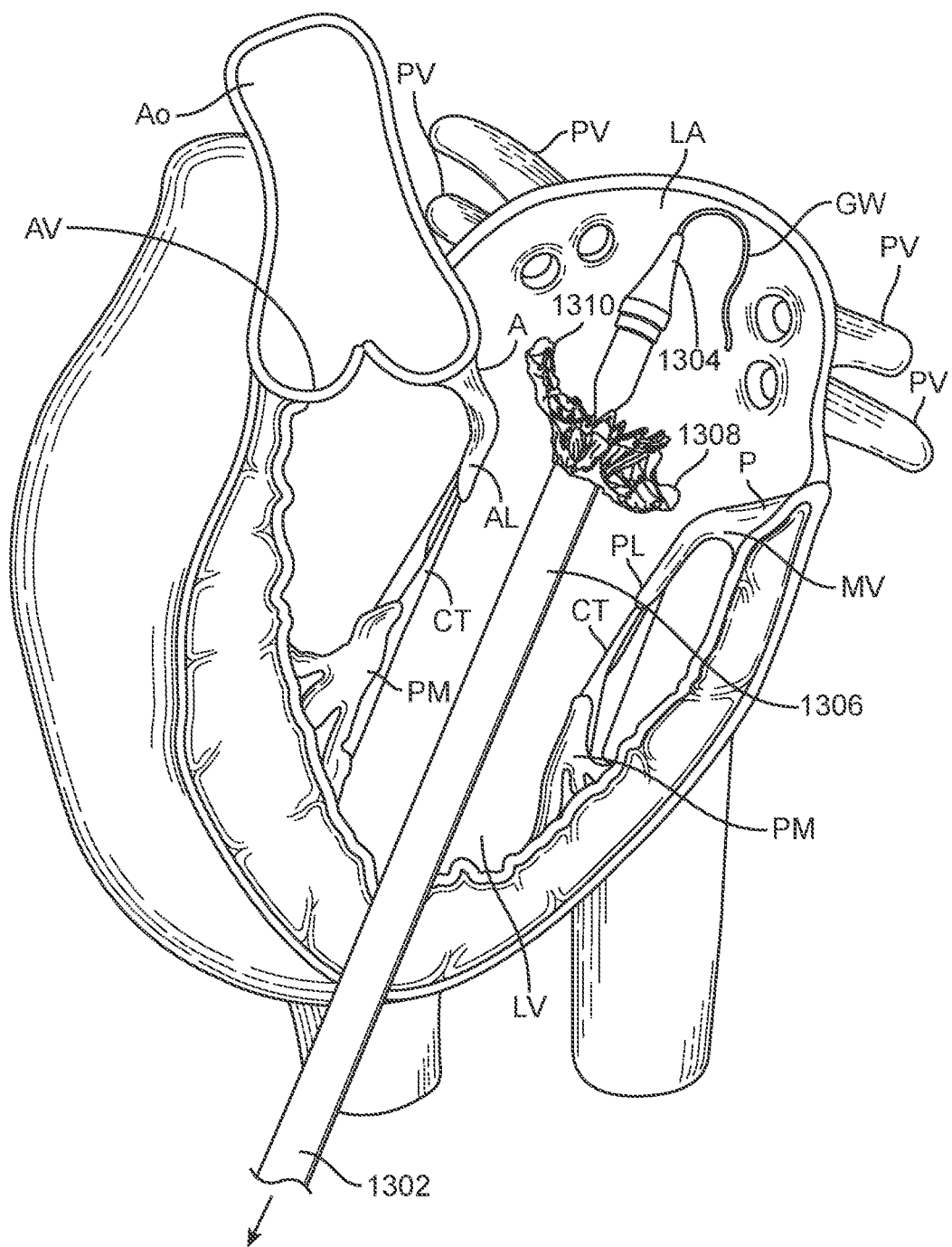

FIG. 13B illustrates transapical delivery of a delivery system 1302 through the apex of the heart into the left atrium LA via the left ventricle LV. The delivery system 1302 may be advanced over a guidewire GW into the left atrium, and a tissue penetrating tip 1304 helps the delivery system pass through the apex of the heart by dilating the tissue and forming a larger channel for the remainder of the delivery system to pass through. The delivery catheter carries prosthetic cardiac valve 1308. Once the distal portion of the delivery system has been advanced into the left atrium, the outer sheath 1306 may be retracted proximally (e.g. toward the operator) thereby removing the constraint from the atrial portion of the prosthetic valve 1308. This allows the atrial skirt 1310 to self-expand radially outward. In FIG. 13C, as the outer sheath is further retracted, the atrial skirt continues to self-expand and peek out, until it fully deploys as seen in FIG. 13D. The atrial skirt may have a cylindrical shape or it may be D-shaped as discussed above with a flat anterior portion and a cylindrical posterior portion so as to avoid interfering with the aortic valve and other aspects of the left ventricular outflow tract. The prosthesis may be oriented and properly positioned by rotating the prosthesis and visualizing the alignment element previously described. Also, the prosthetic cardiac valve may be advanced upstream or downstream to properly position the atrial skirt. In preferred embodiments, the atrial skirt forms a flange that rests against a superior surface of the mitral valve and this anchors the prosthetic valve and prevents it from unwanted movement downstream into the left ventricle.

Figure 13E:
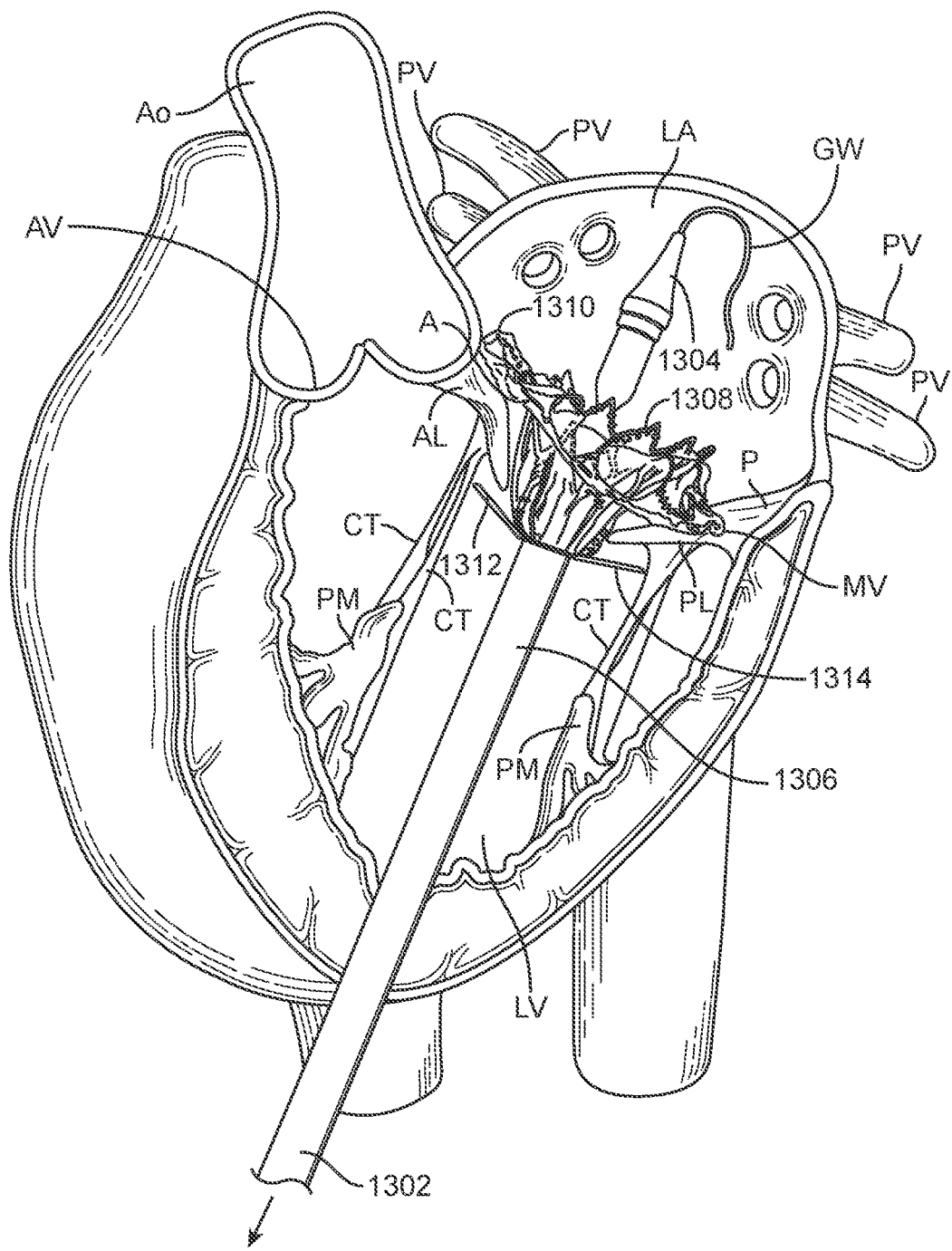
Figure 13F:
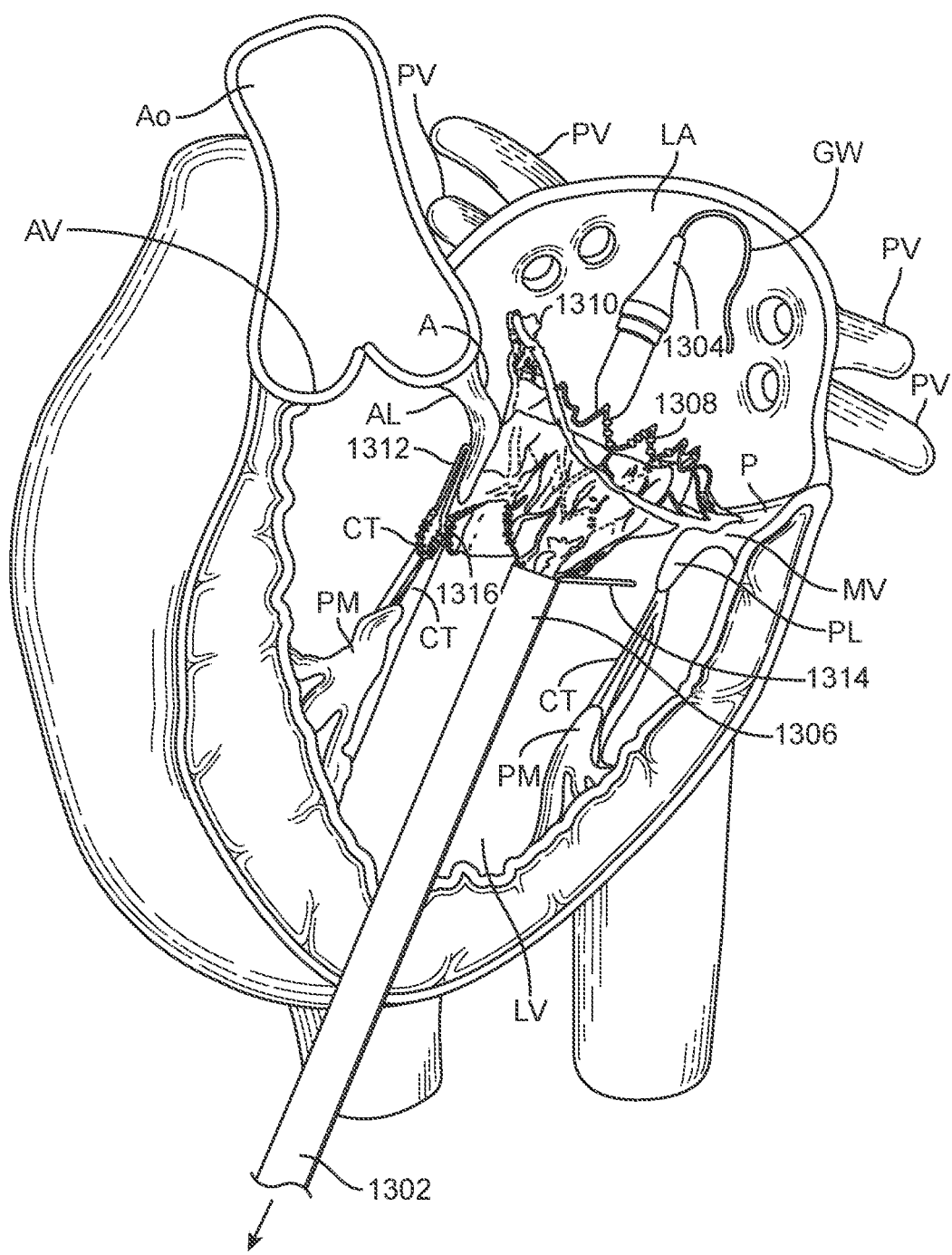

As the outer sheath 1306 continues to be proximally retracted, the annular region of the prosthetic cardiac valve self-expands next into engagement with the valve annulus. The annular region also preferably has the D-shaped geometry, although it may also be cylindrical or have other geometries to match the native anatomy. In FIG. 13E, retraction of sheath 1306 eventually allows both the anterior 1312 and posterior 1314 tabs to partially self-expand outward preferably without engaging the anterior or posterior leaflets or the chordae tendineae. In this embodiment, further retraction of the outer sheath 1306 then allows both the anterior tabs 1312 (only one visible in this view) to complete their self-expansion so that the anterior leaflet is captured between an inner surface of each of the anterior tabs and an outer surface of the ventricular skirt 1316, as illustrated in FIG. 13F. The posterior tab 1214 remains partially open, but has not completed its expansion yet. Additionally, the tips of the anterior tabs also anchor into the left and right fibrous trigones of the mitral valve, as will be illustrated in greater detail below.

Figure 13G:
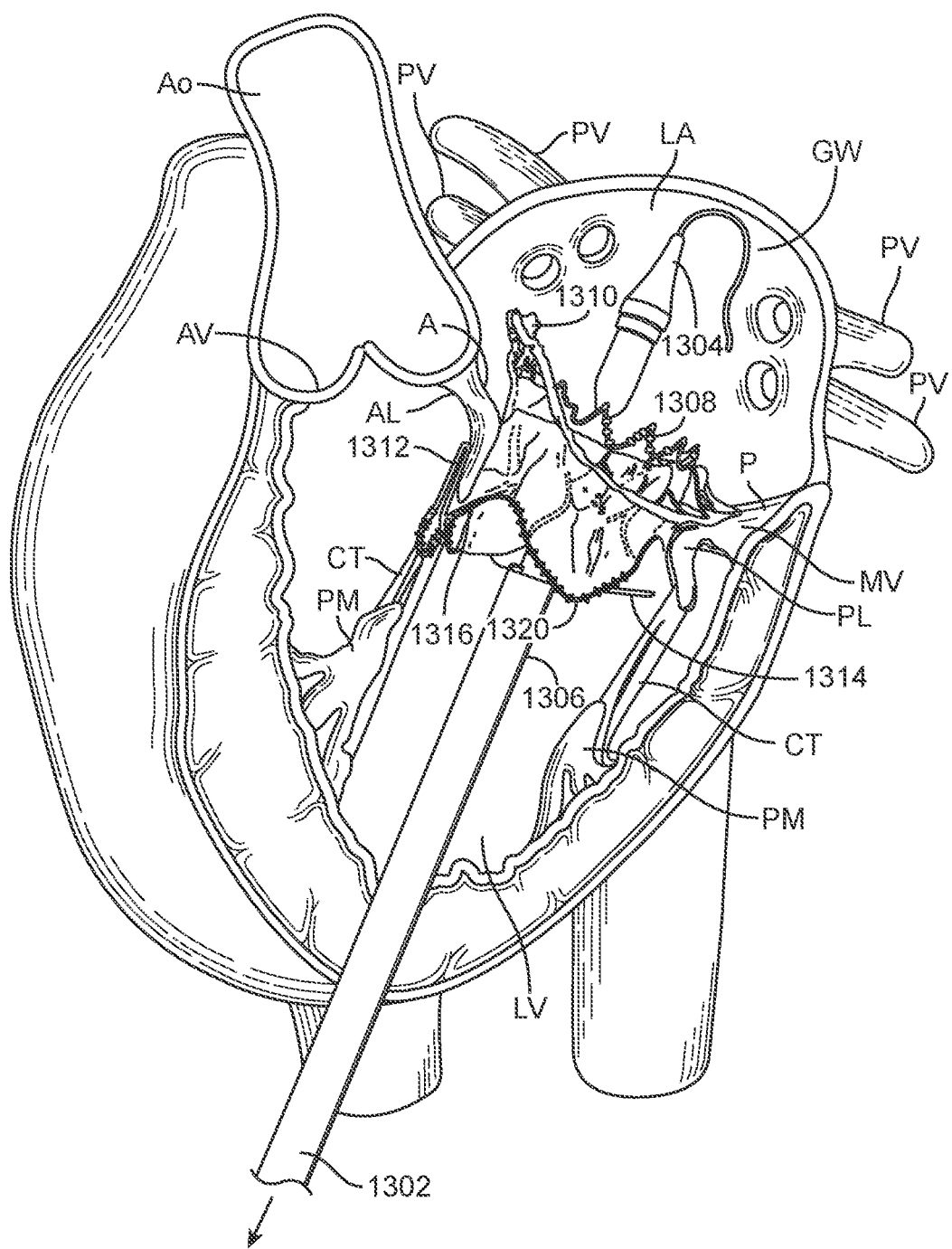
Figure 13H:
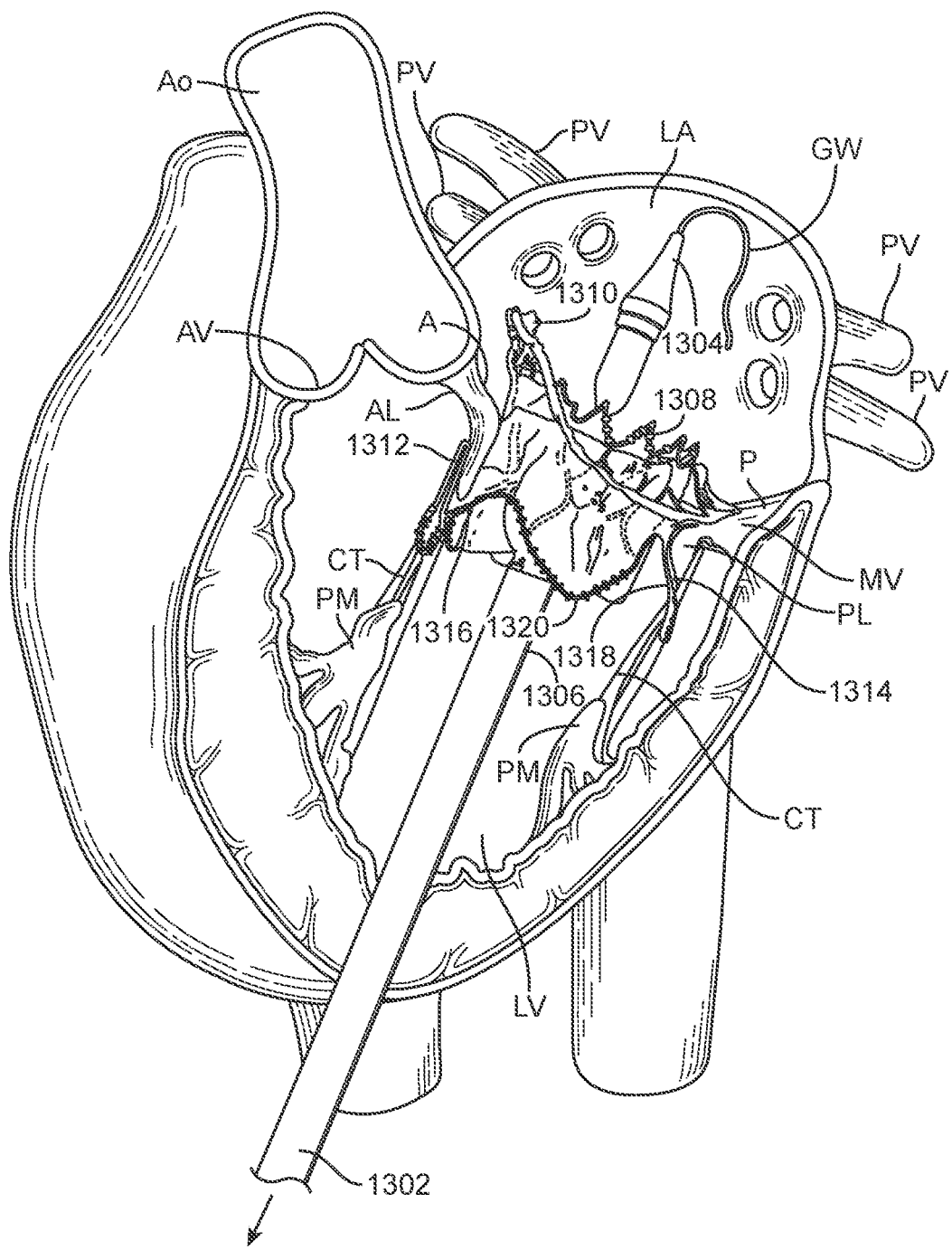

In FIG. 13G, further retraction of the outer sheath 1306 then releases the constraint from the ventricular skirt 1320 allowing the ventricular skirt to radially expand. This then further captures the anterior leaflets AL between the anterior tab 1312 and the ventricular skirt 1316. Expansion of the ventricular skirt also pushes the anterior and posterior leaflets outward, thereby ensuring that the native leaflets do not interfere with any portion of the prosthetic valve or the prosthetic valve leaflets. Further retraction of sheath 1306 as illustrated in FIG. 13H releases the constraint from the posterior tab 1314 allowing it to complete its self-expansion, thereby capturing the posterior leaflet PL between an inner surface of the posterior tab 1314 and an outer surface of the ventricular skirt 1318. The prosthetic valve is now anchored in position above the mitral valve, along the annulus, to the valve leaflets, and below the mitral valve, thereby securing it in position.

Figure 13I:
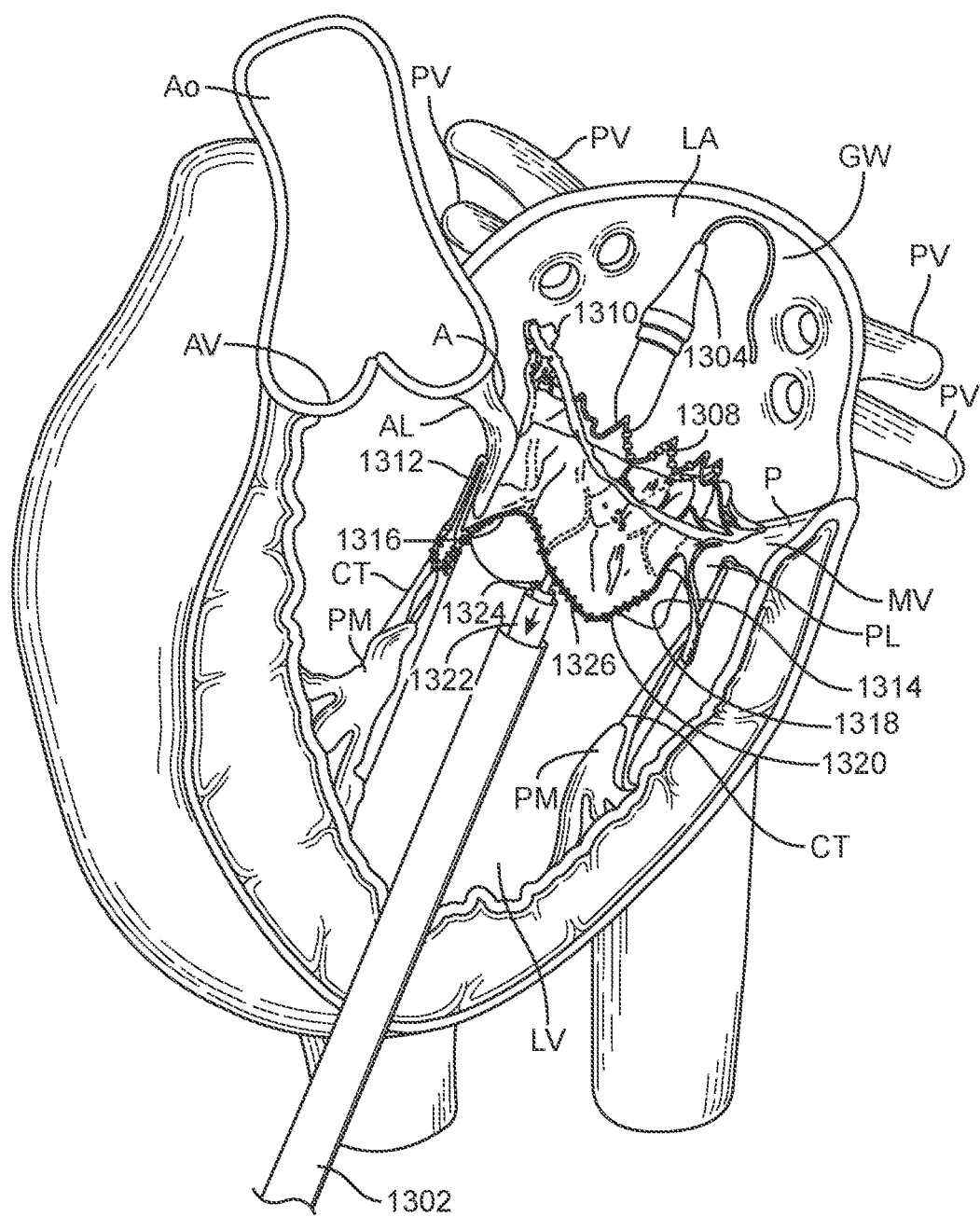
Figure 13J:
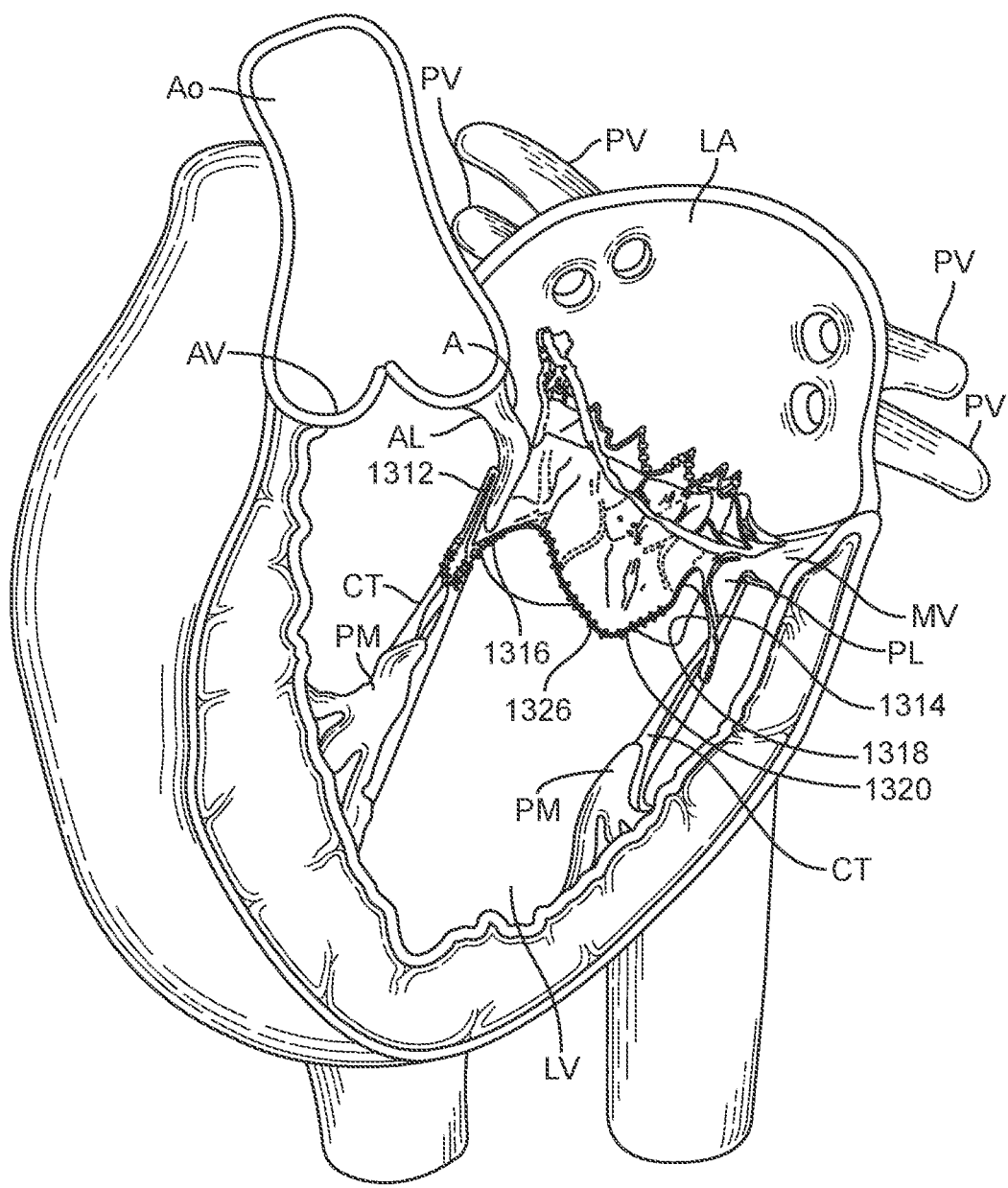

Further actuation of the delivery device now retracts the outer sheath 1306 and the bell catheter shaft 1322 so as to remove the constraint from the hub catheter 1324, as illustrated in FIG. 13I. This permits the prosthetic valve commissures 1326 to be released from the hub catheter, thus the commissures expand to their unbiased configuration. The delivery system 1302 and guidewire GW are then removed, leaving the prosthetic valve 1308 in position where it takes over for the native mitral valve, as seen in FIG. 13J.

Figure 13K:
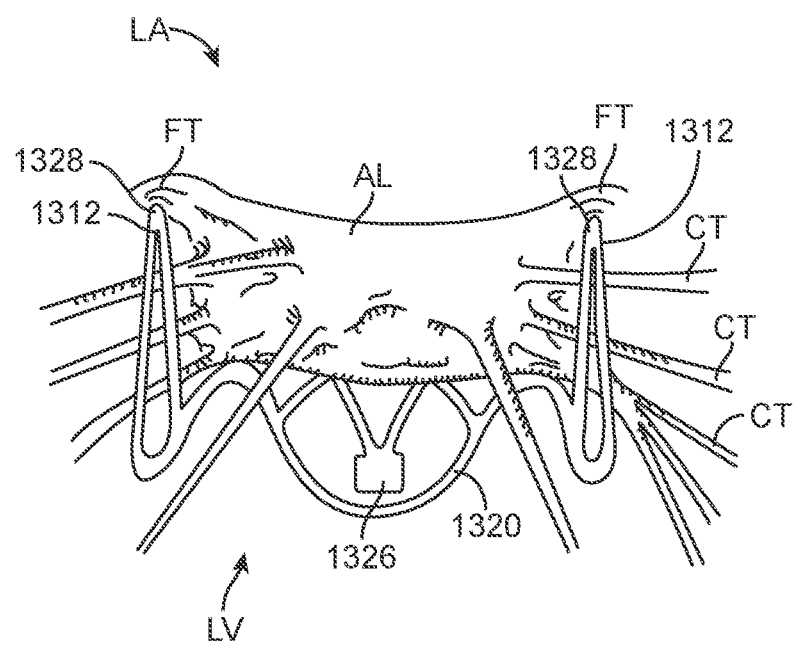
Figure 13L:
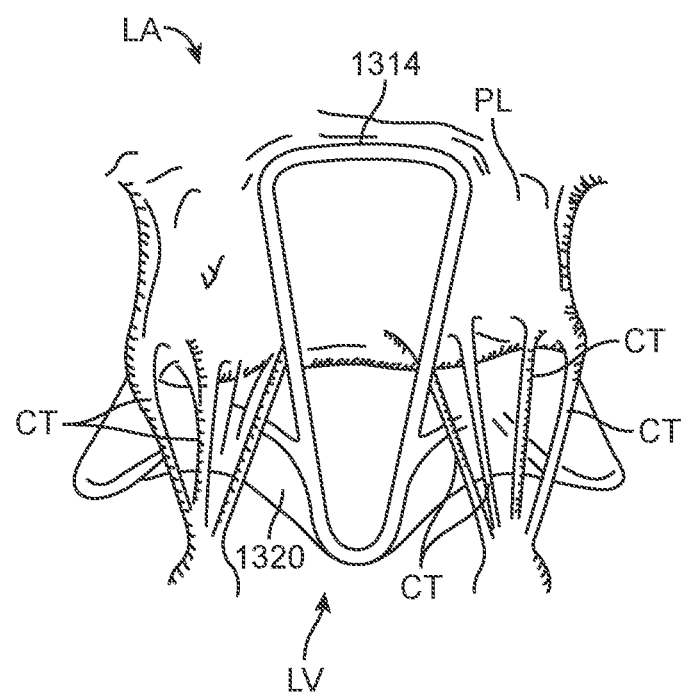

FIGS. 13K and 13L highlight engagement of the anterior and posterior tabs with the respective anterior and posterior leaflet. In FIG. 13K, after anterior tabs 1312 have been fully expanded, they capture the anterior leaflet AL and may capture adjacent chordae tendineae between an inside surface of the anterior tab and an outer surface of the ventricular skirt 1320. Moreover, the tips 1328 of the anterior tabs 1312 are engaged with the fibrous trigones FT of the anterior side of the mitral valve. The fibrous trigones are fibrous regions of the valve thus the anterior tabs further anchor the prosthetic valve into the native mitral valve anatomy. One anterior tab anchors into the left fibrous trigone, and the other anterior tabs anchors into the right fibrous trigone. The trigones are on opposite sides of the anterior side of the leaflet. FIG. 13L illustrates engagement of the posterior tab 1314 with the posterior leaflet PL which is captured between an inner surface of the posterior tab and an outer surface of the ventricular skirt 1320. Additionally, adjacent chordae tendineae may also be captured between the posterior tab and ventricular skirt.

Deployment of a prosthetic valve that includes a foot element instead of, or in conjunction with the posterior anchor element is similar to the two exemplary methods described above. The major difference being that when the prosthesis does not have a posterior anchor, retraction of the outer sheath allows the foot to self-expand to a profile large enough to minimize or prevent pivoting of the prosthesis upstream into or toward the left atrium. In embodiments having both a posterior anchor and a foot element, retraction of the outer sheath allows both structures to expand. Other aspects of the deployment are generally the same as previously described above.

Tab Covering. In the exemplary embodiments described above, the tabs (anterior trigonal tabs and posterior ventricular tab) are generally narrow and somewhat pointy. The embodiment previously described with respect to FIG. 8 includes a horizontal strut on the posterior tab that helps distribute force across a greater area and thereby reduces trauma to the tissue. FIGS. 14A-14D illustrate another embodiment that is preferably used with the anterior trigonal tabs to help reduce trauma. It may also be used with the posterior tab if desired.

Figure 14A:
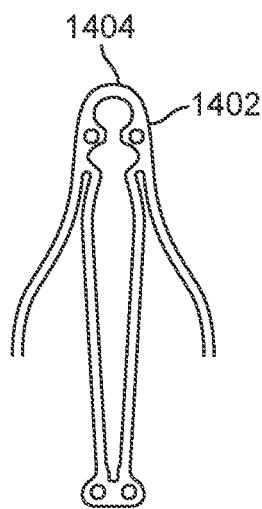
FIGS. 14A-14D illustrate an exemplary embodiment of a tab covering.
Figure 14B:
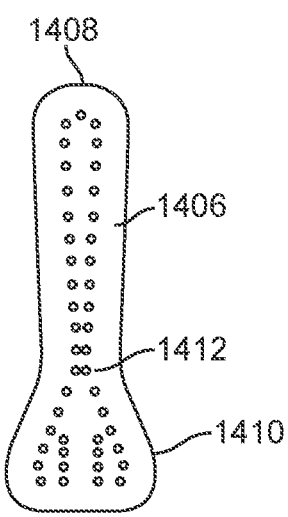
Figure 14C:
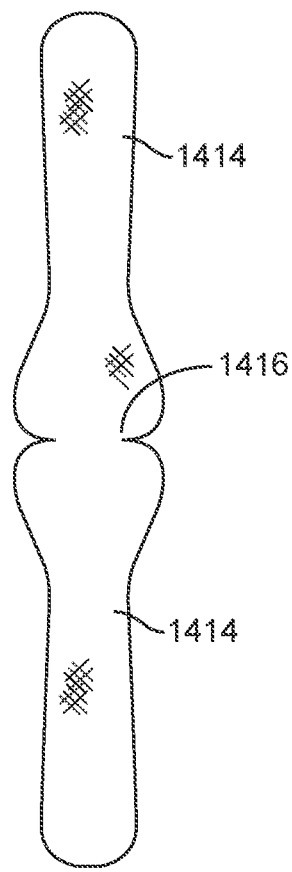
Figure 14D:
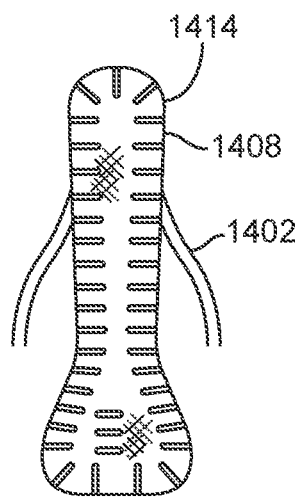

FIG. 14A illustrates an anterior trigonal tab 1402 having a tip 1404. This tip can be narrow and pointy and thereby induce tissue trauma when deployed into the tissue. Therefore, in some embodiments, it may be desirable to place a cover over the tip to help reduce tissue trauma. FIG. 14B illustrates a polymer tab 1406 that may be attached to the trigonal tab 1402. In other embodiments, the tab may be formed from other materials such as fabric, metals, or other materials known in the art. The polymer tab may be laser cut from a sheet of polymer and includes a long axial portion 1408 and an enlarged head region 1410. A plurality of suture holes 1412 may be pre-cut into the polymer tab 1406 and the holes are sized to receive suture material. Precut holes on the polymer tab may be aligned with pre-cut holes on the trigonal tab and then the polymer tab may be secured to the trigonal tab with sutures, adhesives, or other coupling techniques known in the art. A fabric cover 1414 having two symmetric halves separated by a hinged area 1416 is then wrapped around the polymer tab and attached to the polymer tab by sutures, thereby forming a shroud around the trigonal tab. The fabric may be Dacron, ePTFE, or any other biocompatible material known in the art. Thus, the cover increases the surface area of contact between the trigonal tabs and the tissue thereby reducing potential trauma and likelihood of piercing the heart wall. Additionally, the material may allow tissue ingrowth which further helps to anchor the prosthesis. Materials and dimensions are also selected in order to maintain the low profile of the device during delivery in the collapsed configuration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for anchoring a prosthetic valve in a native valve of a patient's heart, patient's heart, method comprising:
providing a prosthetic valve, wherein the prosthetic valve comprises an expandable frame having a first end, a second end opposite the first end, a first anterior tab on an anterior portion of the expandable frame adjacent the first end, a posterior tab on a posterior portion of the expandable frame adjacent the first end, a foot on a posterior portion of the expandable frame adjacent the first end, a ventricular skirt adjacent the first end of the expandable frame, and an annular region disposed between the first and second ends,
wherein the foot comprises a wedge-shaped element extending laterally and radially outward from a periphery of the ventricular skirt, and the foot comprises a plurality of struts having a length, and
wherein the posterior tab is coupled to and extends from the foot;
wherein the ventricular skirt comprises a plurality of struts having a length, and wherein the length of the plurality of struts in the foot is greater than the length of the plurality of struts in the ventricular skirt,
wherein the prosthetic valve has an expanded configuration for engaging the native valve, and a collapsed configuration;
advancing the prosthetic valve in the collapsed configuration to the native valve;
expanding the first anterior tab radially outward such that a tip of the first anterior tab engages a first fibrous trigone on a first side of an anterior leaflet of the native valve, and
wherein the anterior leaflet is disposed between the first anterior tab and an outer surface of the ventricular skirt;
expanding the posterior tab radially outward and failing to anchor the posterior tab to the native valve;
expanding the foot laterally and radially outward from the ventricular skirt such that the foot engages a posterior portion of the native valve thereby anchoring the prosthetic valve to a posterior portion of the native valve and preventing or minimizing pivoting of the prosthetic valve up into an atrium of the patient's heart; and
wherein the wedge-shaped element comprises a covering coupled to at least one of the plurality of struts of the foot that extends radially outward beyond the expandable frame.

2. The method of claim 1, wherein providing the prosthetic valve further comprises providing a delivery device for delivering the prosthetic valve to the native valve, and wherein the prosthetic valve is releasably coupled to the delivery device.

3. The method of claim 1, wherein advancing the prosthetic valve comprises transapically delivering the prosthetic valve from a region outside of the patient to the patient's heart.

4. The method of claim 1, wherein advancing the prosthetic valve comprises transseptally delivering the prosthetic valve from the right atrium to the left atrium of the patient's heart.

5. The method of claim 1, wherein the native valve is a mitral valve and wherein advancing the prosthetic valve comprises positioning the prosthetic valve across the patient's mitral valve so that the first end is inferior to the mitral valve and the second end is superior to the mitral valve.

6. The method of claim 1, wherein expanding the first anterior tab comprises retracting a constraining sheath therefrom and allowing the first anterior tab to self-expand radially outward.

7. The method of claim 1, wherein the prosthetic valve further comprises a second anterior tab on the anterior portion of the expandable frame, and the method further comprises expanding the second anterior tab radially outward such that a tip portion of the second anterior tab engages a second fibrous trigone on a second side of the anterior leaflet opposite the first side of the anterior leaflet.

8. The method of claim 7, wherein the second anterior tab expands radially outward concurrently with expansion of the first anterior tab.

9. The method of claim 7, wherein expanding the second anterior tab comprises retracting a constraining sheath from the second anterior tab so that the second anterior tab is free to self-expand radially outward.

10. The method of claim 1, wherein expanding the foot forms a vestibule adjacent the first end of the prosthetic valve.

11. The method of claim 1, wherein expanding the foot increases the size of the first end of the prosthetic valve so that it cannot pass through the native valve.

12. The method of claim 1, wherein expanding the foot comprises retracting a constraint therefrom so that the foot self-expands radially outward.

13. The method of claim 1, wherein after expanding the foot, the foot engages posterior chordae tendineae on the native heart valve.

14. The method of claim 1, wherein the foot comprises barbs, texturing, or other surface features, and wherein expanding the foot engages the barbs, texturing or other surface features with tissue, thereby anchoring the foot with the tissue.

15. The method of claim 1, further comprising expanding the ventricular skirt radially outward into engagement with the anterior and posterior leaflets of the native valve.

16. The method of claim 15, wherein the first anterior tab and the outer surface of the ventricular skirt engage anterior chordae tendineae of the native heart there between.

17. The method of claim 15, wherein expanding the ventricular skirt comprises retracting a constraining sheath from the ventricular skirt so that the ventricular skirt is free to self-expand radially outward.

18. The method of claim 15, wherein the ventricular skirt comprises a plurality of barbs, and wherein expanding the ventricular skirt comprises anchoring the plurality of barbs into heart tissue.

19. The method of claim 15, wherein the prosthetic valve further comprises a plurality of commissures, and wherein expanding the ventricular skirt displaces anterior and posterior leaflets of the native valve radially outward thereby preventing interference between the commissures and the leaflets.

20. The method of claim 15, wherein expanding the ventricular skirt displaces anterior and posterior leaflets of the native valve radially outward without contacting an inner wall of the left ventricle, and without obstructing a left ventricular outflow tract.

21. The method of claim 15, wherein radially expanding the ventricular skirt expands the ventricular skirt asymmetrically such that an anterior portion of the ventricular skirt is substantially flat, and a posterior portion of the ventricular skirt is cylindrically shaped.

22. The method of claim 1, further comprising expanding the annular region radially outward so as to engage an annulus of the native valve.

23. The method of claim 22, wherein expanding the annular region comprises retracting a constraining sheath therefrom so that the annular region is free to self-expand radially outward.

24. The method of claim 22, wherein expanding the annular region comprises asymmetrically expanding the annular region such that an anterior portion of the annular region is substantially flat, and a posterior portion of the annular region is cylindrically shaped.

25. The method of claim 1, wherein the native valve is a mitral valve, the method further comprising reducing or eliminating mitral regurgitation.

26. The method of claim 1, wherein the prosthetic valve carries a therapeutic agent, and the method further comprises eluting the therapeutic agent from the prosthetic valve into adjacent tissue.

27. The method of claim 1, wherein the prosthetic valve comprises an alignment element, and wherein a second fibrous trigone is disposed on a second side of the anterior leaflet opposite the first side of the anterior leaflet, the method further comprising aligning the alignment element with an aortic root and disposing the alignment element between the first and second fibrous trigones.

28. The method of claim 27, wherein aligning the alignment element comprises rotating the prosthetic valve.

29. The method of claim 1, wherein the prosthetic valve further comprises a plurality of commissures with a covering disposed thereover whereby a plurality of prosthetic valve leaflets are formed, the method further comprising releasing the plurality of prosthetic valve leaflets from a delivery catheter.

30. The method of claim 29, wherein the plurality of prosthetic valve leaflets form a tricuspid valve, the tricuspid valve having an open configuration and a closed configuration, wherein the plurality of prosthetic valve leaflets are disposed away from one another in the open configuration thereby permitting antegrade blood flow therethrough, and wherein the plurality of prosthetic valve leaflets engage one another in the closed configuration thereby substantially preventing retrograde blood flow therethrough.

31. The method of claim 1, wherein the prosthetic valve further comprises an atrial skirt adjacent the second end, the method further comprising:
   expanding the atrial skirt radially outward so as to lie over a superior surface of the native valve; and
   engaging the atrial skirt against the superior surface of the native valve.

32. The method of claim 31, wherein expanding the atrial skirt comprises retracting a constraining sheath from the atrial skirt so that the atrial skirt is free to self-expand radially outward.

33. The method of claim 31, further comprising moving the prosthetic valve upstream or downstream relative to the native valve to ensure that the atrial skirt engages the superior surface of the native valve.

34. The method of claim 31, wherein engaging the atrial skirt against the superior surface seals the atrial skirt against the superior surface of the native valve to prevent or substantially prevent blood flow therebetween.

35. The method of claim 1, wherein the plurality of struts of the foot comprises a pair of elongate struts.

36. The method of claim 35, wherein the pair of elongate struts are coupled together to form a U-shape or a V-shape.

* * * * *

UNITED STATES PATENT AND TRADEMARK OFFICE
CERTIFICATE OF CORRECTION

PATENT NO. : 10,583,002 B2
APPLICATION NO. : 14/195576
DATED : March 10, 2020
INVENTOR(S) : Lane et al.

Page 1 of 1

It is certified that error appears in the above-identified patent and that said Letters Patent is hereby corrected as shown below:

In the Claims

In Column 26, Line 14, in Claim 1, delete "patient's heart, patient's heart," and insert --patient's heart, the-- therefor Signed and Sealed this
Seventeenth Day of November, 2020

Andrei Iancu
*Director of the United States Patent and Trademark Office*